United States Patent
Bava et al.

(10) Patent No.: US 12,071,667 B2
(45) Date of Patent: Aug. 27, 2024

(54) SEQUENCE ANALYSIS USING META-STABLE NUCLEIC ACID MOLECULES

(71) Applicant: 10x Genomics, Inc., Pleasanton, CA (US)

(72) Inventors: Felice Alessio Bava, Rome (IT); Eswar Prasad Ramachandran Iyer, Sunnyvale, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 174 days.

(21) Appl. No.: 17/518,264

(22) Filed: Nov. 3, 2021

(65) Prior Publication Data
US 2022/0136049 A1    May 5, 2022

Related U.S. Application Data

(60) Provisional application No. 63/109,810, filed on Nov. 4, 2020.

(51) Int. Cl.
*C12Q 1/6876* (2018.01)
*C12Q 1/6855* (2018.01)

(52) U.S. Cl.
CPC ......... *C12Q 1/6876* (2013.01); *C12Q 1/6855* (2013.01); *C12Q 2600/156* (2013.01)

(58) Field of Classification Search
CPC ............... C12Q 1/6876; C12Q 1/6855; C12Q 2600/156
See application file for complete search history.

(56) References Cited

U.S. PATENT DOCUMENTS

| | | | |
|---|---|---|---|
| 4,318,846 A | 3/1982 | Khanna et al. |
| 4,757,141 A | 7/1988 | Fung et al. |
| 4,849,336 A | 7/1989 | Miyoshi et al. |
| 5,066,580 A | 11/1991 | Lee |

(Continued)

FOREIGN PATENT DOCUMENTS

| | | |
|---|---|---|
| WO | WO 1991/017160 | 11/1991 |
| WO | WO 2005/065814 | 7/2005 |

(Continued)

OTHER PUBLICATIONS

Zhong et al., Visualization of oligonucleotide probes and point mutations in interphase nuclei and DNA fibers using rolling circle DNA amplification; Proc Natl Acad Sci U S A, 98 (2001), pp. 3940-3945) (Year: 2001).*

(Continued)

*Primary Examiner* — Aaron A Priest
*Assistant Examiner* — Tian Yu
(74) *Attorney, Agent, or Firm* — MORRISON & FOERSTER LLP

(57) ABSTRACT

The present disclosure relates in some aspects to methods for analyzing a target nucleic acid in a biological sample. In some aspects, the methods involve the use of a set of probe polynucleotides, for example a set of three or more probe polynucleotides, for assessing target nucleic acids. In some aspects, the presence, amount, and/or identity of region of interest in a target nucleic acid is analyzed in situ. Also provided are polynucleotides, sets of polynucleotides, compositions, and kits for use in accordance with the methods.

18 Claims, 10 Drawing Sheets

(56) References Cited

U.S. PATENT DOCUMENTS

| | | |
|---|---|---|
| 5,091,519 A | 2/1992 | Cruickshank |
| 5,151,507 A | 9/1992 | Hobbs et al. |
| 5,188,934 A | 2/1993 | Menchen |
| 5,198,537 A | 3/1993 | Huber et al. |
| 5,344,757 A | 9/1994 | Holtke et al. |
| 5,354,657 A | 10/1994 | Boehringer et al. |
| 5,366,860 A | 11/1994 | Bergot et al. |
| 5,599,675 A | 2/1997 | Brenner |
| 5,635,352 A | 6/1997 | Urdea et al. |
| 5,688,648 A | 11/1997 | Mathies |
| 5,695,940 A | 12/1997 | Drmanac et al. |
| 5,702,888 A | 12/1997 | Holtke et al. |
| 5,750,341 A | 5/1998 | Macevicz |
| 5,800,996 A | 9/1998 | Lee et al. |
| 5,847,162 A | 12/1998 | Lee et al. |
| 5,990,479 A | 11/1999 | Weiss et al. |
| 6,054,274 A | 4/2000 | Sampson et al. |
| 6,172,218 B1 | 1/2001 | Brenner |
| 6,207,392 B1 | 3/2001 | Weiss et al. |
| 6,251,303 B1 | 6/2001 | Bawendi et al. |
| 6,291,187 B1 | 9/2001 | Kingsmore et al. |
| 6,306,597 B1 | 10/2001 | Macevicz |
| 6,319,426 B1 | 11/2001 | Bawendi et al. |
| 6,322,901 B1 | 11/2001 | Bawendi et al. |
| 6,323,009 B1 | 11/2001 | Lasken et al. |
| 6,344,329 B1 | 2/2002 | Lizardi et al. |
| 6,368,801 B1 | 4/2002 | Faruqi |
| 6,423,551 B1 | 7/2002 | Weiss et al. |
| 6,426,513 B1 | 7/2002 | Bawendi et al. |
| 6,444,143 B2 | 9/2002 | Bawendi et al. |
| 6,534,266 B1 | 3/2003 | Singer |
| 6,576,291 B2 | 6/2003 | Bawendi et al. |
| 6,969,488 B2 | 11/2005 | Bridgham et al. |
| 6,969,589 B2 | 11/2005 | Patil et al. |
| 7,057,026 B2 | 6/2006 | Barnes et al. |
| 7,255,994 B2 | 8/2007 | Lao |
| 7,473,767 B2 | 1/2009 | Dimitrov |
| 7,534,991 B2 | 5/2009 | Miller et al. |
| 7,555,155 B2 | 6/2009 | Levenson et al. |
| 7,655,898 B2 | 2/2010 | Miller |
| 7,910,304 B2 | 3/2011 | Drmanac |
| 7,941,279 B2 | 5/2011 | Hwang et al. |
| 7,989,166 B2 | 8/2011 | Koch et al. |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,658,361 B2 | 2/2014 | Wu et al. |
| 8,771,950 B2 | 7/2014 | Church et al. |
| 8,986,926 B2 | 3/2015 | Ferree et al. |
| 9,201,063 B2 | 12/2015 | Sood et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,541,504 B2 | 1/2017 | Hoyt |
| 9,551,032 B2 | 1/2017 | Landegren et al. |
| 9,624,538 B2 | 4/2017 | Church et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,138,509 B2 | 11/2018 | Church et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,459,603 B2 | 10/2022 | Tyagi et al. |
| 2002/0045045 A1 | 4/2002 | Adams et al. |
| 2003/0017264 A1 | 1/2003 | Treadway et al. |
| 2005/0100900 A1 | 5/2005 | Kawashima et al. |
| 2006/0188875 A1 | 8/2006 | Cox et al. |
| 2006/0188901 A1 | 8/2006 | Barnes et al. |
| 2006/0240439 A1 | 10/2006 | Smith et al. |
| 2006/0281109 A1 | 12/2006 | Barr et al. |
| 2007/0166705 A1 | 7/2007 | Milton et al. |
| 2010/0055733 A1 | 3/2010 | Lutolf et al. |
| 2011/0223585 A1 | 9/2011 | Gullberg et al. |
| 2012/0270305 A1 | 10/2012 | Reed et al. |
| 2013/0079232 A1 | 3/2013 | Kain et al. |
| 2013/0260372 A1 | 10/2013 | Buermann et al. |
| 2013/0288249 A1 | 10/2013 | Gullbert |
| 2013/0323729 A1 | 12/2013 | Landegren et al. |
| 2014/0194311 A1 | 6/2014 | Gullberg et al. |
| 2016/0024555 A1 | 1/2016 | Church et al. |
| 2016/0108458 A1 | 4/2016 | Frei et al. |
| 2016/0305856 A1 | 10/2016 | Boyden et al. |
| 2016/0369329 A1 | 12/2016 | Cai et al. |
| 2016/0376642 A1 | 12/2016 | Landegren et al. |
| 2017/0009278 A1 | 1/2017 | Söderberg et al. |
| 2017/0081489 A1 | 3/2017 | Rodriques et al. |
| 2017/0101672 A1 | 4/2017 | Luo et al. |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0251833 A1 | 9/2018 | Daugharthy et al. |
| 2018/0320226 A1 | 11/2018 | Church et al. |
| 2019/0017106 A1 | 1/2019 | Frisen et al. |
| 2019/0032121 A1 | 1/2019 | Daugharthy et al. |
| 2019/0032128 A1 | 1/2019 | Chen et al. |
| 2019/0055594 A1 | 2/2019 | Samusik et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |

(56) References Cited

U.S. PATENT DOCUMENTS

| | | |
|---|---|---|
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239946 A1 | 7/2020 | Dewal |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |
| 2021/0017587 A1 | 1/2021 | Cai et al. |
| 2021/0115504 A1 | 4/2021 | Cai et al. |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0340621 A1 | 11/2021 | Daugharthy et al. |
| 2021/0388423 A1 | 12/2021 | Bava et al. |
| 2021/0388424 A1 | 12/2021 | Bava |
| 2022/0049302 A1 | 2/2022 | Daugharthy et al. |
| 2022/0049303 A1 | 2/2022 | Busby et al. |
| 2022/0083832 A1 | 3/2022 | Shah |
| 2022/0084628 A1 | 3/2022 | Shah |
| 2022/0084629 A1 | 3/2022 | Shah |
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |

FOREIGN PATENT DOCUMENTS

| | | | |
|---|---|---|---|
| WO | WO 2006/064199 | 6/2006 | |
| WO | WO 2007/010251 | 1/2007 | |
| WO | WO 2014/025392 | 2/2014 | |
| WO | WO 2014/163886 | 10/2014 | |
| WO | WO 2017/079406 | 5/2017 | |
| WO | WO 2017/143155 | 8/2017 | |
| WO | WO 2018/026873 | 2/2018 | |
| WO | WO 2018/045181 | 3/2018 | |
| WO | WO 2018/045186 | 3/2018 | |
| WO | WO 2019/199579 | 10/2019 | |
| WO | WO-2019199579 A1 * | 10/2019 | ............ C12Q 1/682 |
| WO | WO-2020056381 A1 * | 3/2020 | ............ C07H 21/02 |
| WO | WO 2020/076976 | 4/2020 | |
| WO | WO 2020/076979 | 4/2020 | |
| WO | WO 2020/096687 | 5/2020 | |
| WO | WO 2020/099640 | 5/2020 | |
| WO | WO 2020/117914 | 6/2020 | |
| WO | WO 2020/123316 | 6/2020 | |
| WO | WO 2020/123742 | 6/2020 | |
| WO | WO 2020/142490 | 7/2020 | |
| WO | WO 2020/240025 | 12/2020 | |
| WO | WO 2020/254519 | 12/2020 | |
| WO | WO 2021/123282 | 6/2021 | |
| WO | WO 2021/123286 | 6/2021 | |
| WO | WO 2021/155063 | 8/2021 | |
| WO | WO 2021/168326 | 8/2021 | |

OTHER PUBLICATIONS

Allawi et al., "Thermodynamics and NMR of internal G.T mismatches in DNA," Biochemistry, (1997) 36:10581-94.
Baner et al., "Signal amplification of padlock probes by rolling circle replication," Nucleic Acids Res. (1998) 26(22):5073-5078.
Bibikova et al., "Quantitative gene expression profiling in formalin-fixed, paraffin-embedded tissues using universal bead arrays," Am J Pathol. Nov. 2004;165(5):1799-807.
Bolognesi et al., "Multiplex Staining by Sequential Immunostaining and Antibody Removal on Routine Tissue Sections," J. Histochem. Cytochem. (2017); 65(8): 431-444.
Capodieci et al., "Gene expression profiling in single cells within tissue," Nat Methods. (2005) 2(9): 663-5.
Chen et al., "Nanoscale imaging of RNA with expansion microscopy," Nat Methods. (2016) 13:679-684.
Chen et al., "Expansion Microscopy," Science (2015) 347(6221):543-548.
Chen et al., "RNA imaging. Spatially resolved, highly multiplexed RNA profiling in single cells," Science. (2015) 348(6233): aaa6090. 16 pgs.
Chung et al., "Clarity for mapping the nervous system," Nat Methods. Jun. 2013;10(6):508-13.
Conze et al., "Single molecule analysis of combinatorial splicing," Nucleic Acids Res. (2010) 38(16): e163.
Dean et al., "Rapid Amplification Of Plasmid And Phage DNA Using Phi29 DNA Polymerase And Multiply-Primed Rolling Circle Amplification," Genome Research (2001) 11:1095-1099.
Eng et al., "Transcriptome-scale super-resolved imaging in tissues by RNA seqFISH," Nature. (2019) 568(7751): 235-239.
Faruqi et al., "High-throughput genotyping of single nucleotide polymorphisms with rolling circle amplification," BMC Genomics. (2001) 2:4.
Femino et al., "Visualization of single RNA transcripts in situ," Science. (1998) 280(5363): 585-90.
Gavrilovic et al., "Automated classification of multicolored rolling circle products in dual-channel wide-field fluorescence microscopy," Cytometry A. (2011) 79(7): 518-27.
Geiss et al., "Direct multiplexed measurement of gene expression with color-coded probe pairs," Nat Biotechnol. (2008) 26(3): 317-25.
Glass et al., "Simple: a sequential immunoperoxidase labeling and erasing method," J Histochem Cytochem. (2009) 57(10); 899-905.
Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.
Goransson et al., "A single molecule array for digital targeted molecular analyses," Nucleic Acids Res. 2009 37(1):e7. doi: 10.1093/nar/gkn921.
Gunderson et al. "Decoding randomly ordered DNA arrays." Genome research 14.5 (2004): 870-877.
Han et al., "Quantum-dot-tagged microbeads for multiplexed optical coding of biomolecules," Nat Biotechnol. (2001) 19(7): 631-5.
Itzkovitz et al., "Validating Transcripts with Probes and Imaging Technology," Nat Methods. (2011) 8(4 Suppl): S12-S19.
Itzkovitz et al., "Single-molecule transcript counting of stem-cell markers in the mouse intestine," Nat Cell Biol. (2011) 14(1): 106-14.
Jamur et al., "Permeabilization of cell membranes," Method Mol. Biol. (2010) 588: 63-66 (abstract only).
Kanehisa, "Use of statistical criteria for screening potential homologies in nucleic acid sequences," Nucleic Acids Res. (1984) 12:203-213.
Korlach et al. "Selective aluminum passivation for targeted immobilization of single DNA polymerase molecules in zero-mode waveguide nanostructures." *Proceedings of the National Academy of Sciences* 105.4 (2008): 1176-1181.
Kwok et al., "High-throughput genotyping assay approaches," Pharmacogenomics. (2000) 1(1) 95-100; 5 pages.
Lagunavicius et al., "Novel application of Phi29 DNA polymerase: RNA detection and analysis in vitro and in situ by target RNA-primed RCA," RNA. (2009) 15(5):765-71.
Lakowicz et al., "Silver particles enhance emission of fluorescent DNA oligomers," Bio Techniques (2003) 34(1); 62-66.
Landegren et al., "Reading bits of genetic information: methods for single-nucleotide polymorphism analysis," Genome Res. (1998) 8(8): 769-776.
Larsson et al. "In situ detection and genotyping of individual mRNA molecules," Nat Methods. (2010) 7(5):395-397.
Lee et al. "Highly Multiplexed Subcellular RNA Sequencing In Situ", Science (2014) 343(6177):1360-1363.

(56) References Cited

OTHER PUBLICATIONS

Levene et al. "Zero-mode waveguides for single-molecule analysis at high concentrations." *science* 299.5607 (2003): 682-686.
Levsky et al., "Fluorescence in situ hybridization: past, present and future," J Cell Sci. (2003) 116(Pt 14): 2833-8.
Levsky et al., "Single-cell gene expression profiling," Science. (2002) 297(5582): 836-40.
Lin et al., "Highly multiplexed imaging of single cells using a high-throughput cyclic immunofluorescence method," Nat Commun. (2015) 6:8390.
Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.
Lizardi et al., "Mutation detection and single-molecule counting using isothermal rolling-circle amplification," Nat Genet. (1998) 19(3): 225-232.
Lundquist et al. "Parallel confocal detection of single molecules in real time." Optics letters 33.9 (2008): 1026-1028.
Maierhorfer et al., "Multicolor deconvolution microscopy of thick biological specimens," Am J Pathol. (2003) 162(2): 373-9.
McGinn et al., "New technologies for DNA analysis—a review of the READNA Project," N Biotechnol. (2016) 33(3): 311-30. doi: 10.1016/j.nbt.2015.10.003.
Meade et al. "Multiplexed DNA detection using spectrally encoded porous SiO2 photonic crystal particles," Anal Chem. (2009) 81(7): 2618-25.
Mitra et al., "Fluorescent in situ sequencing on polymerase colonies," Anal. Biochem. (2003) 320, 55-65.
Moffitt et al., "RNA Imaging with Multiplexed Error-Robust Fluorescence In Situ Hybridization (MERFISH)," Methods in Enzymology, (2016) 572; 1-49.
Mohsen et al., "The Discovery of Rolling Circle Amplification and Rolling Circle Transcription," Acc Chem Res. (2016) 49(11): 2540-2550.
Nallur et al., "Signal amplification by rolling circle amplification on DNA microarrays," Nucleic Acids Res. (2001) 29(23): e118.
Payne et al. "In situ genome sequencing resolves DNA sequence and structure in intact biological samples," Science. (2021) 371(6532): eaay3446. doi: 10.1126/science.aay3446. Epub Dec. 31, 2020.
Pirici et al., "Antibody elution method for multiple immunohistochemistry on primary antibodies raised in the same species and of the same subtype," J Histochem Cytochem. (2009) 57(6); 567-75.
Raj et al., "Imaging individual mRNA molecules using multiple singly labeled probes," Nat Methods. (2008) 5(10): 877-879.
Rouhanifard et al. "ClampFISH detects individual nucleic acid molecules using click chemistry-based amplification," Nat Biotechnol. (2018) 17 pages. doi: 10.1038/nbt.4286.
Schweitzer et al., "Multiplexed protein profiling on microarrays by rolling-circle amplification," Nature Biotech. (2002) 20:359-365.
Schweitzer et al. "Immunoassays with rolling circle DNA amplification: A versatile platform for ultrasensitive antigen detection," Proc. Natl Acad. Sci. USA (2000) 97:10113-119.
Shendure et al, "Accurate multiplex polony sequencing of an evolved bacterial genome," Science (2005) 309(5741); 1728-1732.
Shi. "Enabling large-scale pharmacogenetic studies by high-throughput mutation detection and genotyping technologies." *Clinical chemistry* 47.2 (2001): 164-172.
Soderberg et al. "Characterizing proteins and their interactions in cells and tissues using the in situ proximity ligation assay." *Methods* 45.3 (2008): 227-232.
Sun et al., "Composite organic-inorganic nanoparticles as Raman labels for tissue analysis," Nano Lett. (2007) 7(2): 351-6.
Takei et al., (Feb. 2021, e-pub Jan. 27, 2021). "Integrated Spatial Genomics Reveals Global Architecture Of Single Nuclei," Nature 590(7845):344-350, 53 pages. doi: 10.1038/s41586-020-03126-2.
Wählby et al., "Sequential immunofluorescence staining and image analysis for detection of large numbers of antigens in individual cell nuclei," Cytometry. (2002) 47(1):32-41.
Wang et al., "Three-dimensional intact-tissue sequencing of single-cell transcriptional states," Science. (2018) 361(6400): eaat5691.
Weibrecht et al., "Simultaneous visualization of both signaling cascade activity and end-point gene expression in single cells," PLoS One. (2011) 6(5): e20148.
Wetmur, "DNA Probes: Applications of the Principles of Nucleic Acid Hybridization," Critical Reviews in Biochemistry and Molecular Biology, (1991) 26(91); 227-259.
Wilson et al., "Encoded microcarriers for high-throughput multiplexed detection," Angew Chem Int Ed Engl. (2006) 18;45(37): 6104-17.
Wu, C. et al. "RollFISH Achieves Robust Quantification Of Single-Molecule RNA Biomarkers In Paraffin-Embedded Tumor Tissue Samples," Commun Biol. (2018) 1:(209):1-8. doi: 10.1038/s42003-018-0218-0.
Zhao et al., "Advances of multiplex and high throughput biomolecular detection technologies based on encoding microparticles," Sci China Chem. (2011) 54(8):1185.

* cited by examiner

SEQUENCE ANALYSIS USING META-STABLE NUCLEIC ACID MOLECULES

CROSS REFERENCE TO RELATED APPLICATIONS

This application claims priority to U.S. Provisional Patent Application No. 63/109,810, filed Nov. 4, 2020, entitled "SEQUENCE ANALYSIS USING META-STABLE NUCLEIC ACID MOLECULES," which is herein incorporated by reference in its entirety for all purposes.

FIELD

The present disclosure relates in some aspects to methods and compositions for analysis of a target nucleic acid in a sample (e.g., in situ), such as the detection of a region of interest (e.g., a sequence polymorphism comprising a single nucleotide of interest) in a polynucleotide.

BACKGROUND

Methods are available for analyzing nucleic acids present in a biological sample, such as a cell or a tissue. For instance, advances in single molecule fluorescent in situ hybridization (smFISH) have enabled nanoscale-resolution imaging of RNA in cells and tissues. However, analysis of short sequences (e.g., single nucleotide polymorphisms (SNPs) or point mutations) on individual transcripts has remained challenging. Improved methods for analyzing nucleic acids present in a biological sample, such as in situ SNP genotyping, are needed. Provided herein are methods and compositions that address such and other needs.

BRIEF SUMMARY

Fluorescent in situ hybridization (FISH) assays may suffer from low probe specificity and the inability to distinguish single bases, especially when applied to the analysis of short sequences such as SNP genotyping or detection of point mutations. Because FISH assays do not require nucleic acid amplification, the signals are typically low in intensity, resulting in low signal-to-noise ratios and low sensitivity/specificity. FISH assays may also have limited plexy and can be biased, time-consuming, labor-intensive, and/or error-prone for the analysis of short sequences.

In situ sequencing methods are useful for analyzing a target nucleic acid in a cell or tissue sample. For example, a SNAIL (Splint Nucleotide Assisted Intramolecular Ligation) probe set may be used to form a circular construct on an RNA molecule. The circular construct is then amplified (e.g., by rolling circle amplification (RCA)) for in situ sequencing, such as sequencing by ligation (e.g., Sequencing by Dynamic Annealing and Ligation (SEDAL)). See, e.g., U.S. Pat. Pub. 20190055594 and WO2019199579A1, which are hereby incorporated by reference in their entirety. However, detection of polymorphisms or a single nucleotide of interest such as SNP genotyping in situ using SNAIL probes has not been possible.

Provided herein are methods and compositions that enable detecting regions of interest in a target nucleic acid (e.g., polymorphisms). Provided herein are methods and compositions that enable single nucleotide discrimination in situ. In some embodiments, a method disclosed herein comprises performing one or more ligation reactions (e.g., proximity ligation) in a hybridization complex comprising one or more short, meta-stable oligos hybridized to a target nucleic acid. In some aspects, provided here are methods and compositions for direct in situ RNA detection using one or more oligos comprising a meta-stable primer (in some instances also referred to as a priming probe) and/or a meta-stable anchor. In some embodiments, the meta-stable oligos are designed to bind or hybridize to a target nucleic acid for a short period of time. In some aspects, the meta-stable oligos may dehybridize from the target nucleic acid if the reaction temperature is greater than the $T_m$. In some embodiments, the meta-stable oligos are designed to be ligated after hybridization to the target nucleic acid, and a ligation product of a meta-stable oligo can provide greater and/or longer term stability compared to the oligo prior to the ligation. Standard design considerations used for primer design may be applied, such as for calculating the $T_m$ of nucleic acids, which are known in the art.

In some embodiments, provided herein is a method for analyzing a region of interest in a target nucleic acid, the method comprising: (i) contacting a target nucleic acid with (a) a circular or padlock probe, (b) a primer, and (c) an anchor to form a hybridization complex, wherein: (1) the circular or padlock probe comprises adjacent hybridization regions HR1 and HRa, the primer comprises adjacent hybridization regions HRb and HR2, the anchor comprises hybridization region HR3, and the target nucleic acid comprises adjacent hybridization regions HR1', HR2', and HR3', wherein HR2' or HR3' comprises the region of interest, and (2) HR1 hybridizes to HR1', HRa hybridizes to HRb, HR2 or HR3 comprises at least one nucleotide complementary to the region of interest, and HR2 and HR3 hybridize to HR2' and HR3', respectively, thereby hybridizing the circular or padlock probe, the primer, and the anchor to the target nucleic acid; (ii) ligating the 3' end of the anchor and the 5' end of the primer, optionally preceded by gap filling, to form a ligated anchor-primer; (iii) forming an amplification product using the circular probe or a circular probe formed from the padlock probe as a template and the ligated anchor-primer as a primer; and (iv) detecting the amplification product. In some embodiments, the region of interest comprises a polymorphism (e.g., a single nucleotide of interest).

In some embodiments, provided herein is a method for analyzing a region of interest in a target nucleic acid, the method comprising contacting (a) a target nucleic acid with (b) a circular or padlock probe, (c) a primer, and (d) an anchor to form a hybridization complex, wherein: (1) the circular or padlock probe comprises adjacent hybridization regions HR1 and HRa, the primer comprises adjacent hybridization regions HRb and HR2, the anchor comprises hybridization region HR3, and the target nucleic acid comprises adjacent hybridization regions HR1', HR2', and HR3', wherein HR2' or HR3' comprises the region of interest; (2) HR1 hybridizes to HR1', HRa hybridizes to HRb, HR2 or HR3 comprises at least one nucleotide complementary to the region of interest, and HR2 and HR3 hybridize to HR2' and HR3', respectively, thereby hybridizing the circular or padlock probe, the primer, and the anchor to the target nucleic acid; (3) the 3' end of the anchor and the 5' end of the primer are ligated, optionally preceded by gap filling, to form a ligated anchor-primer; (4) the circular probe or a circular probe formed from the padlock probe and the ligated anchor-primer are used as a template and a primer, respectively, to form an amplification product; and (b) the amplification product is detected. In some embodiments, the region of interest comprises a polymorphism (e.g., a single nucleotide of interest).

In some embodiments, provided herein is a method for analyzing a region of interest in a target nucleic acid, the method comprising ligating the 3' end of an anchor and the 5' end of a primer, optionally preceded by gap filling, to form a ligated anchor-primer, wherein: (1) the anchor and the primer form a hybridization complex with a target nucleic acid and a circular or padlock probe; (2) the circular or padlock probe comprises adjacent hybridization regions HR1 and HRa, the primer comprises adjacent hybridization regions HRb and HR2, the anchor comprises hybridization region HR3, and the target nucleic acid comprises adjacent hybridization regions HR1', HR2', and HR3', wherein HR2' or HR3' comprises the region of interest; (3) HR1 hybridizes to HR1', HRa hybridizes to HRb, HR2 or HR3 comprises at least one nucleotide complementary to the region of interest, and HR2 and HR3 hybridize to HR2' and HR3', respectively, thereby hybridizing the circular or padlock probe, the primer, and the anchor to the target nucleic acid; (4) the circular probe or a circular probe formed from the padlock probe and the ligated anchor-primer are used as a template and a primer, respectively, to form an amplification product; and (5) the amplification product is detected. In some embodiments, the region of interest comprises a polymorphism (e.g., a single nucleotide of interest).

In some embodiments, provided herein is a method for analyzing a region of interest in a target nucleic acid, wherein (a) a target nucleic acid, (b) a circular or padlock probe, (c) a primer, and (d) an anchor form a hybridization complex, the circular or padlock probe (b) comprises adjacent hybridization regions HR1 and HRa, the primer (c) comprises adjacent hybridization regions HRb and HR2, the anchor (d) comprises hybridization region HR3, and the target nucleic acid (a) comprises adjacent hybridization regions HR1', HR2', and HR3', wherein HR2' or HR3' comprises the region of interest; wherein HR1 hybridizes to HR1', HRa hybridizes to HRb, HR2 or HR3 comprises at least one nucleotide complementary to the region of interest, and HR2 and HR3 hybridize to HR2' and HR3', respectively, thereby hybridizing the circular or padlock probe, the primer, and the anchor to the target nucleic acid; and wherein the 3' end of an anchor and the 5' end of a primer are ligated, optionally preceded by gap filling, to form a ligated anchor-primer, the method comprising: (i) forming an amplification product using the circular probe or a circular probe formed from the padlock probe as a template and the ligated anchor-primer as a primer, wherein (ii) the amplification product is detected. In some embodiments, the region of interest comprises a polymorphism (e.g., a single nucleotide of interest).

In some embodiments, there is provided herein a method for analyzing a region of interest in a target nucleic acid, wherein (a) a target nucleic acid, (b) a circular or padlock probe, (c) a primer, and (d) an anchor form a hybridization complex, the circular or padlock probe (b) comprises adjacent hybridization regions HR1 and HRa, the primer (c) comprises adjacent hybridization regions HRb and HR2, the anchor (d) comprises hybridization region HR3, and the target nucleic acid (a) comprises adjacent hybridization regions HR1', HR2', and HR3', wherein HR2' or HR3' comprises the region of interest; (1) wherein HR1 hybridizes to HR1', HRa hybridizes to HRb, HR2 or HR3 comprises at least one nucleotide complementary to the region of interest, and HR2 and HR3 hybridize to HR2' and HR3', respectively, thereby hybridizing the circular or padlock probe, the primer, and the anchor to the target nucleic acid; (2) wherein the 3' end of an anchor and the 5' end of a primer are ligated, optionally preceded by gap filling, to form a ligated anchor-primer; and (3) wherein the circular probe or a circular probe formed from the padlock probe and the ligated anchor-primer are used as a template and a primer, respectively, to form an amplification product, the method comprising detecting the amplification product. In some embodiments, the region of interest comprises a polymorphism (e.g., a single nucleotide of interest).

In any of the preceding embodiments, the 3' end of the anchor and the 5' end of the primer can be directly juxtaposed to each other when hybridized to the target nucleic acid.

In any of the preceding embodiments, the 3' end of the anchor and the 5' end of the primer can be in proximity to each other but separated by a gap when hybridized to the target nucleic acid.

In any of the preceding embodiments, the target nucleic acid can comprise an RNA molecule. In any of the preceding embodiments, the target nucleic acid can be an mRNA.

In any of the preceding embodiments, the target nucleic acid can be in a tissue sample, and the region of interest can be analyzed in situ in the tissue sample.

In any of the preceding embodiments, the tissue sample can be an intact tissue sample or a non-homogenized tissue sample.

In any of the preceding embodiments, the target nucleic acid can be in a biological particle, e.g., a cell in the tissue sample. In any of the preceding embodiments, the method can further comprise permeabilizing the cell before, during, or after the contacting step.

In any of the preceding embodiments, the tissue sample can be a tissue section.

In any of the preceding embodiments, the tissue sample can be a fixed tissue sample, e.g., a formalin-fixed, paraffin-embedded (FFPE) sample, a frozen tissue sample, or a fresh tissue sample.

In any of the preceding embodiments, the region of interest can be 3' in the target nucleic acid relative to the HR1'. In any of the preceding embodiments, hybridization region HR2' can comprise the region of interest. In any of the preceding embodiments, hybridization region HR3' can comprise the region of interest.

In any of the preceding embodiments, hybridization region HR2' can comprise a first region of interest and hybridization region HR3' can comprise a second region of interest. In some of any such embodiments, the region of interest comprises a polymorphism (e.g., a single nucleotide of interest).

In any of the preceding embodiments, hybridization region HR1' can be between about 15 and about 35 nucleotides in length.

In any of the preceding embodiments, hybridization region HR1' can be between about 20 and about 25 nucleotides in length.

In any of the preceding embodiments, hybridization region HR2' and/or HR3' can be between about 3 and about 20 nucleotides in length. In any of the preceding embodiments, hybridization region HR2' and/or HR3' can be between about 5 and about 10 nucleotides or between about 10 and about 15 nucleotides in length.

In any of the preceding embodiments, the circular or padlock probe can be a circular probe.

In any of the preceding embodiments, the circular or padlock probe can be a padlock probe. In any of the preceding embodiments, the method can further comprise ligating the padlock probe, optionally preceded by gap filling, to form a circular probe.

In any of the preceding embodiments, hybridization region HRa can be a split region, and ligating the padlock probe can comprise using hybridization region HRb as a splint.

In any of the preceding embodiments, hybridization region HRa can be not a split region.

In any of the preceding embodiments, hybridization region HR1 can be a split region, and ligating the padlock probe can comprise using hybridization region HR1' as a splint.

In any of the preceding embodiments, hybridization region HR1 can be not a split region.

In any of the preceding embodiments, the circular or padlock probe can comprise a barcode sequence that identifies a nucleic acid sequence.

In any of the preceding embodiments, the barcode sequence can identify the region of interest. In any of the preceding embodiments, the barcode sequence can identify the polymorphism. In any of the preceding embodiments, the barcode sequence can identify the single nucleotide of interest.

In any of the preceding embodiments, the circular or padlock probe can comprise one or more other barcode sequences. In any of the preceding embodiments, the target nucleic acid can be an mRNA and one of the one or more other barcode sequences can identify the mRNA as a splice variant and/or can identify a splice junction sequence.

In any of the preceding embodiments, the barcode sequences can be between about 8 and about 16 nucleotides in length. In any of the preceding embodiments, the barcode sequences can be between about 8 and about 10 nucleotides in length.

In any of the preceding embodiments, hybridization region HRa can be between about 3 and about 10 nucleotides in length.

In any of the preceding embodiments, hybridization region HRa can comprise an identifying sequence that identifies the region of interest. In any of the preceding embodiments, the identifying sequence can be about 4 nucleotides in length.

In any of the preceding embodiments, the circular or padlock probe can be a DNA molecule.

In any of the preceding embodiments, the primer can be between about 8 and about 25 nucleotides in length.

In any of the preceding embodiments, hybridization region HRb can be between about 3 and about 10 nucleotides in length.

In any of the preceding embodiments, hybridization region HR2 can be between about 5 and about 15 nucleotides in length.

In any of the preceding embodiments, hybridization region HR2 can be between about 5 and about 10 nucleotides in length.

In any of the preceding embodiments, hybridization region HR2 can be between about 10 and about 15 nucleotides in length.

In any of the preceding embodiments, the primer can be a DNA molecule.

In any of the preceding embodiments, the at least one nucleotide complementary to the region of interest can be internal in hybridization region HR2. In any of the preceding embodiments, the at least single nucleotide complementary to the single nucleotide of interest can be internal in hybridization region HR2.

In any of the preceding embodiments, the at least one nucleotide complementary to the region of interest can be at the 5' end of the primer. In any of the preceding embodiments, the nucleotide complementary to the single nucleotide of interest can be at the 5' end of the primer.

In any of the preceding embodiments, the anchor can be between about 8 and about 25 nucleotides in length.

In any of the preceding embodiments, the anchor can be between about 5 and about 15 nucleotides in length.

In any of the preceding embodiments, hybridization region HR3 can be between about 5 and about 10 nucleotides in length.

In any of the preceding embodiments, the anchor can be a DNA molecule.

In any of the preceding embodiments, the at least one nucleotide complementary to the region of interest can be internal in hybridization region HR3. In any of the preceding embodiments, the nucleotide complementary to the single nucleotide of interest can be internal in hybridization region HR3.

In any of the preceding embodiments, the at least one nucleotide complementary to the region of interest can be at the 3' end of the anchor. In any of the preceding embodiments, the nucleotide complementary to the single nucleotide of interest can be at the 3' end of the anchor.

In any of the preceding embodiments, the ligation can comprise enzymatic ligation, chemical ligation, template dependent ligation, and/or template independent ligation.

In any of the preceding embodiments, the enzymatic ligation can utilize a ligase.

In any of the preceding embodiments, the ligase can be a T4 RNA ligase, a splintR ligase, a single stranded DNA ligase, or a T4 DNA ligase.

In any of the preceding embodiments, the ligase can have an RNA-splinted DNA ligase activity.

In any of the preceding embodiments, the hybridization complex can be formed under conditions permissive for specific hybridization of the primer and the anchor to the target nucleic acid, whereas when the primer or anchor does not comprise the at least one nucleotide complementary to the region of interest (e.g., single nucleotide of interest), it does not specifically hybridize to the target nucleic acid under the conditions.

In any of the preceding embodiments, the hybridization complex can be formed under conditions permissive for specific hybridization of the primer to the target nucleic acid, whereas when the primer does not comprise the at least one nucleotide complementary to the region of interest (e.g., single nucleotide of interest), it does not specifically hybridize to the target nucleic acid under the conditions.

In any of the preceding embodiments, the hybridization complex can be formed under conditions permissive for specific hybridization of the circular or padlock probe to the target nucleic acid.

In any of the preceding embodiments, the hybridization complex can be formed at a temperature below the melting temperature ($T_m$) of the primer for hybridization to the target nucleic acid and the circular or padlock probe, wherein the temperature is above the $T_m$ of the primer when it does not comprise the at least one nucleotide complementary to the region of interest (e.g., single nucleotide of interest) for hybridization to the target nucleic acid and the circular or padlock probe.

In any of the preceding embodiments, the hybridization complex can be formed at a temperature below the melting temperature ($T_m$) of the primer for hybridization to the target nucleic acid, wherein the temperature is above the $T_m$ of the primer when it does not comprise the at least one nucleotide complementary to the region of interest (e.g., single nucleotide of interest) for hybridization to the target nucleic acid.

In any of the preceding embodiments, the method can further comprise a step of removing molecules that are not specifically hybridized in the hybridization complex, e.g., the primer or anchor when it does not comprise the at least one nucleotide complementary to the region of interest (e.g., single nucleotide of interest).

In any of the preceding embodiments, the ligation to form the ligated anchor-primer can be performed under conditions permissive for specific hybridization of the primer and the anchor to the target nucleic acid, whereas when the primer or anchor does not comprise the at least one nucleotide complementary to the region of interest (e.g., single nucleotide of interest), it does not specifically hybridize to the target nucleic acid under the conditions.

In any of the preceding embodiments, the ligation to form the ligated anchor-primer can be performed under conditions permissive for specific hybridization of the primer to the target nucleic acid, whereas when the primer does not comprise the at least one nucleotide complementary to the region of interest (e.g., single nucleotide of interest), it does not specifically hybridize to the target nucleic acid under the conditions.

In any of the preceding embodiments, the ligation to form the ligated anchor-primer can be performed under conditions permissive for specific hybridization of the circular or padlock probe to the target nucleic acid.

In any of the preceding embodiments, the ligation to form the ligated anchor-primer can be performed at a temperature below the melting temperature ($T_m$) of the primer for hybridization to the target nucleic acid and the circular or padlock probe, wherein the temperature is above the $T_m$ of the primer when it does not comprise the at least one nucleotide complementary to the region of interest (e.g., single nucleotide of interest) for hybridization to the target nucleic acid and the circular or padlock probe.

In any of the preceding embodiments, the ligation to form the ligated anchor-primer can be performed at a temperature below the melting temperature ($T_m$) of the primer for hybridization to the target nucleic acid, wherein the temperature is above the $T_m$ of the primer when it does not comprise the at least one nucleotide complementary to the region of interest (e.g., single nucleotide of interest) for hybridization to the target nucleic acid.

In any of the preceding embodiments, the $T_m$ of the primer for hybridization to the target nucleic acid and the circular or padlock probe and/or the $T_m$ of the primer for hybridization to the target nucleic acid can be between about 10° C. and about 30° C.

In any of the preceding embodiments, the $T_m$ of the ligated anchor-primer for hybridization to the target nucleic acid and the circular or padlock probe and/or the $T_m$ of the ligated anchor-primer for hybridization to the target nucleic acid can be between about 40° C. and about 70° C.

In any of the preceding embodiments, the $T_m$ of the ligated anchor-primer can be between about 1.1-fold and about 5-fold of the $T_m$ of the primer for hybridization to the target nucleic acid and the circular or padlock probe and/or for hybridization to the target nucleic acid.

In any of the preceding embodiments, the method can further comprise a step of removing molecules that are not specifically hybridized to the target nucleic acid and/or the circular probe after the ligation, e.g., the primer or anchor when it does not comprise the at least one nucleotide complementary to the region of interest (e.g., single nucleotide of interest).

In any of the preceding embodiments, the removing step can comprise a wash.

In any of the preceding embodiments, the wash can be a stringency wash.

In any of the preceding embodiments, the ligated anchor-primer can remain specifically hybridized to the circular probe while non-ligated primer molecules and/or anchor molecules are removed.

In any of the preceding embodiments, the amplification product can be formed using isothermal amplification or non-isothermal amplification.

In any of the preceding embodiments, the amplification product can be formed using rolling circle amplification (RCA).

In any of the preceding embodiments, the RCA can comprise a linear RCA, a branched RCA, a dendritic RCA, or any combination thereof.

In any of the preceding embodiments, the amplification product can be formed using a Phi29 polymerase.

In any of the preceding embodiments, the amplification can be performed at a temperature lower than the melting temperature ($T_m$) of the ligated anchor-primer for hybridization to the target nucleic acid and the circular probe or a circular probe formed from the padlock probe, and higher than the $T_m$ of the primer for hybridization to the target nucleic acid and the circular probe or the circular probe formed from the padlock probe.

In any of the preceding embodiments, the amplification can be performed at a temperature lower than the melting temperature ($T_m$) of the ligated anchor-primer for hybridization to the target nucleic acid and higher than the $T_m$ of the primer for hybridization to the target nucleic acid.

In any of the preceding embodiments, the amplification can be performed at a temperature between about 20° C. and about 60° C.

In any of the preceding embodiments, the amplification can be performed at a temperature between about 30° C. and about 40° C.

In any of the preceding embodiments, the $T_m$ of the ligated anchor-primer for hybridization to the target nucleic acid can be between about 1.1-fold and about 3-fold of the amplification temperature.

In any of the preceding embodiments, the detecting of the amplification product can comprise sequencing all or a portion of the amplification product and/or in situ hybridization to the amplification product.

In any of the preceding embodiments, the sequencing can comprise sequencing hybridization, sequencing by ligation, and/or fluorescent in situ sequencing.

In any of the preceding embodiments, the in situ hybridization can comprise sequential fluorescent in situ hybridization.

In any of the preceding embodiments, the detecting of the amplification product can comprise labeling the amplification product (e.g., directly or indirectly) with a fluorophore, an isotope, a mass tag, or a combination thereof.

In any of the preceding embodiments, the detecting of the amplification product can comprise imaging the amplification product.

In any of the preceding embodiments, the target nucleic acid can be an mRNA in a tissue sample, and the detecting of the amplification product can be performed when the target nucleic acid and/or the amplification product is in situ in the tissue sample.

In any of such embodiments, the region of interest may comprise a single nucleotide of interest. In some of any such embodiments, the region of interest may comprise a polymorphism. In any of the preceding embodiments, the single nucleotide of interest or polymorphism can be selected from the group consisting of a single-nucleotide polymorphism (SNP), a single-nucleotide variant (SNV), a single-nucleotide substitution, a point mutation, a single-nucleotide insertion, and a single-nucleotide deletion. In any of the preceding embodiments, the single nucleotide of interest can be a SNP.

In any of the preceding embodiments, the single nucleotide of interest can be in HR2', and the nucleotide complementary to the single nucleotide of interest can be between about 15 nucleotides and about 1 nucleotide from the 5' end of the primer.

In any of the preceding embodiments, the nucleotide complementary to the single nucleotide of interest can be between about 10 nucleotides and about 5 nucleotides from the 5' end of the primer.

In any of the preceding embodiments, the nucleotide complementary to the single nucleotide of interest can be the 5' end nucleotide of the primer.

In some embodiments, provided herein is a kit, comprising (a) a circular or padlock probe, (b) a primer, and (c) an anchor, wherein: (1) the circular or padlock probe (a) comprises adjacent hybridization regions HR1 and HRa, the primer (b) comprises adjacent hybridization regions HRb and HR2, and the anchor (c) comprises hybridization region HR3, wherein HRa is capable of hybridizing to HRb; (2) (a) the circular or padlock probe, (b) the primer, and (c) the anchor are capable of hybridizing to a target nucleic acid comprising adjacent hybridization regions HR1', HR2', and HR3', wherein HR1, HR2, and HR3 are capable of hybridizing to HR1', HR2', and HR3', respectively; and (3) the 3' end of the anchor and the 5' end of the primer are directly juxtaposed to each other upon hybridization to the target nucleic acid.

In any of the preceding embodiments, the kit can further comprise the target nucleic acid.

In any of the preceding embodiments, the circular or padlock probe can circular.

In any of the preceding embodiments, the target nucleic acid can be an mRNA, and the circular or padlock probe, the primer, and the anchor can be DNA molecules.

In any of the preceding embodiments, the kit can further comprise a ligase having an RNA-splinted DNA ligase activity.

In any of the preceding embodiments, the 3' end of the anchor and the 5' end of the primer can be capable of being ligated, optionally preceded by gap filling, to form a ligated anchor-primer capable of hybridizing to the target nucleic acid.

In any of the preceding embodiments, the kit can further comprise a polymerase capable of using the ligated anchor-primer as a primer and the circular probe or a circular probe formed from the padlock probe as a template to form a rolling circle amplification product.

In some embodiments provided herein is a composition, comprising a complex comprising (a) a target nucleic acid, (b) a circular or padlock probe, (c) a primer, and (d) an anchor, wherein: (1) the circular or padlock probe (b) comprises adjacent hybridization regions HR1 and HRa, the primer (b) comprises adjacent hybridization regions HRb and HR2, the anchor (c) comprises hybridization region HR3, and the target nucleic acid comprises adjacent hybridization regions HR1', HR2', and HR3'; and (2) HR1 hybridizes to HR1', HRa hybridizes to HRb, and HR2 and HR3 hybridize to HR2' and HR3', respectively, thereby hybridizing the circular or padlock probe, the primer, and the anchor to the target nucleic acid and directly juxtaposing the 3' end of the anchor and the 5' end of the primer.

In some embodiments, provided herein is a composition, comprising a complex comprising (a) a target nucleic acid, (b) a circular or padlock probe, and (c) a ligated anchor-primer comprising an anchor portion and a primer portion, wherein: (1) the circular or padlock probe (b) comprises adjacent hybridization regions HR1 and HRa, the primer portion of (c) comprises adjacent hybridization regions HRb and HR2, the anchor portion of (c) comprises hybridization region HR3, and the target nucleic acid comprises adjacent hybridization regions HR1', HR2', and HR3'; and (2) HR1 hybridizes to HR1', HRa hybridizes to HRb, and HR2 and HR3 hybridize to HR2' and HR3', respectively, thereby hybridizing the circular or padlock probe and the anchor-primer to the target nucleic acid.

In some embodiments, provided herein is a composition, comprising an amplification product comprising an anchor portion, a primer portion, and monomeric units of a sequence complementary to a sequence of a circular or padlock probe, wherein: (1) the circular or padlock probe comprises adjacent hybridization regions HR1 and HRa, the primer portion comprises adjacent hybridization regions HRb and HR2, and the anchor portion comprises hybridization region HR3, wherein HRa is capable of hybridizing to HRb; and (2) the circular or padlock probe, the primer portion, and the anchor portion are capable of hybridizing to a target nucleic acid comprising adjacent hybridization regions HR1', HR2', and HR3', wherein HR1, HR2, and HR3 are capable of hybridizing to HR1', HR2', and HR3', respectively, and the 3' end of the anchor and the 5' end of the primer are directly juxtaposed to each other upon hybridization to the target nucleic acid.

In any of the preceding embodiments, the composition can further comprise a sequence of the target nucleic acid hybridized to the amplification product.

In any of the preceding embodiments, the amplification product can be a rolling circle amplification product.

In any of the preceding embodiments, the amplification product can form a DNA nanoball.

In any of the preceding embodiments, HR2' can comprise a region of interest and HR2 can comprise at least one nucleotide complementary to the region of interest. In any of the preceding embodiments, HR2' can comprise a single nucleotide of interest and HR2 can comprise a nucleotide complementary to the single nucleotide of interest.

In any of the preceding embodiments, the single nucleotide of interest can be selected from the group consisting of a single-nucleotide polymorphism (SNP), a single-nucleotide variant (SNV), a single-nucleotide substitution, a point mutation, a single-nucleotide insertion, and a single-nucleotide deletion.

In some embodiments, provided herein is a method for analyzing a single nucleotide of interest in a target mRNA, the method comprising: (i) contacting (a) a target mRNA with (b) a single-stranded circular probe, (c) a primer, and (d) an anchor to form a hybridization complex, wherein the circular probe, the primer, and the anchor are DNA molecules, and wherein: (1) the circular probe comprises adjacent hybridization regions HR1 and HRa, the primer comprises adjacent hybridization regions HRb and HR2, the anchor comprises hybridization region HR3, and the target mRNA comprises adjacent hybridization regions HR1', HR2', and HR3', wherein HR2' comprises a single nucleotide of interest, and (2) HR1 hybridizes to HR1', HRa hybridizes to HRb, HR2 comprises a nucleotide complementary to the single nucleotide of interest and is between 5 and 15 nucleotides in length, and HR2 and HR3 hybridize to HR2' and HR3', respectively, thereby hybridizing the circular probe, the primer, and the anchor to the target mRNA and directly juxtaposing the 3' end of the anchor and the 5' end of the primer; (ii) ligating the 3' end of the anchor and the 5' end of the primer to form a ligated anchor-primer, using a ligase having an RNA-splinted DNA ligase activity and the target mRNA as a template; (iii) forming a rolling circle amplification product using the circular probe as a template and the ligated anchor-primer as a primer; and (iv) determining a sequence in the rolling circle amplification product indicative of the single nucleotide of interest.

In some embodiments, provided herein is a method for analyzing a single-nucleotide polymorphism (SNP) in a target mRNA, the method comprising: (i) contacting (a) a permeabilized tissue sample comprising a target mRNA with a (b) single-stranded circular probe, (c) a primer, and (d) an anchor to form a hybridization complex, wherein the single-stranded circular probe, the primer, and the anchor are DNA molecules, and wherein: (1) the single-stranded circular probe comprises adjacent hybridization regions HR1 and HRa, the primer comprises adjacent hybridization regions HRb and HR2, the anchor comprises hybridization region HR3, and the target mRNA comprises adjacent hybridization regions HR1', HR2', and HR3', wherein HR2' comprises a SNP, (2) HR1 hybridizes to HR1', HRa hybridizes to HRb, HR2 comprises a nucleotide complementary to the SNP nucleotide and is between 5 and 15 nucleotides in length, and HR2 and HR3 hybridize to HR2' and HR3', respectively, thereby hybridizing the single-stranded circular probe, the primer, and the anchor to the target mRNA and directly juxtaposing the 3' end of the anchor and the 5' end of the primer, and (3) the single-stranded circular probe comprises a barcode sequence indicative of the SNP nucleotide; (ii) ligating the 3' end of the anchor and the 5' end of the primer to form a ligated anchor-primer, using a ligase having an RNA-splinted DNA ligase activity and the target mRNA as a template; (iii) removing molecules that are not specifically hybridized to the target mRNA and/or the single-stranded circular probe; (iv) forming a rolling circle amplification product in situ in the permeabilized tissue sample, using the single-stranded circular probe as a template and the ligated anchor-primer as a primer, at a temperature lower than the melting temperature ($T_m$) of the ligated anchor-primer for hybridization to the target mRNA and higher than the $T_m$ of the primer for hybridization to the target mRNA; and (v) determining the sequence of an amplicon in the rolling circle amplification product in situ in the permeabilized tissue sample, wherein the amplicon comprises the barcode sequence indicative of the SNP nucleotide.

In some embodiments, the present application provides a method for analyzing a single nucleotide of interest in a target mRNA, the method comprising: (i) contacting (a) a target mRNA with (b) a primer and (c) an anchor, wherein the primer comprises adjacent hybridization regions HRb and HR2, the anchor comprises hybridization region HR3, and the target mRNA comprises adjacent hybridization regions HR1', HR2', and HR3', wherein HR2' comprises a single nucleotide of interest and HR2 comprises a nucleotide complementary to the single nucleotide of interest and is between 5 and 15 nucleotides in length, and HR2 and HR3 hybridize to HR2' and HR3', respectively, thereby hybridizing the primer and the anchor to the target mRNA and directly juxtaposing the 3' end of the anchor and the 5' end of the primer; (ii) ligating the 3' end of the anchor and the 5' end of the primer to form a ligated anchor-primer hybridized to the target mRNA, using a ligase having an RNA-splinted DNA ligase activity and the target mRNA as a template, at a temperature below the melting temperature ($T_m$) of the primer for hybridization to the target mRNA, wherein the temperature is above the $T_m$ of the primer for hybridization to the target mRNA when the primer does not comprise the nucleotide complementary to the single nucleotide of interest; (iii) removing molecules that are not specifically hybridized to the target mRNA; (iv) contacting the ligated anchor-primer hybridized to the target mRNA with a padlock probe comprising adjacent hybridization regions HR1 and HRa, wherein HR1 hybridizes to HR1' in the target mRNA and HRa hybridizes to HRb in the primer, wherein the padlock probe is circularized to form a circular probe; (v) forming a rolling circle amplification product using the circular probe as a template and the ligated anchor-primer as a primer; and (vi) determining a sequence in the rolling circle amplification product indicative of the single nucleotide of interest.

In some embodiments, provided herein is a method for analyzing a single-nucleotide polymorphism (SNP) in a target mRNA, the method comprising: (i) contacting (a) a permeabilized tissue sample comprising a target mRNA with (b) a primer and (c) an anchor, wherein the primer comprises adjacent hybridization regions HRb and HR2, the anchor comprises hybridization region HR3, and the target mRNA comprises adjacent hybridization regions HR1', HR2', and HR3', wherein HR2' comprises a SNP nucleotide and HR2 comprises a nucleotide complementary to the SNP nucleotide and is between 5 and 15 nucleotides in length, and HR2 and HR3 hybridize to HR2' and HR3', respectively, thereby hybridizing the primer and the anchor to the target mRNA and directly juxtaposing the 3' end of the anchor and the 5' end of the primer; (ii) ligating the 3' end of the anchor and the 5' end of the primer to form a ligated anchor-primer hybridized to the target mRNA, using a ligase having an RNA-splinted DNA ligase activity and the target mRNA as a template, at a temperature below the melting temperature ($T_m$) of the primer for hybridization to the target mRNA, wherein the temperature is above the $T_m$ of the primer for hybridization to the target mRNA when the primer does not comprise the nucleotide complementary to the single nucleotide of interest; (iii) removing molecules that are not specifically hybridized to the target mRNA; (iv) contacting the ligated anchor-primer hybridized to the target mRNA with a padlock probe comprising adjacent hybridization regions HR1 and HRa, wherein HR1 hybridizes to HR1' in the target mRNA and HRa hybridizes to HRb in the primer, (1) wherein the padlock probe comprises a barcode sequence indicative of the SNP nucleotide, and (2) wherein the padlock probe is circularized to form a circular probe; (v) forming a rolling circle amplification product in situ in the permeabilized tissue sample, using the circular probe as a template and the ligated anchor-primer as a primer; and (vi) determining the sequence of an amplicon in the rolling circle amplification product in situ in the permeabilized tissue sample, wherein the amplicon comprises the barcode sequence indicative of the SNP nucleotide.

BRIEF DESCRIPTION OF THE DRAWINGS

In FIG. 1, the single nucleotide of interest is contained in hybridization region HR2' of the target nucleic acid.

In FIG. 2, the single nucleotide of interest is contained in hybridization region HR3' of the target nucleic acid.

In FIG. 3, the target nucleic acid comprises two single nucleotides of interest, one contained in hybridization region HR2' and the other contained in hybridization region HR3'.

In FIG. 4, the single nucleotide of interest is contained in hybridization region HR2' of the target nucleic acid, and hybridization region HRa of the padlock probe is a split hybridization region.

In FIG. 5, the single nucleotide of interest is contained in hybridization region HR2' of the target nucleic acid, and hybridization region HR1 of the padlock probe is a split hybridization region.

DETAILED DESCRIPTION

Figure 1:
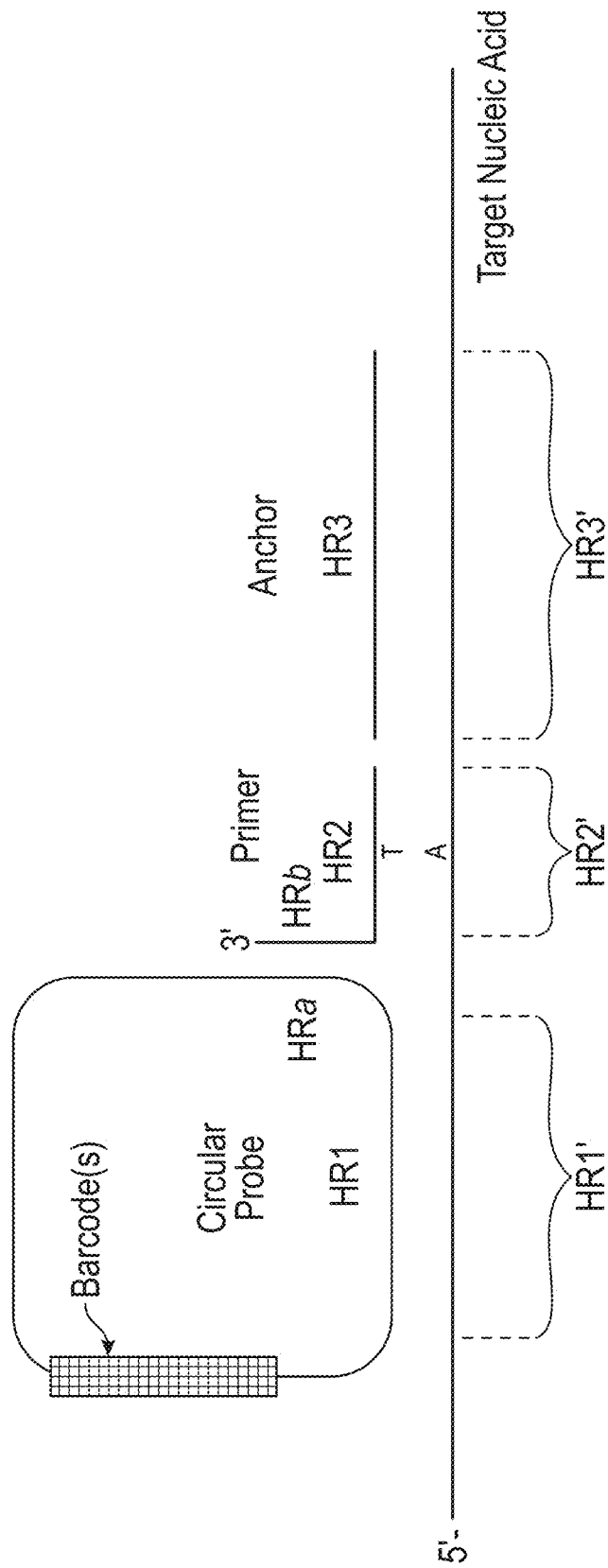
FIG. 1 depicts exemplary probe polynucleotides, comprising a circular probe, a primer, and an anchor, for use in analyzing a region of interest (e.g., a sequence of 5 nucleotides or shorter such as a single nucleotide of interest) in a target nucleic acid in a biological sample.

The practice of the techniques described herein may employ, unless otherwise indicated, conventional techniques and descriptions of organic chemistry, polymer technology, molecular biology (comprising recombinant techniques), cell biology, biochemistry, and sequencing technology, which are within the skill of those who practice in the art. Such conventional techniques comprise polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), DNA *Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), Molecular Cloning: A Laboratory Manual (all from Cold Spring Harbor Laboratory Press); Stryer, L. (1995) *Biochemistry* (4th Ed.) W. H. Freeman, New York N.Y.; Gait, "*Oligonucleotide Synthesis: A Practical Approach*" 1984, IRL Press, London; Nelson and Cox (2000), Lehninger, *Principles of Biochemistry* 3rd Ed., W. H. Freeman Pub., New York, N.Y.; and Berg et al. (2002) *Biochemistry*, $5^{th}$ Ed., W. H. Freeman Pub., New York, N.Y., all of which are herein incorporated in their entirety by reference for all purposes.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

Provided herein are methods involving the use of a set of polynucleotides for analyzing one or more target nucleic acid(s), such as a target nucleic acid (for example, a messenger RNA) present in a biological particle (e.g., a cell or nucleus) or a biological sample, such as a tissue sample. Also provided are polynucleotides, sets of polynucleotides, compositions, kits, systems and devices for use in accordance with the provided methods. In some aspects, the provided methods can be applied to detect, image, quantitate, or determine the sequence of one or more target nucleic acid(s), comprising sequence variants such as point mutations and SNPs.

In some aspects, the provided embodiments can be employed for in situ detection and/or sequencing of a target nucleic acid in a cell, e.g., in cells of a biological sample or a sample derived from a biological sample, such as a tissue section on a solid support, such as on a transparent slide.

In some aspects, provided herein are in situ assays using microscopy as a readout, e.g., nucleic acid sequencing, hybridization, or other sequence detection or determination methods involving an optical readout. In some aspects, detection or determination of a sequence of one, two, three, four, five, or more nucleotides of a target nucleic acid is performed in situ in a cell in an intact tissue. In some embodiments, a method for spatially profiling analytes such as the transcriptome or a subset thereof in a biological sample is provided. Methods, compositions, kits, devices, and systems for these in situ assays, comprising spatial genomics and transcriptomics assays, are provided. In some embodiments, a provided method is quantitative and preserves the spatial information within a tissue sample without physically isolating cells or using homogenates.

In some embodiments, through the use of various probe designs (e.g., various padlock/circular probe, anchor, and/or primer oligos), the present disclosure provides methods for high-throughput profiling one or more regions of interest (e.g., comprising one or more single nucleotides of interest, any two of which may be contiguous or separated by one or more nucleotides) in a large number of targets in situ, such as transcripts and/or DNA loci, for detecting and/or quantifying nucleic acids in cells, tissues, organs or organisms. In some embodiments, an exemplary advantage of the provided methods includes the ability to assess specific nucleic acids by designing the probe oligonucleotides (e.g., primer, anchor, etc.) of the system to be meta-stable such that subsequent steps such as ligation and amplification is dependent upon the recognition of the target nucleic acid of interest (e.g., a SNP in the target nucleic acid). For example, the subsequent amplification of the circular probe or a circularized probe formed from a padlock probe is dependent on whether one or more ligation event(s) occurs (e.g., ligation of the primer to the anchor). In some aspects, the provided methods allow for a targeted detection method (e.g., a region of interest or a single nucleotide of interest in a polymorphic locus).

In some aspects, the methods disclosed herein involve the use of one or more probes or probe sets that hybridize to a target nucleic acid, such as an RNA molecule. Exemplary probes or probe sets may be based on a padlock probe, a gapped padlock probe, a SNAIL probe set, a PLAYR (Proximity Ligation Assay for RNA) probe set, a PLISH (Proximity Ligation in situ Hybridization) probe set, and RNA-templated ligation probes. For example, a probe set can be modified in design to include use of a meta-stable primer (in some instances also referred to as a priming probe) and/or a meta-stable anchor. The specific probe or probe set design can vary. In some embodiments, a primary probe (e.g., a DNA probe that directly binds to an RNA target) is amplified through rolling circle amplification. In some embodiments, the primary probes, such as a padlock probe or a probe set that comprises a padlock probe, contain one or more barcodes. In some embodiments, one or more barcodes are indicative of a sequence in the target nucleic acid, such as a region of interest or a single nucleotide of interest (e.g., SNPs or point mutations), a dinucleotide sequence, or a short sequence of about 5 nucleotides in length.

In some aspects, the provided methods involve analyzing, e.g., detecting or determining, one or more sequences present in the polynucleotides and/or in an amplification product, such as in an amplification product of a circular probe or circularized padlock probe which comprises one or more barcode sequences. In some embodiments, the analysis comprises detecting the presence or absence of the amplification product. In some embodiments, the analysis comprises determining the sequence of all or a portion of the amplification product. In some embodiments, the analysis comprises detecting a sequence present in the amplification product. In some embodiments, the sequence of all or a portion of the amplification product is indicative of the identity of a region of interest (e.g., a region comprising one or more single nucleotides of interest, any two of which may be contiguous or separated by one or more nucleotides) in a target nucleic acid. In some embodiments, the sequence of all or a portion of the amplification product is indicative of the identity of a polymorphism of interest in a target nucleic acid. In some embodiments, the sequence of all or a portion of the amplification product is indicative of the identity of a single nucleotide of interest in a target nucleic acid. In some embodiments, due to amplification of one or more polynucleotides (e.g., a circular probe or circularized padlock probe), particular sequences present in the amplification product or complementary sequences thereof can be detected even when a polynucleotide is present at low levels before the amplification. For example, the number of copies of the barcode sequence(s) and/or a complementary sequence thereof is increased by virtue of the amplification of a probe comprising the barcode sequence(s) and/or complementary sequence thereof, thereby enabling specific and sensitive detection of a signal indicative of the identity of a region of interest (e.g., single nucleotide of interest) in a target nucleic acid. In particular embodiments, the amplification product is an in situ rolling circle amplification (RCA) product of a circular probe.

In some embodiments, the methods involve the use of a set of polynucleotides, such as a set of three or more polynucleotides. In some aspects, the set of polynucleotides comprises three polynucleotides (e.g., a circular or padlock probe, a primer, and an anchor) for analyzing a target nucleic acid. In some aspects, the set of polynucleotides comprises four or more polynucleotides, e.g., one or more circular or padlock probes, one or more primers, and one or more anchors. In some aspects, the polynucleotides (e.g., the set of three or more polynucleotides) contain hybridization regions (HRs) that hybridize to target sites in the target nucleic acids (e.g., mRNA in a cell), and also HRs that hybridize to one or more other polynucleotides in the set of polynucleotides. In some aspects, one or more polynucleotides of the set of polynucleotides are amplified. In some aspects, the provided methods can be applied for various applications, comprising for in situ analysis, comprising in situ detection (e.g., based on hybridization such as sequential hybridization) and/or sequencing of target nucleic acids and multiplexed nucleic acid analysis. In some aspects, the provided methods can be for in situ detection and/or identification of a region of interest (e.g., single nucleotide of interest) in target nucleic acids.

In some embodiments, provided herein are methods for assessing one or more target nucleic acids, such as a plurality of different mRNAs, in a biological sample, such as a cell or a tissue sample (such as a tissue section). In some aspects, the provided methods are employed for in situ analysis of target nucleic acids, for example for in situ sequencing or multiplexed analysis in intact tissues or a sample with preserved cellular or tissue structure. In some aspects, the provided methods can be used to detect or determine the identity, abundance, level, or amount in situ of regions of interest (e.g., single nucleotides of interest) in target nucleic acids, for instance of single nucleotide polymorphisms of genes of interest.

In some aspects, the provided methods involve a step of contacting, or hybridizing, one or more polynucleotides, such as a circular or padlock probe, a primer, and an anchor, to a cell or a sample containing a target nucleic acid with a region of interest (e.g., single nucleotide of interest) in order to form a hybridization complex. In some aspects, the provided methods comprise one or more steps of ligating the polynucleotides, for instance of ligating the anchor and the primer to form a ligated anchor-primer and/or the ends of the padlock probe to form a circularized probe. In some aspects, the provided methods involve a step of amplifying one of the polynucleotides (e.g., a circular probe or a circularized probe produced from a padlock probe), to generate an amplification product. In some aspects, the provided methods involve a step of detecting and/or determining the sequence of all or a portion of the amplification product (for example, of one or more barcodes contained in the amplification product) and/or one or more of the polynucleotides with or without amplification, for instance any barcodes contained therein. In some aspects, the provided methods involve performing one or more of the steps described herein, simultaneously and/or sequentially.

In some embodiments, the provided methods involve one or more steps of contacting a target nucleic acid comprising a region of interest (e.g., single nucleotide of interest) with a circular or padlock probe, a primer, and an anchor to form a hybridization complex; ligating the anchor to the primer to form a ligated anchor-primer; optionally ligating and thereby circularizing the padlock probe to form a circularized probe; forming an amplification product using the circular probe or circularized probe as a template and the ligated anchor-primer as a primer; and/or detecting the amplification product, wherein the detection is indicative of the presence or identity of the region of interest (e.g., single nucleotide of interest). Particulars of the steps of the methods can be carried out as described herein, for example in Sections II-VI; and/or using any suitable processes and methods for carrying out the particular steps.

II. Target Nucleic Acids, Samples, and Sample Processing

Target nucleic acid molecules can be derived from or analyzed in any specific type of cell and/or a specific sub-cellular region, e.g., from cytosol, from cell nuclei, from mitochondria, from microsomes, and more generally, from any other compartment, organelle, or portion of a cell. Examples comprise DNA analytes such as genomic DNA, methylated DNA, specific methylated DNA sequences, fragmented DNA, mitochondrial DNA, and RNA/DNA hybrids. In some embodiments, a method disclosed herein may comprise a step for increasing accessibility of a nucleic acid for binding, e.g., a denaturation step to open up DNA in a cell for hybridization by a probe. For example, proteinase K treatment may be used to free up DNA with proteins bound thereto.

Examples of target nucleic acid molecules also comprise RNA analytes such as various types of coding and non-coding RNA. Examples of the different types of RNA analytes comprise messenger RNA (mRNA), ribosomal RNA (rRNA), transfer RNA (tRNA), microRNA (miRNA), pre-mRNA, and viral RNA. RNA analytes can be obtained from cells or cellular compartments (e.g., nucleus). The RNA can be a transcript (e.g., present in a tissue section). The RNA can be small (e.g., less than 200 nucleic acid bases in length) or large (e.g., RNA greater than 200 nucleic acid bases in length). Small RNAs mainly comprise 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some embodiments, a target nucleic acid molecule comprises a polymorphic locus, e.g., a location in the nucleotide sequence of the alleles of a gene of a diploid organism that may be occupied by different nucleotides. The difference may be the result of a SNP, a point mutation, a nucleotide insertion, or a nucleotide deletion. In some embodiments, a target nucleic acid molecule comprises a SNP, e.g., a polynucleotide that differs from another polynucleotide at a particular locus by virtue of a single nucleotide exchange. A polynucleotide may contain numerous SNPs each occurring at a different locus. For example, exchanging one A for one C, G or T at a particular locus in the sequence of a polynucleotide constitutes a SNP. SNPs can occur in coding and non-coding regions of a gene, and may be in DNA or an RNA, such as an mRNA transcript. Those in coding regions are of primary interest because such SNPs can cause changes in the phenotype, i.e., a detectable physical difference in an individual compared to the general population. Detectable physical differences comprise, without limitation, a difference in susceptibility to a particular disease or disorder or a difference in response to a therapeutic regime used to treat or prevent a disease or disorder. In some embodiments, a target nucleic acid molecule comprises a point mutation, e.g., a change at a single locus in a polynucleotide strand. The change may be the deletion of a nucleotide, the addition of a nucleotide or the substitution of one nucleotide for another. In some embodiments, a target nucleic acid molecule may include a DNA locus that is a non-coding region.

In some embodiments, a sequence or region of interest in a target nucleic acid molecule is one nucleotide (e.g., a SNP or point mutation), two nucleotides (e.g., CpG and GpC dinucleotides), three nucleotides, four nucleotides, five nucleotides, or longer. In some embodiments, the sequence or region of interest is 5 or fewer, 4 or fewer, 3 or fewer, or 2 or fewer nucleotides in length.

In some aspects, the provided methods are used to analyze target nucleic acids present in a sample or a specimen, such as in a cell or a tissue sample. In some examples, the sample or specimen is deposited on a surface. In some aspects, the target nucleic acids are present in a sample or a specimen among a plurality of different nucleic acids. In some aspects, the sample is a biological sample, is derived from a biological sample, or is a biological sample that was subject to various processes or manipulations. In some aspects, the provided methods also involve processing or manipulating the sample, for instance before any hybridization, ligation, amplification, and/or detection steps. In some aspects, such processing or manipulating facilitates the analysis of the target nucleic acids. In some aspects, such processing or manipulating preserves the spatial information of the target nucleic acid within the sample or specimen.

In some aspects, the provided methods are used to analyze target nucleic acids in an intact tissue or non-homogenized tissue. In some embodiments, the target nucleic acid is in a cell in the tissue. Tissue specimens suitable for use with the methods described herein comprise any type of tissue specimens collected from living or dead subjects, such as, e.g., biopsy specimens and autopsy specimens, of which comprise, but are not limited to, epithelium, muscle, connective, and nervous tissue. Tissue specimens may be collected and processed using the methods described herein and subjected to microscopic analysis immediately following processing, or may be preserved and subjected to microscopic analysis at a future time, e.g., after storage for an extended period of time. In some embodiments, the methods described herein may be used to preserve tissue specimens in a stable, accessible, and fully intact form for future analysis. In some embodiments, the methods described herein may be used to analyze a previously-preserved or stored tissue specimen. In some embodiments, the intact tissue comprises brain tissue such as visual cortex slices. In some embodiments, the intact tissue is a thin slice with a thickness of 5-20 μm, comprising, but not limited to, e.g., 5-18 μm, 5-15 μm, or 5-10 μm. In some embodiments, the intact tissue is a thick slice with a thickness of 50-200 μm, comprising, but not limited to, e.g., 50-150 μm, 50-100 μm, or 50-80 μm.

A variety of steps can be performed to prepare or process a biological sample for and/or during analysis. Except where indicated otherwise, the preparative or processing steps described below can generally be combined in any manner and in any order to appropriately prepare or process a particular sample for and/or analysis.

A. Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 micrometers thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 11, 12, 13, 14, 15, 20, 30, 40, or 50 micrometers. Thicker sections can also be used if desired or convenient, e.g., at least 70, 80, 90, or 100 micrometers or more. Typically, the thickness of a tissue section is between 1-100 micrometers, 1-50 micrometers, 1-30 micrometers, 1-25 micrometers, 1-20 micrometers, 1-15 micrometers, 1-10 micrometers, 2-8 micrometers, 3-7 micrometers, or 4-6 micrometers, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

B. Freezing

In some embodiments, the biological sample (e.g., a tissue section as described above) can be prepared by deep freezing at a temperature suitable to maintain or preserve the integrity (e.g., the physical characteristics) of the tissue structure. Such a temperature can be, e.g., less than −20° C., or less than −25° C., −30° C., −40° C., −50° C., −60° C., −70° C., −80° C. −90° C., −100° C., −110° C., −120° C., −130° C., −140° C., −150° C., −160° C., −170° C., −180° C., −190° C., or −200° C. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

C. Formalin Fixation and Paraffin Embedding

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

D. Fixation

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-TRITON™, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some aspects, the methods comprise fixing an intact tissue. In some aspects, the methods are performed on fixed intact tissue. Generally, fixing or fixation involves preserving biological material (e.g., tissues, cells, organelles, molecules, etc.) from decay and/or degradation. Fixation may be accomplished using any convenient protocol. Fixation can comprise contacting the sample with a fixation reagent (i.e., a reagent that contains at least one fixative). Samples can be contacted by a fixation reagent for a wide range of times, which can depend on the temperature, the nature of the sample, and on the fixative(s). For example, a sample can be contacted by a fixation reagent for 24 or less hours, 18 or less hours, 12 or less hours, 8 or less hours, 6 or less hours, 4 or less hours, 2 or less hours, 60 or less minutes, 45 or less minutes, 30 or less minutes, 25 or less minutes, 20 or less minutes, 15 or less minutes, 10 or less minutes, 5 or less minutes, or 2 or less minutes.

A sample can be contacted by a fixation reagent at various temperatures, depending on the protocol and the reagent used. For example, in some instances a sample can be contacted by a fixation reagent at a temperature ranging from −22° C. to 55° C., where specific ranges of interest comprise, but are not limited to 50 to 54° C., 40 to 44° C., 35 to 39° C., 28 to 32° C., 20 to 26° C., 0 to 6° C., and −18 to −22° C. In some instances, a sample can be contacted by a fixation reagent at a temperature of −20° C., 4° C., room temperature (22-25° C.), 30° C., 37° C., 42° C., or 52° C.

Any convenient fixation reagent can be used. Common fixation reagents comprise crosslinking fixatives, precipitating fixatives, oxidizing fixatives, mercurials, and the like. Crosslinking fixatives chemically join two or more molecules by a covalent bond and a wide range of cross-linking reagents can be used. Examples of suitable cross liking fixatives comprise but are not limited to aldehydes (e.g., formaldehyde, also commonly referred to as "paraformaldehyde" and "formalin"; glutaraldehyde; etc.), imidoesters, NHS (N-Hydroxysuccinimide) esters, and the like. Examples of suitable precipitating fixatives comprise but are not limited to alcohols (e.g., methanol, ethanol, etc.), acetone, acetic acid, etc. In some embodiments, the fixative is formaldehyde (i.e., paraformaldehyde or formalin). A suitable final concentration of formaldehyde in a fixation reagent is 0.1 to 10%, 1-8%, 1-4%, 1-2%, 3-5%, or 3.5-4.5%, comprising about 1.6% for 10 minutes. In some embodiments the sample is fixed in a final concentration of 4% formaldehyde (as diluted from a more concentrated stock solution, e.g., 38%, 37%, 36%, 20%, 18%, 16%, 14%, 10%, 8%, 6%, etc.). In some embodiments the sample is fixed in a final concentration of 10% formaldehyde. In some embodiments the sample is fixed in a final concentration of 1% formaldehyde. In some embodiments, the fixative is glutaraldehyde. A suitable concentration of glutaraldehyde in a fixation reagent is 0.1 to 1%. A fixation reagent can contain more than one fixative in any combination. For example, in some embodiments the sample is contacted with a fixation reagent containing both formaldehyde and glutaraldehyde. In addition to the fixation methods described, tissue may be paraffin-embedded (FFPE), a frozen, or processed fresh.

In some embodiments, the methods provided herein comprises one or more post-fixing (also referred to as postfixation) steps. In some embodiments, one or more post-fixing step is performed after contacting a sample with a polynucleotide disclosed herein, e.g., one or more of the polynucleotides disclosed in Section III, such as an anchor, a meta-stable primer, and/or a circular or padlock probe. In some embodiments, one or more post-fixing step is performed after a hybridization complex (e.g., as disclosed in Section III) is formed in a sample. In some embodiments, one or more post-fixing step is performed prior to a ligation reaction disclosed herein, e.g., as disclosed in Section IV.

In some embodiments, one or more post-fixing step is performed after contacting a sample with a labelling agent (e.g., an antibody or antigen binding fragment thereof) for a non-nucleic acid analyte such as a protein analyte. The labelling agent can comprise a nucleic acid molecule (e.g., a reporter oligonucleotide) comprising a sequence corresponding to the labelling agent and therefore corresponds to (e.g., uniquely identifies) the protein analyte. In some embodiments, the labelling agent can comprise a nucleic acid molecule (e.g., reporter oligonucleotide) comprising one or more barcode sequences.

A post-fixing step may be performed using any suitable fixation reagent disclosed herein, for example, 3% (w/v) paraformaldehyde in DEPC-PBS.

E. Tissue Permeabilization

In some embodiments, a biological sample can be permeabilized to facilitate transfer of analytes out of the sample, and/or to facilitate transfer of species (such as probes) into the sample. If a sample is not permeabilized sufficiently, the amount of analyte available for analysis may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, TRITON X-100™ or TWEEN-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., *Method Mol. Biol.* 588:63-66, 2010, the entire contents of which are incorporated herein by reference. Any suitable method for sample permeabilization can generally be used in connection with the samples described herein.

In some embodiments, where a diffusion-resistant medium is used to limit migration of analytes or other species during the analytical procedure, the diffusion-resistant medium can include at least one permeabilization reagent. For example, the diffusion-resistant medium can include wells (e.g., micro-, nano-, or picowells) containing a permeabilization buffer or reagents. In some embodiments, where the diffusion-resistant medium is a hydrogel, the hydrogel can include a permeabilization buffer. In some embodiments, the hydrogel is soaked in permeabilization buffer prior to contacting the hydrogel with a sample. In some embodiments, the hydrogel or other diffusion-resistant medium can contain dried reagents or monomers to deliver permeabilization reagents when the diffusion-resistant medium is applied to a biological sample. In some embodiments, the diffusion-resistant medium, (i.e. hydrogel) is covalently attached to a solid substrate (i.e. an acrylated glass slide).

In some embodiments, permeabilization solution can be delivered to a sample through a porous membrane. In some embodiments, a porous membrane is used to limit diffusive analyte losses, while allowing permeabilization reagents to reach a sample. Membrane chemistry and pore size can be manipulated to minimize analyte loss. In some embodiments, the porous membrane may be made of glass, silicon, paper, hydrogel, polymer monoliths, or other material. In some embodiments, the material may be naturally porous. In some embodiments, the material may have pores or wells etched into solid material. In some embodiments, the permeabilization reagents are flowed through a microfluidic chamber or channel over the porous membrane. In some embodiments, the flow controls the sample's access to the permeabilization reagents. In some embodiments, a porous membrane is sandwiched between a spatially-barcoded array and the sample, wherein permeabilization solution is applied over the porous membrane. The permeabilization reagents diffuse through the pores of the membrane and into the tissue.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Non-chemical permeabilization methods are known in the art. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

In some aspects, the methods provided herein comprise permeabilizing the tissue. In some embodiments, the methods are performed using permeabilized tissue. In some aspects, permeabilization comprises a process of rendering the cells (cell membranes etc.) of a sample permeable to experimental reagents such as nucleic acid probes, antibodies, chemical substrates, etc. Any convenient method and/or reagent for permeabilization can be used. Suitable permeabilization reagents comprise detergents (e.g., Saponin, TRITON X-100™, TWEEN-20™, etc.), organic fixatives (e.g., acetone, methanol, ethanol, etc.), enzymes, etc. Detergents can be used at a range of concentrations. For example, 0.001%-1% detergent, 0.05%-0.5% detergent, or 0.1%-0.3% detergent can be used for permeabilization (e.g., 0.1% Saponin, 0.2% TWEEN-20™, 0.1-0.3% TRITON X-100™, etc.). In some embodiments, methanol on ice for at least 10 minutes is used to permeabilize.

In some embodiments, a sample can be contacted by a permeabilization reagent for a wide range of times, which can depend on the temperature, the nature of the sample, and on the permeabilization reagent(s). For example, a sample can be contacted by a permeabilization reagent for 24 or more hours, 24 hours or less, 18 hours or less, 12 hours or less, 8 hours or less, 6 hours or less, 4 hours or less, 2 hours or less, 60 minutes or less, 45 minutes or less, 30 minutes or less, 25 minutes or less, 20 minutes or less, 15 minutes or less, 10 minutes or less, 5 minutes or less, or 2 minutes or less. In some embodiments, a sample can be contacted by a permeabilization reagent at various temperatures, depending on the protocol and the reagent used. For example, in some instances a sample can be contacted by a permeabilization reagent at a temperature ranging from −82° C. to 55° C., where specific ranges of interest comprise, but are not limited to: 50 to 54° C., 40 to 44° C., 35 to 39° C., 28 to 32° C., 20 to 26° C., 0 to 6° C., −18 to −22° C., and −78 to −82° C. In some instances a sample can be contacted by a permeabilization reagent at a temperature of −80° C., −20° C., 4° C., room temperature (in some examples, less than 30° C., or 22-25° C.), 30° C., 37° C., 42° C., or 52° C.

In some embodiments, a sample is contacted with an enzymatic permeabilization reagent. Enzymatic permeabilization reagents that permeabilize a sample by partially degrading extracellular matrix or surface proteins that hinder the permeation of the sample by assay reagents. Contact with an enzymatic permeabilization reagent can take place at any point after fixation and prior to target detection. In some instances, the enzymatic permeabilization reagent is proteinase K, a commercially available enzyme. In some cases, permeabilization is performed prior to providing the probe polynucleotides (e.g., the circular or padlock probe, primer, and anchor) to the sample.

In such cases, the sample is contacted with proteinase K prior to contact with a post fixation reagent. Proteinase K treatment (i.e., contact by proteinase K; also commonly referred to as "proteinase K digestion") can be performed over a range of times at a range of temperatures, over a range of enzyme concentrations that are empirically determined for each cell type or tissue type under investigation. For example, a sample can be contacted by proteinase K for 30 minutes or less, 25 minutes or less, 20 minutes or less, 15 minutes or less, 10 minutes or less, 5 minutes or less, or 2 minutes or less. A sample can be contacted by 1 pg/ml or less, 2 pg/ml or less, 4 pg/ml or less, 8 pg/ml or less, 10 pg/ml or less, 20 pg/ml or less, 30 pg/ml or less, 50 pg/ml or less, or 100 pg/ml or less proteinase K. In some embodiments, a sample can be contacted by proteinase K at a temperature ranging from 2° C. to 55° C., where specific ranges of interest comprise, but are not limited to: 50 to 54° C., 40 to 44° C., 35 to 39° C., 28 to 32° C., 20 to 26° C., and 0 to 6° C. In some instances, a sample can be contacted by proteinase K at a temperature of 4° C., room temperature (in some examples, less than 30° C., or 22-25° C.), 30° C., 37° C., 42° C., or 52° C. In some embodiments, a sample is not contacted with an enzymatic permeabilization reagent. In some embodiments, a sample is not contacted with proteinase K. In some aspects, contact of an intact tissue with at least a fixation reagent and a permeabilization reagent results in the production of a fixed and permeabilized tissue.

F. Embedding

As an alternative to paraffin embedding described above, a biological sample can be embedded in any of a variety of other embedding materials to provide structural substrate to the sample prior to sectioning and other handling steps. In general, the embedding material is removed prior to analysis of tissue sections obtained from the sample. Suitable embedding materials include, but are not limited to, waxes, resins (e.g., methacrylate resins), epoxies, and agar.

In some embodiments, the biological sample can be embedded in a hydrogel matrix. Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other hydrogel-formation method known in the art.

In some embodiments, a method disclosed herein comprises de-crosslinking a reversibly cross-linked biological sample. The de-crosslinking does not need to be complete. In some embodiments, only a portion of crosslinked molecules in the reversibly cross-linked biological sample are de-crosslinked.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 m to about 2 mm.

Additional methods and aspects of hydrogel embedding of biological samples are described for example in Chen et al., *Science* 347(6221):543-548, 2015, the entire contents of which are incorporated herein by reference.

In some embodiments, the methods disclosed comprise embedding the sample in a matrix-forming material, e.g., in a manner to substantially retain the relative three-dimensional spatial relationship of a plurality of nucleic acids in the sample. In some embodiments, the methods disclosed comprise making a three dimensional matrix of nucleic acids. In some embodiments, nucleic acids are covalently bound into a matrix or into or to a matrix material. The nucleic acids may be co-polymerized with the matrix material or cross-linked to the matrix material or both. According to one aspect, a plurality of nucleic acid sequences of certain length, such as DNA or RNA sequences are part of a three-dimensional copolymer. The nucleic acids may then be amplified and detected and/or analyzed (e.g., sequenced) in situ, i.e. within the matrix. The three-dimensional matrix of nucleic acids provides, in a certain aspect, an information storage medium where the nucleic acids, i.e. a sequence of one or more nucleotides, represent stored information which can be read within the three-dimensional matrix. Matrix forming materials may comprise polyacrylamide, cellulose, alginate, polyamide, cross-linked agarose, cross-linked dextran, cross-linked polyethylene glycol, disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin, e.g., as described in U.S. Pat. No. 10,138,509, herein specifically incorporated by reference. The matrix forming materials can form a matrix by polymerization and/or cross-linking of the matrix forming materials using methods specific for the matrix forming materials and known methods, reagents and conditions.

In some aspects, the matrix is sufficiently optically transparent or otherwise has optical properties suitable for detection, imaging and/or sequencing, for example, as described herein and/or using standard high-throughput sequencing chemistries and deep three dimensional imaging for high throughput information readout. Exemplary high-throughput sequencing chemistries that utilize fluorescence imaging comprise ABI SoLiD (Life Technologies), in which a sequencing primer on a template is ligated to a library of fluorescently labeled nonamers with a cleavable terminator. After ligation, the beads are then imaged using four color channels (FITC, Cy3, Texas Red and Cy5). The terminator is then cleaved off leaving a free-end to engage in the next ligation-extension cycle. After all dinucleotide combinations have been determined, the images are mapped to the color code space to determine the specific base calls per template. The workflow is achieved using an automated fluidics and imaging device (i.e., SoLiD 5500 W Genome Analyzer, ABI Life Technologies). Another sequencing platform uses sequencing by synthesis, in which a pool of single nucleotide with a cleavable terminator is incorporated using DNA polymerase. After imaging, the terminator is cleaved and the cycle is repeated. The fluorescence images are then analyzed to call bases for each DNA amplicons within the flow cell (HiSeq, Illumina).

In some embodiments, the methods disclosed comprise preparing a biological tissue specimen for microscopic analysis, e.g., a process that maintains the 3-D integrity of the tissue by embedding it in a hydrogel, and making molecules of interest accessible for optical probing and molecular labeling while allowing undesired molecules such as lipids to be washed away. See Chung et al., "CLARITY for mapping the nervous system," *Nature Methods* 10 (2013) and U.S. Pat. No. 10,545,075, herein specifically incorporated by reference. In some embodiments, the methods disclosed herein comprise fixing a biological tissue specimen obtained from a mammal by contacting the biological tissue specimen with a fixation agent and a plurality of hydrogel subunits, thereby cross-linking the hydrogel subunits to biomolecules within the biological tissue specimen to produce biomolecule-bound hydrogel subunits. In some embodiments, the methods further comprise polymerizing the biomolecule-bound hydrogel subunits to form a hydrogel-embedded biological tissue specimen. In some embodiments, the methods further comprise electrophoresing the hydrogel-embedded biological tissue specimen to remove a plurality of cellular components from the specimen and form a cleared hydrogel-embedded biological tissue specimen.

In some embodiments, the methods disclosed comprise embedding the sample in a hydrogel. The hydrogel-tissue chemistry described comprises covalently attaching nucleic acids to in situ synthesized hydrogel for tissue clearing, enzyme diffusion, and multiple-cycle sequencing. In some embodiments, a hydrogel or hydrogel network comprises a network of polymer chains that are water-insoluble, sometimes found as a colloidal gel in which water is the dispersion medium. In other words, hydrogels are a class of polymeric materials that can absorb large amounts of water without dissolving. Hydrogels can contain over 99% water and may comprise natural or synthetic polymers, or a combination thereof.

Hydrogels also possess a degree of flexibility very similar to natural tissue, due to their significant water content. A detailed description of suitable hydrogels may be found in published U.S. Patent Application 20100055733, herein specifically incorporated by reference. As used herein, the terms "hydrogel subunits" or "hydrogel precursors" mean hydrophilic monomers, prepolymers, or polymers that can be crosslinked, or "polymerized", to form a three-dimensional (3D) hydrogel network. Without being bound by any scientific theory, it is believed that this fixation of the biological specimen in the presence of hydrogel subunits crosslinks the components of the specimen to the hydrogel subunits, thereby securing molecular components in place, preserving the tissue architecture and cell morphology.

In some embodiments, the embedding comprises copolymerizing the one or more amplicons with acrylamide, for example, to form a copolymer which contains more than one type of subunit. A copolymer encompasses polymers which comprise two, three, four, five, or six types of subunits.

G. Staining and Immunohistochemistry (IHC)

To facilitate visualization, biological samples can be stained using a wide variety of stains and staining techniques. In some embodiments, for example, a sample can be stained using any number of stains, and/or immunohistochemical reagents. One or more staining steps may be performed to prepare or process a biological sample for an assay described herein or may be performed during and/or after an assay. In some embodiments, the sample can be contacted with one or more nucleic acid stains, membrane stains (e.g., cellular or nuclear membrane), cytological stains, or combinations thereof. In some examples, the stain may be specific to proteins, phospholipids, DNA (e.g., dsDNA, ssDNA), RNA, an organelle or compartment of the cell. The sample may be contacted with one or more labeled antibodies (e.g., a primary antibody specific for the analyte of interest and a labeled secondary antibody specific for the primary antibody). In some embodiments, cells in the sample can be segmented using one or more images taken of the stained sample.

In some embodiments, the stain is performed using a lipophilic dye. In some examples, the staining is performed with a lipophilic carbocyanine or aminostyryl dye, or analogs thereof (e.g, DiI, DiO, DiR, DiD). Other cell membrane stains may include FM and RH dyes or immunohistochemical reagents specific for cell membrane proteins. In some examples, the stain may include but is not limited to, acridine orange, acid fuchsin, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, ruthenium red, propidium iodide, rhodamine (e.g., rhodamine B), or safranine, or derivatives thereof. In some embodiments, the sample may be stained with haematoxylin and eosin (H&E).

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain. The sample can also be subjected to staining of cell nuclei, such as by fluorescent dyes including DAPI, Hoechst 33258, olivomycin, and/or acriflavin and/or nonfluorescent staining.

In some embodiments, biological samples can be destained. Methods of destaining or discoloring a biological sample are known in the art, and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

H. Isometric Expansion

In some embodiments, a biological sample embedded in a hydrogel can be isometrically expanded. Isometric expansion methods that can be used include hydration, a preparative step in expansion microscopy, as described in Chen et al., *Science* 347(6221):543-548, 2015.

Isometric expansion can be performed by anchoring one or more components of a biological sample to a gel, followed by gel formation, proteolysis, and swelling. Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, MA), Label-IT Amine (available from MirusBio, Madison, WI) and Label X (described for example in Chen et al., *Nat. Methods* 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

I. Substrate Attachment

In general, a substrate can be used to provide support to a biological sample, particularly, for example, a thin tissue section. Accordingly, a "substrate" is a support that is insoluble in aqueous liquid and which allows for positioning of biological samples, analytes, features, and/or probes on the substrate.

A wide variety of different substrates can be used for the foregoing purposes. In general, a substrate can be any suitable support material. Exemplary substrates include, but are not limited to, glass, modified and/or functionalized glass, hydrogels, films, membranes, plastics (including e.g., acrylics, polystyrene, copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene and polycarbonate.

The substrate can also correspond to a flow cell. Flow cells can be formed of any of the foregoing materials, and can include channels that permit reagents, solvents, features, and molecules to pass through the cell.

Among the examples of substrate materials discussed above, polystyrene is a hydrophobic material suitable for binding negatively charged macromolecules because it normally contains few hydrophilic groups. For nucleic acids immobilized on glass slides, by increasing the hydrophobicity of the glass surface the nucleic acid immobilization can be increased. Such an enhancement can permit a relatively more densely packed formation (e.g., provide improved specificity and resolution).

In some embodiments, a substrate is coated with a surface treatment such as poly(L)-lysine. Additionally or alternatively, the substrate can be treated by silanation, e.g. with epoxy-silane, amino-silane, and/or by a treatment with poly-acrylamide.

III. Polynucleotides and Hybridization Complexes

A. Target Nucleic Acid

In some aspects, a target nucleic acid disclosed herein comprises any polynucleotide nucleic acid molecule (e.g., DNA molecule; RNA molecule, modified nucleic acid, etc.) for assessment in accordance with the provided embodiments, such as a polynucleotide present in a cell. In some embodiments, a plurality of target nucleic acids is analyzed using the provided methods. In some embodiments, the target nucleic acid is a coding RNA (e.g., mRNA). The target may, in some embodiments, be a single RNA molecule. In other embodiments, the target may be at least one RNA molecule, e.g., a group of 2, 3, 4, 5, 6 or more RNA molecules. These RNA molecules may differ in molecule type, and/or may differ in sequence. In some embodiments, the target nucleic acid is, for example, a non-coding RNA (e.g., tRNA, rRNA, microRNA (miRNA), mature miRNA or immature miRNA). In some embodiments, the target nucleic acid is a splice variant of an RNA molecule (e.g., mRNA, pre-mRNA, etc.) in the context of a cell. A suitable target nucleic acid can therefore be an unspliced RNA (e.g., pre-mRNA, mRNA), a partially spliced RNA, or a fully spliced RNA, etc. Target nucleic acids of interest may be variably expressed, i.e., have a differing abundance, within a cell population, wherein the methods of the invention allow profiling and comparison of the expression levels of nucleic acids, comprising but not limited to, RNA transcripts, in individual cells. A target nucleic acid can also be a DNA molecule, e.g., a denatured genomic, viral, plasmid, etc. For example, the methods can be used to detect copy number variants, e.g., in a cancer cell population in which a target nucleic acid is present at different abundance in the genome of cells in the population; a virus-infected cells to determine the virus load and kinetics, and the like.

In some aspects, the methods provided herein are used to analyze a target nucleic acid, e.g., a messenger RNA molecule. In some embodiments, the target nucleic acid is present in a cell in a tissue, for instance in a tissue sample or tissue section. In some embodiments, the tissue sample is an intact tissue sample or a non-homogenized tissue sample. In some embodiments, the tissue sample is a fresh tissue sample. In some embodiments, the tissue has previously been processed, e.g., fixed, embedded, frozen, or permeabilized using any of the steps and/or protocols described in Section II.

In some embodiments, the target nucleic acid may comprise a region of interest. In some embodiments, a region of interest may include any region of sequence comprising at least one nucleic acid of interest. In some embodiments, the region of interest comprises a polymorphism. For example, the polymorphism may comprise one or more base changes, an insertion, a repeat, a deletion, a frame shift, an alternatively spliced sequence(s), or any combinations thereof. In some embodiments, the one or more base changes may be contiguous or separated from one another by one or more nucleotides. In some cases, a polymorphic locus may be as small as one base pair e.g., a single nucleotide of interest.

In some embodiments, the target nucleic acid comprises one or more hybridization regions (HRs). Exemplary HRs are depicted in FIGS. 1-5 and are labelled as HR1', HR2', and HR3'. The HRs refer to regions that are complementary or sufficiently complementary to a different nucleic acid sequence (for example, to another HR present in one or more of the probe polynucleotides) to form complexes via, e.g., Watson-Crick base pairing. In some embodiments, the target nucleic acid comprises two adjacent HRs. In some embodiments, the two HRs are immediately adjacent to one another. In other embodiments, the two HRs are separated by a gap, for instance a gap of 1, 2, 3, 4, or 5 nucleotides.

In some embodiments, the provided HRs may refer to a region or a sequence that comprises at least one complementary nucleotide(s) complementary to the region of interest. In some example, the HR may comprise at least one nucleotide complementary to the region of interest, wherein the region of interest comprises a polymorphism. In some cases, the HR may comprise nucleotides in addition to the at least one nucleotide that is complementary to the region of interest. In some aspects, the HR comprises a nucleotide complementary to the SNP nucleotide comprised in the region of interest. In some embodiments, any of the HRs contained in the target nucleic acid are between or between about 5 and 40 nucleotides in length. In some embodiments, the HR are between or between about 5 and 15 nucleotides in length. In some embodiments, the HR are between or between about 15 and 20 nucleotides in length. In some embodiments, the HR are between or between about 20 and 25 nucleotides in length. In some embodiments, the HR are between or between about 25 and 30 nucleotides in length. In some embodiments, the HR are between or between about 30 and 35 nucleotides in length. In some embodiments, the HR are between or between about 25 and 30 nucleotides in length. In some embodiments, the HR are between or between about 35 and 40 nucleotides in length.

In some embodiments, the HR containing the region of interest (e.g., single nucleotide of interest) is between or between about 5 and 40 nucleotides in length. In some embodiments, the HR containing the region of interest (e.g., single nucleotide of interest) is between or between about 5 and 15 nucleotides in length. In some embodiments, the HR containing the region of interest (e.g., single nucleotide of interest) is between or between about 15 and 20 nucleotides in length. In some embodiments, the HR containing the region of interest (e.g., single nucleotide of interest) is between or between about 20 and 25 nucleotides in length. In some embodiments, the HR containing the region of interest (e.g., single nucleotide of interest) is between or between about 25 and 30 nucleotides in length. In some embodiments, the HR containing the region of interest (e.g., single nucleotide of interest) is between or between about 30 and 35 nucleotides in length. In some embodiments, the HR containing the region of interest (e.g., single nucleotide of interest) is between or between about 25 and 30 nucleotides in length. In some embodiments, the HR containing the region of interest (e.g., single nucleotide of interest) is between or between about 35 and 40 nucleotides in length.

In some embodiments, the single nucleotide of interest is at one of the five terminal nucleotide positions of the HR. In some embodiments, the single nucleotide of interest is at the fifth terminal nucleotide position of the HR. In some embodiments, the single nucleotide of interest is at the fourth terminal nucleotide position of the HR. In some embodiments, the single nucleotide of interest is at the third terminal nucleotide position of the HR. In some embodiments, the single nucleotide of interest is at the second terminal nucleotide position of the HR. In some embodiments, the single nucleotide of interest is at the terminus of the HR. In some embodiments, the single nucleotide of interest is the 5' end nucleotide of the HR, e.g., HR3'. In other embodiments, the single nucleotide of interest is the 3' end nucleotide of the HR, e.g., HR2'.

In some embodiments, the single nucleotide of interest is the 5' end nucleotide of HR3' and is immediately adjacent to the 3' end nucleotide of HR2' contained in the target nucleic acid. In other embodiments, the single nucleotide of interest is the 3' end nucleotide of HR2' and is immediately adjacent to the 5' end nucleotide of HR3' contained in the target nucleic acid.

B. Probe Oligos and Oligo Sets

In accordance with the provided embodiments, the probe polynucleotides (e.g., the circular or padlock probe, primer, and anchor) also comprise HRs and are designed to permit hybridization to HRs contained in other probe polynucleotides and/or in the target nucleic acid. In some aspects, probe polynucleotides (e.g., the circular or padlock probe, primer, and anchor) may be provided at the same time, or each of the probe polynucleotides may be provided sequentially. In some cases, one or more optional wash steps can be performed between providing one or more of the probe polynucleotides. In some aspects, the probe polynucleotides for use in the methods provided herein are designed to form a hybridization complex, for instance one containing the target nucleic acid and each of the probe polynucleotides. In some aspects, the probe polynucleotides are designed such that ligation and/or amplification of one or more probe polynucleotides is dependent on the identity of the region of interest (e.g., a single nucleotide of interest). In some aspects, such design permits the analysis, e.g., detection or identification, of the region of interest (e.g., single nucleotide of interest) or the analysis, e.g., detection or sequencing, of a sequence indicative of the identity of the region of interest (e.g., single nucleotide of interest). In some embodiments, a plurality of padlock probes, splints, and anchors can be used to target a various nucleotide(s) of interests (e.g., various SNPs or SNP locations).

In some aspects, one or more of the probe polynucleotides comprise one or more barcodes. In some aspects, one or more barcodes are comprised in the amplified polynucleotide (e.g., present in the padlock probe). In some embodiments, one or more barcode are on a probe polynucleotide that is not amplified (e.g., the anchor) and can provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of the region of interest (e.g., single nucleotide of interest).

In some embodiments, one or more of the barcodes disclosed herein can be correlated with the sequence complementary to the analyte, and thus a particular analyte (e.g., target nucleic acid of interest, region of interest, or single nucleotide of interest). A number (n) of analytes can be examined by introducing (n) different sequences complementary to an analyte/barcode pluralities to the sample. In some embodiments, sequences complementary to an analyte can be used in multiplexed methods to analyze 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, or more analytes.

In some embodiments, methods provided herein comprise analyzing the one or more barcodes of the probe polynucleotides using multiplexed spatial imaging. In some embodiments, analyzing the barcode of the amplicons comprises employing exemplary barcode detection schemes such as described in RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), in situ sequencing, targeted in situ sequencing, fluorescent in situ sequencing (FISSEQ), or spatially-resolved transcript amplicon readout mapping (STARmap). In some embodiments, the methods provided herein comprise analyzing the barcode of the composite padlock or circular probes by sequential hybridization and detection with a plurality of labelled probes. A variety of light-based sequencing technologies are known in the art. See, e.g., Landegren et al., Genome Res. 8:769-76 (1998); Kwok, Pharmocogenomics 1:95-100 (2000); and Shi, Clin. Chem. 47:164-172 (2001).

In some aspects, the barcode provides information for identification of the target nucleic acid and/or one or more single nucleotides of interest contained therein. In some aspects, the term "barcode" refers a label, or identifier, that conveys or is capable of conveying information (e.g., information about a target nucleic acid in a sample or a molecule such as a probe polynucleotide), such as a nucleic acid sequence that is used to identify, e.g., a single cell or a subpopulation of cells or a single target nucleic acid or a subset of target nucleic acids. Barcodes can be linked to a target nucleic acid of interest, region of interest, or single nucleotide of interest during amplification and used to trace back the amplicon to, for example, the cell and/or position in a tissue from which the target nucleic acid originated. A barcode can be added to a target nucleic acid of interest during amplification by carrying out amplification with a polynucleotide that contains a region comprising the barcode and a region that is complementary to the target nucleic acid such that the barcode is incorporated into the final amplified target nucleic acid product (i.e., amplicon). A particular barcode can be unique relative to other barcodes. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can comprise a unique molecular identifier or "UMI").

In some embodiments, the barcode sequences comprise $4^N$ complexity given a sequencing read of N bases, and a much shorter sequencing read may be required for molecular identification by non-barcode sequencing methods such as direct sequencing of an RNA target or a cDNA. For example, 1024 molecular species may be identified using a 5-nucleotide barcode sequence ($4^5=1024$), whereas 8 nucleotide barcodes can be used to identify up to 65,536 molecular species, a number greater than the total number of distinct genes in the human genome. In some embodiments, the barcode sequences contained in the probes are detected, rather than endogenous sequences, which can be an efficient read-out in terms of information per cycle of sequencing. Because the barcode sequences are pre-determined, they can also be designed to feature error detection and correction mechanisms.

In some aspects, one or more of the probe polynucleotides comprise one or more barcodes. In some aspects, at least two, three, four, five, six, seven, eight, nine, 10, or more barcodes are comprised in the padlock or circular probe formed of the plurality of polynucleotides.

Barcodes can spatially-resolve molecular components found in biological samples, for example, within a cell or a tissue sample. In some embodiments, a barcode comprises two or more sub-barcodes or partial barcodes that together function as a single barcode. For example, a polynucleotide barcode can comprise two or more polynucleotide sequences (e.g., sub-barcodes) that are separated by one or more non-barcode sequences.

In some embodiments, the provided probe polynucleotides comprise one or more primary barcode sequences. In some embodiments, an amplification product (e.g., an RCA product) comprises multiple copies of the one or more primary barcode sequences or complementary sequences thereof, and the amplification product is detected using one or more detection probes (e.g., a detectably labeled oligo such as fluorescent oligonucleotides) that hybridize to the one or more primary barcode sequences or complementary sequences thereof.

In some embodiments, the method further comprises using one or more secondary probes that hybridize to the one or more primary barcode sequences or complementary sequences thereof on one or more primary probes (e.g., one or more of the primer, anchor, and circular/padlock probes disclosed herein) that bind to a target nucleic acid such as an mRNA. In some embodiments, the one or more secondary probes hybridize to an amplification product (e.g., an RCA product) comprising multiple copies of the one or more primary barcode sequences or complementary sequences thereof. In some embodiments, the one or more secondary probes comprise one or more secondary barcode sequences and are detected using one or more detection probes (e.g., a detectably labeled oligo such as fluorescent oligonucleotides) that hybridize to the one or more second barcode sequences or complementary sequences thereof.

In any of the embodiments, barcodes (e.g., primary and/or secondary barcode sequences) can be analyzed (e.g., detected or sequenced) using any suitable methods or techniques, comprising those described herein, for example, in Section VI.

1. Anchor

Figure 8:
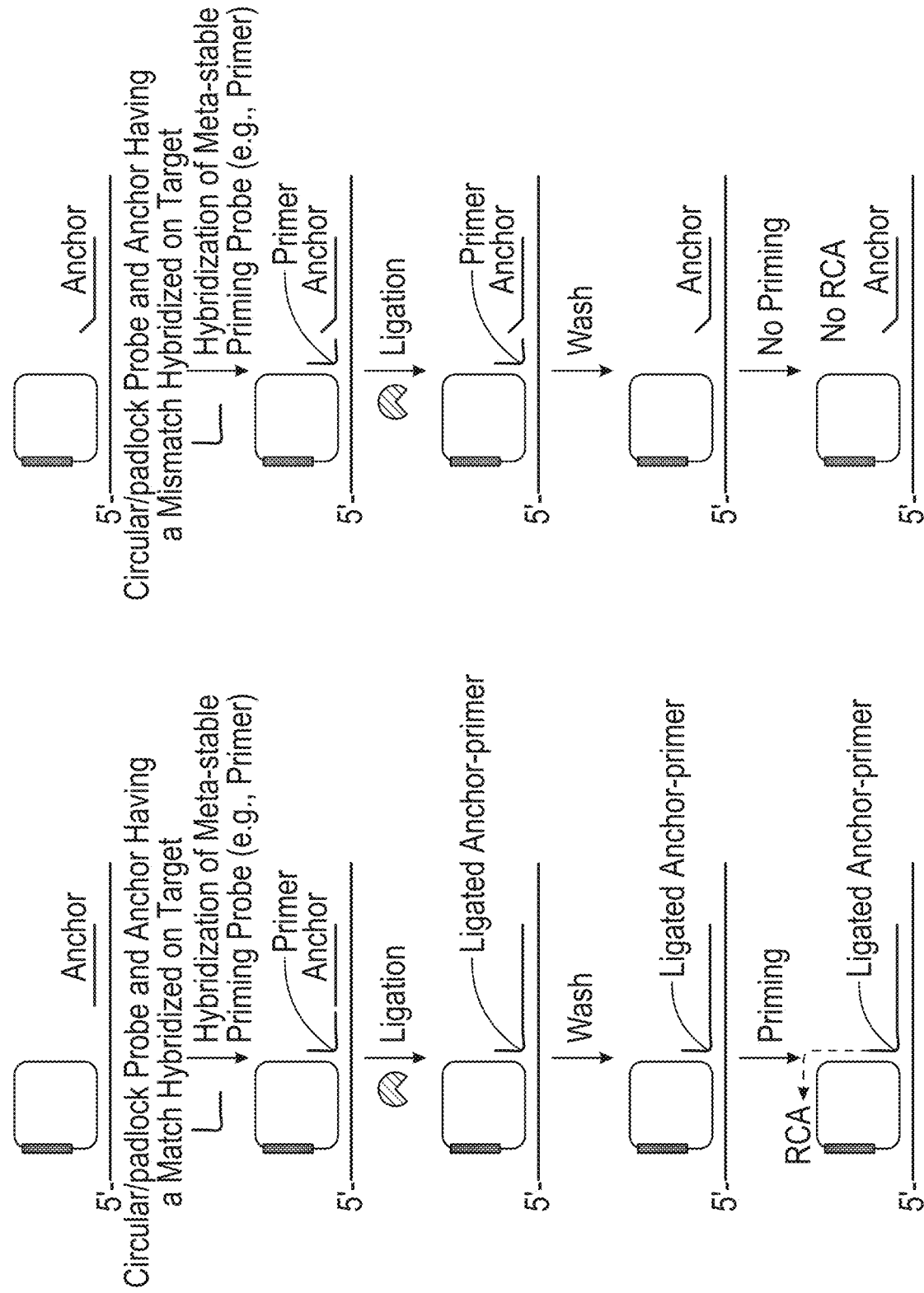
FIG. 8 shows exemplary methods where a circular/padlock probe and an anchor are both hybridized on a target, and a primer is then added. Here, a ligase (such as a high fidelity ligase capable of RNA-templated ligation) ligates the primer to the anchor when the anchor comprises a nucleotide that matches a nucleotide of interest in the target, but does not ligate the primer to the anchor when the anchor comprises a mismatch, and the primer can be dissociated (e.g., washed away under stringent conditions).

In some aspects, the methods provided herein comprise the use of a polynucleotide that is an anchor. In some aspects, the anchor contains an HR that hybridizes to an HR contained in the target nucleic acid. In FIG. 1-5, the HR of the anchor is labelled as HR3 and hybridizes to the HR of the target nucleic acid labelled HR3'. In some embodiments, the HR of the anchor comprises at least one nucleotide complementary to the region of interest (e.g., single nucleotide of interest) contained in the target nucleic acid. In some embodiments, a complementary nucleotide hybridizes to the single nucleotide of interest. In certain aspects, the anchor is designed such that ligation and/or amplification of one or more polynucleotides is dependent on hybridization of the anchor to the target nucleic acid and a nucleotide in the anchor basepairing to the single nucleotide of interest. In some cases, the anchor is designed such that ligation of the anchor to one of the other probe polynucleotides (e.g., primer) may provide stability for the formation of the hybridization complex and allow amplification of one or more polynucleotides. For example, as shown in FIG. 8 (left panel), ligation of the anchor to a primer templated by the target nucleic acid can stabilize hybridization of the metastable primer, resulting in priming and RCA. As shown in FIG. 8 (right panel), in some embodiments, if the anchor comprises a mismatch with the target nucleic acid, the anchor is not ligated to the primer, and the primer does not remain hybridized to the target nucleic acid, resulting in no priming and no RCA. Optionally, the metastable primer is removed in a wash step. In some aspects, while the exemplary figures depict a single nucleotide of interest in the target nucleic acid, a region of interest comprising more than one nucleotides of interest may be detected in a similar manner.

In some embodiments, the at least one complementary nucleotide(s) is part of the five terminal nucleotide positions of the HR in the anchor, either on the 3' or on the 5' end. In some embodiments, the complementary nucleotide is at one of the five terminal nucleotide positions of the HR in the anchor, either on the 3' or on the 5' end. In some embodiments, the complementary nucleotide is at the fifth terminal nucleotide position of the HR, with the 3' or 5' terminal nucleotide occupying the first terminal nucleotide position. In some embodiments, the complementary nucleotide is at the fourth terminal nucleotide position of the HR. In some embodiments, the complementary nucleotide is at the third terminal nucleotide position of the HR. In some embodiments, the complementary nucleotide is at the second terminal nucleotide position of the HR. In some embodiments, the complementary nucleotide is at the terminus of the HR. In some embodiments, the complementary nucleotide is the 3' end nucleotide of the HR in the anchor.

In some embodiments, the complementary nucleotide is the 3' end nucleotide of the anchor HR, and the single nucleotide of interest is the 5' end nucleotide of the target nucleic acid HR that hybridizes to the anchor HR.

The anchor may be of any suitable length. For example, the anchor selected may depend on characteristics of the hybridization of the anchor to the target nucleic acid (e.g., stability of the interaction). In some embodiments, the anchor is between or between about 5 and 40 nucleotides in length. In some embodiments, the anchor is between or between about 5 and 15 nucleotides in length. In some embodiments, the anchor is between or between about 15 and 20 nucleotides in length. In some embodiments, the anchor is between or between about 20 and 25 nucleotides in length. In some embodiments, the anchor is between or between about 25 and 30 nucleotides in length. In some embodiments, the anchor is between or between about 30 and 35 nucleotides in length. In some embodiments, the anchor is between or between about 25 and 30 nucleotides in length. In some embodiments, the anchor is between or between about 35 and 40 nucleotides in length.

In some embodiments, the anchor HR is between or between about 5 and 40 nucleotides in length. In some embodiments, the anchor HR is between or between about 5 and 10 nucleotides in length. In some embodiments, the anchor HR is between or between about 5 and 15 nucleotides in length. In some embodiments, the anchor HR is between or between about 15 and 20 nucleotides in length. In some embodiments, the anchor HR is between or between about 20 and 25 nucleotides in length. In some embodiments, the anchor HR is between or between about 25 and 30 nucleotides in length. In some embodiments, the anchor HR is between or between about 30 and 35 nucleotides in length. In some embodiments, the anchor HR is between or between about 25 and 30 nucleotides in length. In some embodiments, the anchor HR is between or between about 35 and 40 nucleotides in length.

In some embodiments, the anchor also comprises an overhang sequence, e.g., a sequence that does not hybridize to the target nucleic acid or to other polynucleotides. In certain aspects, the overhang provides a sequence by which the anchor can be detected, for instance via in situ hybridization to the overhang sequence. In some embodiments, the overhang comprises a barcode sequence, optionally one or more additional barcode sequences. In some embodiments, the barcode sequence identifies a nucleic acid sequence and/or the single nucleotide of interest.

In some embodiments, the overhang is between or between about 5 and 40 nucleotides in length. In some embodiments, the overhang is between or between about 5 and 15 nucleotides in length. In some embodiments, the overhang is between or between about 15 and 20 nucleotides in length. In some embodiments, the overhang is between or between about 20 and 25 nucleotides in length. In some embodiments, the overhang is between or between about 25 and 30 nucleotides in length. In some embodiments, the overhang is between or between about 30 and 35 nucleotides in length. In some embodiments, the overhang is between or between about 25 and 30 nucleotides in length. In some embodiments, the overhang is between or between about 35 and 40 nucleotides in length.

In some embodiments, the anchor is a DNA molecule. In some embodiments, the anchor is an RNA molecule or comprises ribonucleotides. In some embodiments, the anchor comprises a HR that is a DNA binding region. In some embodiments, the anchor comprises a HR that is an RNA binding region. In some embodiments, the anchor is a modified nucleic acid molecule or contains modified nucleotides or modified nucleosides, such as methylated nucleotides and nucleotide analogs, uracyl, other sugars, and linking groups such as fluororibose and thioate, and nucleotide branches. In some embodiments, the anchor may comprise non-nucleotide components. In some embodiments, the anchor may be modified to comprise N3'-P5' (NP) phosphoramidate, morpholino phosphorociamidate (MF), locked nucleic acid (LNA), 2'-O-methoxyethyl (MOE), or 2'-fluoro, arabino-nucleic acid (FANA). In some embodiments, the anchor comprises LNA. In some aspects, the modification can be used as an anchoring site to anchor the amplified product to the scaffold, other probe polynucleotides, other amplification products and/or to cellular structures, e.g., as described in Section V below.

2. Circular/Padlock Probe and Primer

In some aspects, the methods provided herein also comprise the use of a polynucleotide that is a circular or a circularizable probe or probe set (e.g., a padlock probe) and a polynucleotide that is a primer (e.g., priming probe) which optionally can function as a splint for circularizing the padlock. In some aspects, the circular or padlock probe and the primer for use in the methods provided herein hybridize to one another such that the padlock probe is circularized, and/or that the primer used the circular probe or circularized padlock as a template for amplification. Thus, in some aspects, the probes are designed such that subsequent ligation and/or amplification of one of the polynucleotides is dependent on hybridization of the circular or padlock probe and the primer to one another, as well as hybridization of the circular or padlock probe to the target nucleic acid.

A circularizable probe or probe set (e.g., a padlock probe) can be provided in one or more probe parts (e.g., as a single nucleic acid molecule, or as two or more nucleic acid molecules) that can be ligated together to form a circularized probe. Since the probe may be provided in one or more parts it follows that there may be more than one ligation junction. In other words, one or more probe parts may each comprise, or generate (i.e. by cleavage or extension), ligatable 5' and 3' ends, and the probe as a whole may comprise, or generate, one or more ligatable 5' ends and one or more ligatable 3' ends. For example, a padlock probe could be provided in two or more parts. In some embodiments, the 5' end of the first part can be ligated to the 3' end of the second part using, for example, the target nucleic acid as a template, and the 3' end of the first part can be ligated to the 5' end of the second part in a templated (e.g., splint templated) or non-templated ligation, thereby generating a circularized probe.

In some aspects, the circular or padlock probe comprises at least two HRs. In FIGS. 1-5, two HRs of the circular or padlock probe are labelled as HRa and HR1. In some embodiments, the HRs are adjacent to one another. In some embodiments, the HRs are immediately adjacent to one another. In other embodiments, the HRs are not immediately adjacent to one another and instead are separated by a gap, for instance a gap of 1, 2, 3, 4, or 5 nucleotides.

In some aspects, one of the HRs contained in the circular or padlock probe hybridizes to an HR in the target nucleic acid that does not contain the region of interest (e.g., single nucleotide of interest). For instance, in FIGS. 1-5, the HR labelled as HR1 of the circular or padlock probe hybridizes to the HR of the target nucleic acid labelled as HR1'.

In some embodiments, HR1 of the circular or padlock probe is between or between about 5 and 40 nucleotides in length. In some embodiments, HR1 is between or between about 5 and 15 nucleotides in length. In some embodiments, HR1 is between or between about 15 and 20 nucleotides in length. In some embodiments, HR1 is between or between about 20 and 25 nucleotides in length. In some embodiments, HR1 is between or between about 25 and 30 nucleotides in length. In some embodiments, HR1 is between or between about 30 and 35 nucleotides in length. In some embodiments, HR1 is between or between about 25 and 30 nucleotides in length. In some embodiments, HR1 is between or between about 35 and 40 nucleotides in length.

In some aspects, the primer comprises at least two HRs. In FIGS. 1-5, two HRs of the primer are labelled as HRb and HR2. In some embodiments, the HRs are adjacent to one another. In some embodiments, the HRs are immediately adjacent to one another. In other embodiments, the HRs are not immediately adjacent to one another and instead are separated by a gap, for instance a gap of 1, 2, 3, 4, or 5 nucleotides.

In some aspects, one of the HRs contained in the primer hybridizes to an HR in the target nucleic acid that contains the region of interest. In some aspects, one of the HRs contained in the primer hybridizes to an HR in the target nucleic acid that contains the single nucleotide of interest. For instance, in FIGS. 1 and 3-5, the HR labelled as HR2 of the primer hybridizes to the HR of the target nucleic acid labelled as HR2'.

In some embodiments, the HR1' which is configured to bind to HR1 of the circular or padlock probe and HR2' which is configured to bind to the HR2 of the primer is adjacent to each other. In some embodiments, HR1' and HR2' are immediately adjacent to one another. In other embodiments, HR1' and HR2' are not immediately adjacent to one another and instead are separated by a gap, for instance, a gap of 1, 2, 3, 4, or 5 nucleotides. In some examples, HR1' and HR2' are not immediately adjacent to one another and instead are separated by a gap, for instance, separated by a gap of less than 50, 45, 40, 35, 30, 25, 20, 15, 10, 9, 8, 7, 6, 5, 4, 3, 2, or 1 nucleotides. For example, HR1' and HR2' need not be in proximity in nucleotide space (e.g., the sequences may not be immediately adjacent to each other and can be separated by a gap), but the regions can be in physical proximity during hybridization to the target nucleic acid such that ligation may occur. In some examples, the target nucleic acid may comprise a non-hybridization region between HR1' and HR2' that may not interact with the probe polynucleotides (e.g., the circular or padlock probe, primer, and anchor). In some embodiments, the gap may allow detection of splice junctions or secondary conformations of the target nucleic acid (e.g., RNA). In some embodiments, HR2' is located 3' to HR1' on the target nucleic acid. In some examples, HR3' is located 3' to HR2' on the target nucleic acid. In some specific cases, the target nucleic acid comprises from a 5' end to a 3' end: HR1'-HR2'-HR3'.

In some embodiments, HR2 of the primer is between or between about 4 and 20 nucleotides in length. In some embodiments, HR2 is between or between about 5 and about 15 nucleotides in length. In some embodiments, HR2 is between or between about 5 and about 10 nucleotides in length.

Figure 7:
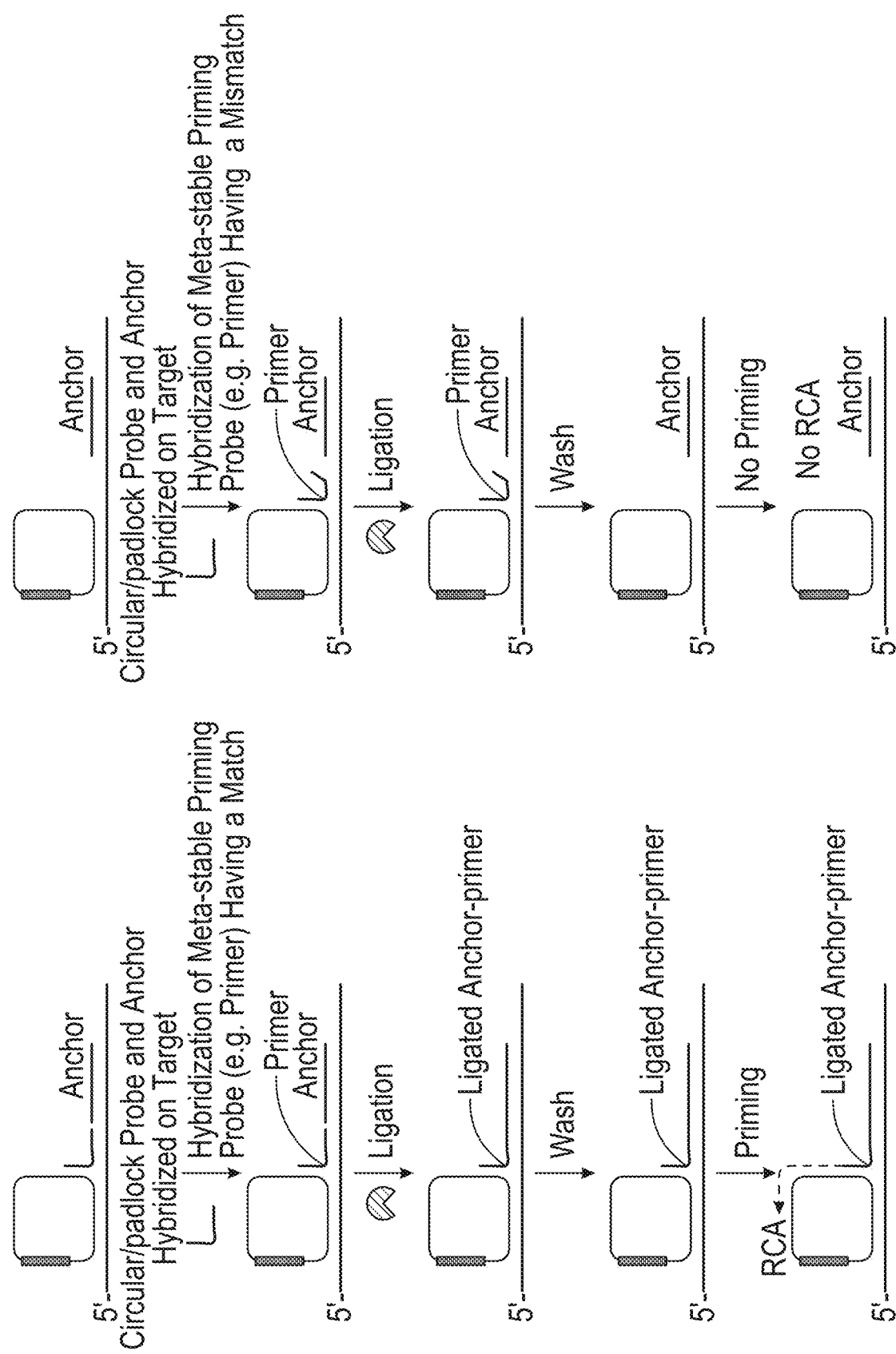
FIG. 7 shows exemplary methods where a circular/padlock probe and an anchor are both hybridized on a target, and a primer is then added. A ligase (such as a high fidelity ligase capable of RNA-templated ligation) ligates the primer to the anchor when the primer comprises a nucleotide that matches a nucleotide of interest in the target, but does not ligate the primer to the anchor when the primer comprises a mismatch, and the primer can be dissociated (e.g., washed away under stringent conditions).

In some embodiments, the length of HR2 of the primer and/or HR3 of the anchor is about 4 to about 40 nucleotides, such as about 5 to about 15 nucleotides or about 8 to about 10 nucleotides. In some aspects, the length of HR2 and/or HR3 is fewer than 20 nucleotides, such as 4, 5, 6, 7, 8, 9, 10, 11, 12, 13, 14, 15, 16, 17, 18, 19, or 20 nucleotides. In some embodiments, ligation of the anchor to the primer stabilizes hybridization of primer to the target as well as to the circular or padlock probe, thereby allowing the primer to remain hybridized (e.g., under stringent wash conditions) and initiate rolling circle amplification, as shown in the left panel of FIG. 7. In some embodiments, if the primer comprises a mismatch with the target nucleic acid, the primer is not ligated to the anchor, and does not remain hybridized to the target nucleic acid, resulting in no priming and no RCA (as shown in FIG. 7, right panel). Optionally, the primer comprising a mismatch is removed in a wash step. In some aspects, the length of any of the described HRs (e.g., of the target nucleic acid, circular or padlock probe, primer, anchor) may be designed, selected, and/or adjusted to achieve the desired level of stability of the complex formed. I In some embodiments, the $T_m$ of the circular or padlock probe to target hybridization and the $T_m$ of the anchor/target hybridization are the same or substantially the same, e.g., differing by less than 0.1° C., less than 0.5° C., less than 1° C., less than 2° C., less than 3° C., less than 4° C., or less than 5° C. In some embodiments, the length of HR1 and/or HR3 are the same or substantially the same, e.g., differing by 1, 2 or fewer, 3 or fewer, 4 or fewer, 5 or fewer, 6 or fewer, 7 or fewer, 8 or fewer, 9 or fewer, or 10 or fewer nucleotides.

In some embodiments, the $T_m$ of the circular or padlock probe to target hybridization and the $T_m$ of the anchor/target hybridization are between or between about 40° C. and about 70° C., such as between at or about 50° C. and at or about 65° C., or at or about 60° C.

In some embodiments, the $T_m$ of the unligated primer hybridization to the target and/or to the padlock or circular probe is lower than the $T_m$ of the circular or padlock probe to target hybridization and/or the $T_m$ of the anchor/target hybridization, e.g., by at least or at least about 5° C., at least or at least about 10° C., at least or at least about 15° C., at least or at least about 20° C., at least or at least about 25° C., at least or at least about 30° C., at least or at least about 40° C., at least or at least about 45° C., or at least or at least about 50° C. lower. In some embodiments, the $T_m$ of the unligated primer hybridization to the target and/or to the padlock or circular probe is between or between about 15° C. and about 50° C., such as between at or about 20° C. and at or about 40° C., between at or about 25° C. and at or about 30° C., or at or about 27° C.

In some aspects, for example as shown in FIGS. 1-5, HRa hybridizes to HRb, one or both of which can be between or between about 5 and about 20 nucleotides in length, e.g., between about 5 and about 15 nucleotides in length.

In some aspects, the circular or padlock probe further comprises a sequence by which the probe or an amplification product thereof can be analyzed, e.g., detected or sequenced. In some embodiments, HRa comprises a sequence by which the single nucleotide of interest can be identified. In some embodiments, a sequence by which the single nucleotide of interest can be identified is 2, 4, 6, 8, or 10 nucleotides in length.

In some aspects, the circular or padlock probe comprises a barcode sequence that identifies a nucleic acid sequence, region of interest, or a single nucleotide of interest, for instance the single nucleotide of interest contained in the target nucleic acid. In some embodiments, the padlock probe contains one or more other barcode sequences. In some embodiments, one of the one or more other barcode sequences identifies the target nucleic acid, e.g., an mRNA, as a splice variant. In some embodiments, one of the one or more other barcode sequences identifies a splice junction sequence.

In some embodiments, the circular or padlock probe is a DNA molecule. In some embodiments, the circular or padlock probe is an RNA molecule or comprises ribonucleotides. In some embodiments, the circular or padlock probe is a modified nucleic acid molecule or contains modified nucleotides or modified nucleosides, such as methylated nucleotides and nucleotide analogs, uracyl, other sugars, and linking groups such as fluororibose and thioate, and nucleotide branches. In some embodiments, the circular or padlock probe may comprise non-nucleotide components. In some embodiments, the circular or padlock probe may be modified to comprise N3'-P5' (NP) phosphoramidate, morpholino phosphorociamidate (MF), locked nucleic acid (LNA), 2'-0-methoxyethyl (MOE), or 2'-fluoro, arabino-nucleic acid (FANA). In some embodiments, the circular or padlock probe comprises LNA. In some aspects, the modification can be used as an anchoring site to anchor the amplified product to the scaffold, other probe polynucleotides, other amplification products and/or to cellular structures, e.g., as described in Section V below.

In some embodiments, the primer is a DNA molecule. In some embodiments, the primer is an RNA molecule or comprises ribonucleotides. In some embodiments, the primer is a modified nucleic acid molecule or contains modified nucleotides or modified nucleosides, such as methylated nucleotides and nucleotide analogs, uracyl, other sugars, and linking groups such as fluororibose and thioate, and nucleotide branches. In some embodiments, the primer may comprise non-nucleotide components. In some embodiments, the padlock probe may be modified to comprise N3'-P5' (NP) phosphoramidate, morpholino phosphorociamidate (MF), locked nucleic acid (LNA), 2'-O-methoxyethyl (MOE), or 2'-fluoro, arabino-nucleic acid (FANA). In some embodiments, the primer comprises LNA. In some aspects, the modification can be used as an anchoring site to anchor the amplified product to the scaffold, other probe polynucleotides, other amplification products and/or to cellular structures, e.g., as described in Section V below.

IV. Ligation

In some embodiments, the methods provided herein involve ligating together two of the polynucleotides, for instance the anchor and the primer. In some embodiments, the anchor and the primer are ligated in order to form a ligated anchor-primer. In some embodiments, the methods provided herein also involve ligating the 5' and 3' ends of one of the polynucleotides, for instance the padlock probe, in order to form a circularized probe.

In some embodiments, the provided methods involve ligating one or more polynucleotides that are part of a hybridization complex that comprises a target nucleic acid with a single nucleotide of interest. In some embodiments, the provided methods involve ligating an anchor and a primer and optionally ligating the ends of a padlock probe that are part of the hybridization complex.

In some aspects, the ligation of the anchor and the primer is dependent on the anchor hybridizing to the region of interest, (e.g., single nucleotide of interest) contained in the target nucleic acid. In some embodiments, base pairing between a single nucleotide of interest contained in the target nucleic acid and the nucleotide complementary to the single nucleotide of interest contained in the anchor and/or the primer promotes the ends of the anchor and the primer to be in sufficient proximity for ligation. This dependency provides the specificity by which the presence or identity of the single nucleotide of interest can be determined.

In some embodiments, ligation is performed under conditions permissive for specific hybridization of the polynucleotides to one another and/or to the target nucleic acid. In some embodiments, the ligation to form the ligated anchor-primer is performed under conditions permissive for specific hybridization of the polynucleotides to one another and/or to the target nucleic acid. In some embodiments, the ligation to form the ligated anchor-primer is performed under conditions permissive for specific hybridization of the circular or padlock probe to the target nucleic acid. In some embodiments, the ligation to form the ligated anchor-primer is performed under conditions permissive for specific hybridization of the anchor to the target nucleic acid. In some embodiments, the ligation to form the ligated anchor-primer is performed under conditions permissive for specific hybridization of the primer to the target and to the circular or padlock probe.

In some embodiments, the ligation to form the circular probe is performed under conditions permissive for specific hybridization of the padlock probe to the target nucleic acid. In some embodiments, the ligation to form the circularized probe is performed under conditions permissive for specific hybridization of the primer (as a splint) to the padlock probe.

In some embodiments, the ligation of the anchor and the primer and the ligation of the ends of the padlock probe are done sequentially. In some embodiments, the anchor and the primer are ligated before the padlock probe is circularized. In some embodiments, the anchor and the primer are ligated after the padlock probe is circularized. In other embodiments, the ligation of the anchor and the primer and the circularization of the padlock probe are done simultaneously.

In some embodiments, the ligation involves chemical ligation. In some embodiments, the ligation involves template dependent ligation. In some embodiments, the ligation involves template independent ligation. In some embodiments, the ligation involves enzymatic ligation.

In some embodiments, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase. In some embodiments, the ligase is a splintR ligase. In some embodiments, the ligase is a single stranded DNA ligase. In some embodiments, the ligase is a T4 DNA ligase.

In some embodiments, the ligase is a ligase that has an RNA-splinted DNA ligase activity. In some embodiments, any or all of the anchor, primer, and circular or padlock probe are DNA molecules.

In some embodiments, the ligation may be direct ligation or indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, i.e., separated by one or more intervening nucleotides or "gaps". In some embodiments, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo)nucleotide(s) which are complementary to a splint (e.g., a primer disclosed herein) or target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide, for instance the padlock probe or anchor. In some cases, ligation involves ligating the ends of the probe to at least one gap (oligo)nucleotide, such that the gap (oligo)nucleotide becomes incorporated into the resulting polynucleotide.

In some embodiments, the ligation of the anchor and the primer is preceded by gap filling. In other embodiments, the ligation of the anchor and the primer does not require gap filling.

In some embodiments, the ligation of the 5' and 3' ends of the padlock probe does not require gap filling. In other embodiments, the ligation of the 5' and 3' ends of the padlock probe is preceded by gap filling.

In some embodiments, ligation of the polynucleotides produces polynucleotides with melting temperature higher than that of unligated polynucleotides. Thus, in some aspects, ligation stabilizes the hybridization complex containing the ligated polynucleotides prior to subsequent steps, comprising amplification and detection. In some embodiments, the melting temperature of the ligated anchor-primer for hybridization to the target nucleic acid and the circular or circularized padlock probe is higher than the $T_m$ of the unligated anchor for hybridization to the target nucleic acid. In some embodiments, the melting temperature of the ligated anchor-primer for hybridization to the target nucleic acid and/or the circular or circularized padlock probe is higher than the $T_m$ of the unligated primer for hybridization to the target nucleic acid and/or the circular or padlock probe.

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature ($T_m$) of the DNA strands. This selectively reduces the concentration of annealed mismatched substrates (expected to have a slightly lower $T_m$ around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

V. Amplification

In some embodiments, the methods of the invention comprise the step of amplifying one or more polynucleotides, for instance the circular probe or a circularized probe formed from a padlock probe. In some embodiments, the amplifying is achieved by performing rolling circle amplification (RCA). In some embodiments, the performing comprises contacting a target nucleic acid with a circular or padlock probe, a primer, and an anchor to form a hybridization complex, e.g., as described in Section III. In some embodiments, following ligation and circularization of the padlock probe, e.g., as performed using any of the exemplary methods described in Section IV, amplification is performed using the circular or circularized probe as template and the ligated anchor-primer as a primer.

In some embodiments, a removing step is performed to remove molecules that are not specifically hybridized to the target nucleic acid and/or the circular probe. In some embodiments, the removing step is performed to remove unligated probes. In some embodiments, the removing step is performed after ligation and prior to amplification. In some embodiments, the removing step is performed at a temperature lower than the melting temperature of the ligated anchor-primer for hybridization to the target nucleic acid and the circular probe. In some embodiments, the removing step is performed at a temperature higher than the melting temperature of the anchor for hybridization to the target nucleic acid. In some embodiments, the removing step is performed at a temperature higher than the melting temperature of the primer for hybridization to the circular probe. In some embodiments, the ligated anchor-primer remains specifically hybridized to the circular probe after the removing step. In some embodiments, the circular probe remains specifically hybridized to the target nucleic acid after the removing step. In some embodiments, the ligated anchor-primer remains specifically hybridized to the target nucleic acid after the removing step. In some embodiments, non-ligated primer molecules are removed. In some embodiments, non-ligated anchor molecules are removed.

In some embodiments, the amplification is performed at a temperature lower than the melting temperature of the ligated anchor-primer for hybridization to the target nucleic acid and the circular probe. In some embodiments, the amplification is performed at a temperature higher than the melting temperature of the anchor for hybridization to the target nucleic acid. In some embodiments, the amplification is performed at a temperature higher than the melting temperature of the primer for hybridization to the circular probe. In some embodiments, the amplification is performed at a temperature between or between about 20° C. and about 60° C. In some embodiments, the amplification is performed at a temperature between or between about 30° C. and about 40° C.

In some aspects, the amplification steps can be performed at a temperature that is lower than the $T_m$ of hybridization of the HRs between the probe polynucleotides and target site on the target nucleic acid, at a temperature required for the amplification step. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some embodiments, upon addition of a DNA polymerase in the presence of appropriate dNTP precursors and other cofactors, the ligated anchor-primer or another primer is elongated to produce multiple copies of the circular template. This amplification step can utilize isothermal amplification or non-isothermal amplification. In some embodiments, after the formation of the hybridization complex and association of the amplification probe, the hybridization complex is rolling-circle amplified to generate a cDNA nanoball (i.e., amplicon) containing multiple copies of the cDNA. Techniques for rolling circle amplification (RCA) are known in the art such as linear RCA, a branched RCA, a dendritic RCA, or any combination thereof. (See, e.g., Baner et al, Nucleic Acids Research, 26:5073-5078, 1998; Lizardi et al, Nature Genetics 19:226, 1998; Mohsen et al., Acc Chem Res. 2016 Nov. 15; 49(11): 2540-2550; Schweitzer et al. Proc. Natl Acad. Sci. USA 97:101 13-1 19, 2000; Faruqi et al, BMC Genomics 2:4, 2000; Nallur et al, Nucl. Acids Res. 29:e118, 2001; Dean et al. Genome Res. 1 1:1095-1099, 2001; Schweitzer et al, Nature Biotech. 20:359-365, 2002; U.S. Pat. Nos. 6,054,274, 6,291,187, 6,323,009, 6,344,329 and 6,368,801). Exemplary polymerases for use in RCA comprise DNA polymerase such phi29 (φ29) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some embodiments, the polymerase is phi29 DNA polymerase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects, the modified nucleotides can be employed. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some aspects, the polynucleotides and/or amplification product (e.g., amplicon) can be anchored to a polymer matrix. For example, the polymer matrix can be a hydrogel. In some embodiments, one or more of the polynucleotide probe(s) can be modified to contain functional groups that can be used as an anchoring site to attach the polynucleotide probes and/or amplification product to a polymer matrix.

Exemplary modification and polymer matrix that can be employed in accordance with the provided embodiments comprise those described in, for example, WO 2014/163886, WO 2017/079406, US 2016/0024555, US 2018/0251833 and WO2014/025392. In some examples, the scaffold also contains modifications or functional groups that can react with or incorporate the modifications or functional groups of the probe set or amplification product. In some examples, the scaffold can comprise oligonucleotides, polymers or chemical groups, to provide a matrix and/or support structures.

The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products are copolymerized and/or covalently attached to the surrounding matrix thereby preserving their spatial relationship and any information inherent thereto. For example, if the amplification products are those generated from DNA or RNA within a cell embedded in the matrix, the amplification products can also be functionalized to form covalent attachment to the matrix preserving their spatial information within the cell thereby providing a subcellular localization distribution pattern. In some embodiments, the provided methods involve embedding the one or more polynucleotide probe sets and/or the amplification products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

VI. Detection and Analysis

In some aspects, the provided methods involve analyzing, e.g., detecting or determining, one or more sequences present in the polynucleotides and/or in an amplification product, such as in an amplified padlock probe. In some embodiments, the analysis comprises determining the sequence of all or a portion of the amplification product. In some embodiments, the analysis comprises detecting a sequence present in the amplification product. In some embodiments, the analysis comprises detecting the presence or absence of the amplification product. In some embodiments, the sequence of all or a portion of the amplification product is indicative of the identity of a single nucleotide of interest in a target nucleic acid. In some examples, the absence of a region of interest (e.g., a single nucleotide of interest and/or a polymorphism) in the target nucleic acid may be indicated by the absence of an amplification product due to any of the probe polynucleotides (e.g., the circular or padlock probe, primer, and anchor) not hybridizing to the target nucleic acid in a manner sufficient for ligation and subsequent amplification to occur. In some examples, the presence of a region of interest (e.g., a single nucleotide of interest and/or a polymorphism) in the target nucleic acid may be indicated by the presence of an amplification product due to the probe polynucleotides (e.g., the circular or padlock probe, primer, and anchor) hybridizing to the target nucleic acid in a manner sufficient for ligation and subsequent amplification to occur.

In some embodiments, the methods comprise sequencing all or a portion of the amplification product, such as one or more barcode sequences present in the amplification product. In some embodiments, the analysis and/or sequence determination comprises sequencing all or a portion of the amplification product and/or in situ hybridization to the amplification product. In some embodiments, the sequencing step involves sequencing hybridization, sequencing by ligation, and/or fluorescent in situ sequencing, and/or wherein the in situ hybridization comprises sequential fluorescent in situ hybridization. In some embodiments, the detection or determination comprises hybridizing to the amplification product a detection oligonucleotide labeled with a fluorophore, an isotope, a mass tag, or a combination thereof. In some embodiments, the detection or determination comprises imaging the amplification product. In some embodiments, the target nucleic acid is an mRNA in a tissue sample, and the detection or determination is performed when the target nucleic acid and/or the amplification product is in situ in the tissue sample.

In some aspects, the provided methods comprise imaging the amplification product (e.g., amplicon) and/or one or more portions of the polynucleotides, for example, via binding of the detection probe (directly or indirectly) and detecting the detectable label. In some embodiments, the detection probe comprises a detectable label that can be measured and quantitated. The terms "label" and "detectable label" comprise a directly or indirectly detectable moiety that is associated with (e.g., conjugated to) a molecule to be detected, e.g., a detectable probe, comprising, but not limited to, fluorophores, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorophore" comprises a substance or a portion thereof that is capable of exhibiting fluorescence in the detectable range. Particular examples of labels that may be used in accordance with the provided embodiments comprise, but are not limited to phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, Renilla luciferase, NADPH, beta-galactosidase, horseradish peroxidase, glucose oxidase, alkaline phosphatase, chloramphenical acetyl transferase, and urease.

Fluorescence detection in tissue samples can often be hindered by the presence of strong background fluorescence. "Autofluorescence" is the general term used to distinguish background fluorescence (that can arise from a variety of sources, including aldehyde fixation, extracellular matrix components, red blood cells, lipofuscin, and the like) from the desired immunofluorescence from the fluorescently labeled antibodies or probes. Tissue autofluorescence can lead to difficulties in distinguishing the signals due to fluorescent antibodies or probes from the general background. In some embodiments, a method disclosed herein utilizes one or more agents to reduce tissue autofluorescence, for example, Autofluorescence Eliminator (Sigma/EMD Millipore), TrueBlack Lipofuscin Autofluorescence Quencher (Biotium), MaxBlock Autofluorescence Reducing Reagent Kit (MaxVision Biosciences), and/or a very intense black dye (e.g., Sudan Black, or comparable dark chromophore).

In some embodiments, a detectable probe containing a detectable label can be used to detect one or more polynucleotide(s) and/or amplification products (e.g., amplicon) described herein. In some embodiments, the methods involve incubating the detectable probe containing the detectable label with the sample, washing away unbound detectable probe, and detecting the label, e.g., by imaging. In some embodiments, the methods involve incubating the sample with a probe that comprises an overhang that does not hybridize to the amplification product and a sequence on the overhang hybridizes to another probe (e.g., a detectably labelled probe).

Examples of detectable labels comprise but are not limited to various radioactive moieties, enzymes, prosthetic groups, fluorescent markers, luminescent markers, bioluminescent markers, metal particles, protein-protein binding pairs and protein-antibody binding pairs. Examples of fluorescent proteins comprise, but are not limited to, yellow fluorescent protein (YFP), green fluorescence protein (GFP), cyan fluorescent protein (CFP), umbelliferone, fluorescein, fluorescein isothiocyanate, rhodamine, dichlorotriazinylamine fluorescein, dansyl chloride and phycoerythrin.

Examples of bioluminescent markers comprise, but are not limited to, luciferase (e.g., bacterial, firefly and click beetle), luciferin, aequorin and the like. Examples of enzyme systems having visually detectable signals comprise, but are not limited to, galactosidases, glucorimidases, phosphatases, peroxidases and cholinesterases. Identifiable markers also comprise radioactive compounds such as $^{125}$I, $^{35}$S, $^{14}$C, or $^{3}$H. Identifiable markers are commercially available from a variety of sources.

Examples of fluorescent labels and nucleotides and/or polynucleotides conjugated to such fluorescent labels comprise those described in, for example, Hoagland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). In some embodiments, exemplary techniques and methods methodologies applicable to the provided embodiments comprise those described in, for example, U.S. Pat. Nos. 4,757,141, 5,151,507 and 5,091,519. In some embodiments, one or more fluorescent dyes are used as labels for labeled target sequences, for example, as described in U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthine dyes); and U.S. Pat. No. 5,688,648 (energy transfer dyes). Labelling can also be carried out with quantum dots, as described in U.S. Pat. Nos. 6,322,901, 6,576,291, 6,423,551, 6,251,303, 6,319,426, 6,426,513, 6,444,143, 5,990,479, 6,207,392, US 2002/0045045 and US 2003/0017264. As used herein, the term "fluorescent label" comprises a signaling moiety that conveys information through the fluorescent absorption and/or emission properties of one or more molecules. Exemplary fluorescent properties comprise fluorescence intensity, fluorescence lifetime, emission spectrum characteristics and energy transfer.

Examples of commercially available fluorescent nucleotide analogues readily incorporated into nucleotide and/or polynucleotide sequences comprise, but are not limited to, Cy3-dCTP, Cy3-dUTP, Cy5-dCTP, Cy5-dUTP (Amersham Biosciences, Piscataway, N.J.), fluorescein-!2-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHOD AMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHOD AMINE GREEN™-5-UTP, ALEXA FLUOR™ 488-5-UTP, and ALEXA FLUOR™ 546-14-UTP (Molecular Probes, Inc. Eugene, Oreg.). Methods are known for custom synthesis of nucleotides having other fluorophores (See, Henegariu et al. (2000) Nature Biotechnol. 18:345).

Other fluorophores available for post-synthetic attachment comprise, but are not limited to, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, Texas Red (available from Molecular Probes, Inc., Eugene, Oreg.), Cy2, Cy3.5, Cy5.5, and Cy7 (Amersham Biosciences, Piscataway, N.J.). FRET tandem fluorophores may also be used, comprising, but not limited to, PerCP-Cy5.5, PE-Cy5, PE-Cy5.5, PE-Cy7, PE-Texas Red, APC-Cy7, PE-Alexa dyes (610, 647, 680), and APC-Alexa dyes.

In some cases, metallic silver or gold particles may be used to enhance signal from fluorescently labeled nucleotide and/or polynucleotide sequences (Lakowicz et al. (2003) Bio Techniques 34:62).

Biotin, or a derivative thereof, may also be used as a label on a nucleotide and/or an polynucleotide sequence, and subsequently bound by a detectably labeled avidin/streptavidin derivative (e.g., phycoerythrin-conjugated streptavidin), or a detectably labeled anti-biotin antibody. Digoxigenin may be incorporated as a label and subsequently bound by a detectably labeled anti-digoxigenin antibody (e.g., fluoresceinated anti-digoxigenin). An aminoallyl-dUTP residue may be incorporated into an polynucleotide sequence and subsequently coupled to an N-hydroxy succinimide (NHS) derivatized fluorescent dye. In general, any member of a conjugate pair may be incorporated into a detection polynucleotide provided that a detectably labeled conjugate partner can be bound to permit detection. As used herein, the term antibody refers to an antibody molecule of any class, or any sub-fragment thereof, such as an Fab.

Other suitable labels for a polynucleotide sequence may comprise fluorescein (FAM), digoxigenin, dinitrophenol (DNP), dansyl, biotin, bromodeoxyuridine (BrdU), hexahistidine (6xHis), and phosphor-amino acids (e.g., P-tyr, P-ser, P-thr). In some embodiments the following hapten/antibody pairs are used for detection, in which each of the antibodies is derivatized with a detectable label: biotin/a-biotin, digoxigenin/a-digoxigenin, dinitrophenol (DNP)/a-DNP, 5-Carboxyfluorescein (FAM)/a-FAM.

In some embodiments, a nucleotide and/or a polynucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, and PCT publication WO 91/17160. Many different hapten-capture agent pairs are available for use. Exemplary haptens comprise, but are not limited to, biotin, des-biotin and other derivatives, dinitrophenol, dansyl, fluorescein, Cy5, and digoxigenin. For biotin, a capture agent may be avidin, streptavidin, or antibodies. Antibodies may be used as capture agents for the other haptens (many dye-antibody pairs being commercially available, e.g., Molecular Probes, Eugene, Oreg.).

In some aspects, the detecting involves using detection methods such as flow cytometry; sequencing; probe binding and electrochemical detection; pH alteration; catalysis induced by enzymes bound to DNA tags; quantum entanglement; Raman spectroscopy; terahertz wave technology; and/or scanning electron microscopy. In some aspects, the flow cytometry is mass cytometry or fluorescence-activated flow cytometry. In some aspects, the detecting comprises performing microscopy, scanning mass spectrometry or other imaging techniques described herein. In such aspects, the detecting comprises determining a signal, e.g., a fluorescent signal.

In some aspects, the detection (comprising imaging) is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detection probe. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the detection probe. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (i.e., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

In some embodiments, sequencing can be performed in situ. In situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (i.e., nucleotide sequence) of the incorporated nucleotides or labeled primer extension products can be determined, and consequently, the nucleotide sequence of the corresponding template nucleic acid. Aspects of in situ sequencing are described, for example, in Mitra et al., (2003) Anal. Biochem. 320, 55-65, and Lee et al., (2014) Science, 343(6177), 1360-1363. In addition, examples of methods and systems for performing in situ sequencing are described in WO2014/163886, WO2018/045181, WO2018/045186, and in U.S. Pat. Nos. 10,138,509 and 10,179,932. Exemplary techniques for in situ sequencing, such as barcode detection schemes, comprise those described in, but are not limited to, STARmap (described for example in Wang et al., (2018) Science, 361(6499) 5691), MERFISH (described for example in Moffitt, (2016) Methods in Enzymology, 572, 1-49), and FISSEQ (described for example in US 2019/0032121).

In some embodiments, sequencing can be performed by sequencing-by-synthesis (SBS). In some embodiments, a sequencing primer is complementary to sequences at or near the one or more barcode(s). In such embodiments, sequencing-by-synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, WO 05/065814, US 2005/0100900, WO 06/064199, WO07/010,251, US 2012/0270305, US 2013/0260372, and US 2013/0079232.

In some embodiments, sequencing can be performed by sequential fluorescence hybridization (e.g., sequencing by hybridization). Sequential fluorescence hybridization can involve sequential hybridization of detection probes comprising an oligonucleotide and a detectable label.

In some embodiments, sequencing can be performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. Science (2005), 309: 1728-1732, and in U.S. Pat. Nos. 5,599,675; 5,750,341; 6,969,488; 6,172,218; and 6,306,597.

In some embodiments, the barcodes of the detection probes are targeted by detectably labeled detection oligonucleotides, such as fluorescently labeled oligonucleotides. In some embodiments, one or more decoding schemes are used to decode the signals, such as fluorescence, for sequence determination. In any of the embodiments herein, barcodes (e.g., primary and/or secondary barcode sequences) can be analyzed (e.g., detected or sequenced) using any suitable methods or techniques, comprising those described herein, and/or the barcode detection schemes as described in methods such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), in situ sequencing, targeted in situ sequencing, fluorescent in situ sequencing (FISSEQ), or spatially-resolved transcript amplicon readout mapping (STARmap). In some embodiments, the methods provided herein comprise analyzing the barcodes by sequential hybridization and detection with a plurality of labelled probes (e.g., detection oligonucleotides). Exemplary decoding schemes are described in Eng et al., "Transcriptome-scale Super-Resolved Imaging in Tissues by RNA SeqFISH+," Nature 568(7751):235-239 (2019); Chen et al., "Spatially resolved, highly multiplexed RNA profiling in single cells," Science; 348(6233):aaa6090 (2015); U.S. Pat. No. 10,457,980 B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., Genome Research 14:870-877 (2004).

In some embodiments, real-time monitoring of DNA polymerase activity can be used during sequencing. For example, nucleotide incorporations can be detected through fluorescence resonance energy transfer (FRET), as described for example in Levene et al., Science (2003), 299, 682-686, Lundquist et al., Opt. Lett. (2008), 33, 1026-1028, and term "perfectly et al., Proc. Natl. Acad. Sci. USA (2008), 105, 1176-1181.

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

In some embodiments, the analysis and/or sequence determination involves washing to remove unbound polynucleotides, thereafter revealing a fluorescent product for imaging.

A. Multiple Analytes

In some embodiments, a plurality of padlock probes, meta-stable primers, and anchors can be used to target various regions of interest, (e.g., single nucleotide of interests, e.g., various SNPs or SNP locations). In some embodiments, a method disclosed herein may be combined with methods analyzing one or more analytes other than regions of interest, (e.g., single nucleotide of interests).

In some aspects, the methods disclosed herein involve or can be combined with the use of one or more probes or probe sets that hybridize to a target nucleic acid, such as an RNA molecule. Exemplary probes or probe sets may be based on a padlock probe, a gapped padlock probe, a SNAIL (Splint Nucleotide Assisted Intramolecular Ligation) probe set, a PLAYR (Proximity Ligation Assay for RNA) probe set, a PLISH (Proximity Ligation in situ Hybridization) probe set, and RNA-templated ligation probes. The specific probe or probe set design can vary. In some embodiments, a primary probe (e.g., a DNA probe that directly binds to an RNA target) is amplified through rolling circle amplification, e.g., using a circular probe or a circularized probe from padlock ligation as a template. In some embodiments, the primary probes, such as a padlock probe or a probe set that comprises a padlock probe, contain one or more barcodes. In some embodiments, one or more barcodes are indicative of a sequence in the target nucleic acid, such as a single nucleotide of interest (e.g., SNPs or point mutations), a dinucleotide sequence, a short sequence of about 5 nucleotides in length, or a sequence of any suitable length.

In some embodiments, provided herein is a probe or probe set capable of DNA-templated ligation, such as from a cDNA molecule. See, e.g., U.S. Pat. No. 8,551,710, which is hereby incorporated by reference in its entirety. In some embodiments, provided herein is a probe or probe set capable of RNA-templated ligation. See, e.g., U.S. Pat. Pub. US 2020/0224244 which is hereby incorporated by reference in its entirety. In some embodiments, the probe set is a SNAIL probe set. See, e.g., U.S. Pat. Pub. 20190055594, which is hereby incorporated by reference in its entirety. In some embodiments, provided herein is a multiplexed proximity ligation assay. See, e.g., U.S. Pat. Pub. 20140194311 which is hereby incorporated by reference in its entirety. In some embodiments, provided herein is a probe or probe set capable of proximity ligation, for instance a proximity ligation assay for RNA (e.g., PLAYR) probe set. See, e.g., U.S. Pat. Pub. 20160108458, which is hereby incorporated by reference in its entirety.

In some embodiments, a circular probe can be indirectly hybridized to the target nucleic acid. In some embodiments, the circular construct is formed from a probe set capable of proximity ligation, for instance a proximity ligation in situ hybridization (PLISH) probe set. See, e.g., U.S. Pat. Pub. 2020/0224243 which is hereby incorporated by reference in its entirety.

In some embodiments, a protein analyte can be bound by one or more labelling agents capable of binding to or otherwise coupling to one or more features may be used to characterize cells and/or cell features (e.g., an antibody or antigen binding fragment thereof). In some embodiments, the labelling agents can include (e.g., are attached to) a reporter oligonucleotide that is indicative of the feature to which the labelling agent or portion thereof binds. For example, the reporter oligonucleotide may comprise a barcode sequence that permits identification of the labelling agent. In some examples, the labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. In some embodiments, the nucleic acid molecule comprises a sequence corresponding to the labelling agent and therefore corresponds to (e.g., uniquely identifies) the protein analyte. In some embodiments, the reporter oligonucleotide (e.g., a reporter oligonucleotide) can comprise a nucleic acid molecule comprising one or more barcode sequences. Thus, the nucleic acid molecule of the labelling agent, like a nucleic acid analyte disclosed herein, can be analyzed using any methods disclosed herein. For example, the reporter oligonucleotide associated with the labelling agent that specifically recognizes a protein can be analyzed using in situ hybridization (e.g., sequential hybridization) and/or in situ sequencing (e.g., using padlock probes and rolling circle amplification of ligated padlock probes). Further, the reporter oligonucleotide and/or a complement thereof and/or a product (e.g., a hybridization product, a ligation product, an extension product (e.g., by a DNA or RNA polymerase), a replication product, a transcription/reverse transcription product, and/or an amplification product such as an RCA product) thereof can be analyzed.

In some embodiments, an analyte (a nucleic acid analyte or non-nucleic acid analyte) can be specifically bound by two labelling agents (e.g., antibodies) each of which is attached to a nucleic acid molecule (e.g., DNA) that can participate in ligation, replication, and sequence decoding reactions. For example, a proximity ligation reaction can include oligonucleotides attached to pairs of antibodies that can be joined by ligation if the antibodies have been brought in proximity to each oligonucleotide, e.g., by binding the same target protein (complex), and the DNA ligation products that form are then used to template PCR amplification, as described for example in Soderberg et al., Methods. (2008); 45(3): 227-32, the entire contents of which are incorporated herein by reference.

In some embodiments, an analyte is specifically bound by two primary antibodies, each of which is attached to a nucleic acid molecule (e.g., DNA). Each nucleic acid molecule serves as a splint for ligation of two probes which upon ligation form a circularized probe. Each of the two probes can comprise one or more barcode sequences. Further, one of the two probes may serve as a primer for rolling circle amplification (RCA) of the circularized probe while the other probe has an end that is blocked from primer extension. In some embodiments, an analyte is specifically bound by two primary antibodies, each of which in turn recognized by a secondary antibody attached to a nucleic acid molecule (e.g., DNA). Each nucleic acid molecule serves as a splint for ligation of two probes which upon ligation form a circularized probe. Each of the two probes can comprise one or more barcode sequences. Further, one of the two probes may serve as a primer for rolling circle amplification of the circularized probe while the other probe has an end that is blocked from primer extension. The nucleic acid molecules, circularized probes, and RCA products can be analyzed using any suitable method disclosed herein for in situ analysis.

In any of the embodiments disclosed herein, disclosed herein is a multiplexed assay where multiple targets (e.g., nucleic acids such as genes or RNA transcripts, or protein targets) are probed with multiple primary probes (e.g., padlock primary probes), and optionally multiple secondary probes hybridizing to the primary barcodes (or complementary sequences thereof) are all hybridized at once, followed by sequential secondary barcode detection and decoding of the signals.

VII. Compositions, Kits, and Systems

In some embodiments, disclosed herein is a composition that comprises a complex containing a target nucleic acid, a padlock probe or circular probe, a primers, and an anchor, e.g., any of the target nucleic acids, padlock probes, circular probes, primers, and anchors described in Section III. In some embodiments, the complex further comprises a primer, e.g., as described in Section III.

In some embodiments, disclosed herein is a composition that comprises an amplification product containing an anchor portion, a primer portion, and monomeric units of a sequence complementary to a sequence of a padlock probe or circular probe. In some embodiments, the amplification product is formed using any of the target nucleic acids, circular or padlock probes, primers, and anchors described in Section III and any of the amplification techniques described in Section V. In some embodiments, the amplification product further comprises a primer, e.g., any of the primers described in Section III. In some embodiments, the amplification product forms a DNA nanoball.

Also provided herein are kits, for example comprising one or more polynucleotides, e.g., any described in Section III, and reagents for performing the methods provided herein, for example reagents required for one or more steps comprising hybridization, ligation, amplification, detection, sequencing, and/or sample preparation as described herein. In some embodiments, the kit further comprises a target nucleic acid, e.g., any described in Section III. In some embodiments, any or all of the polynucleotides are DNA molecules. In some embodiments, the target nucleic acid is a messenger RNA molecule. In some embodiments, the kit further comprises a ligase, for instance for forming a ligated anchor-primer and a circular probe from the padlock probe. In some embodiments, the ligase has DNA-splinted DNA ligase activity. In some embodiments, the kit further comprises a polymerase, for instance for performing amplification of the padlock probe. In some embodiments, the polymerase is capable of using the ligated anchor-primer as a primer and the circular probe as a template for amplification, e.g., using any of the methods described in Section V. In some embodiments, the kit further comprises a primer for amplification.

The various components of the kit may be present in separate containers or certain compatible components may be precombined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for fixing, embedding, and/or permeabilizing the biological sample. In some embodiments, the kits contain reagents, such as enzymes and buffers for ligation and/or amplification, such as ligases and/or polymerases. In some aspects, the kit can also comprise any of the reagents described herein, e.g., wash buffer and ligation buffer. In some embodiments, the kits contain reagents for detection and/or sequencing, such as, secondary probes, barcode detection probes or detectable labels. In some embodiments, the kits optionally contain other components, for example nucleic acid primers, enzymes and reagents, buffers, nucleotides, modified nucleotides, reagents for additional assays.

VIII. Applications

In some aspects, the provided embodiments can be applied in an in situ method of analyzing nucleic acid sequences, such as an in situ transcriptomic analysis or in situ sequencing, for example from intact tissues or samples in which the spatial information has been preserved. In some aspects, the embodiments can be applied in an imaging or detection method for multiplexed nucleic acid analysis. In some aspects, the provided embodiments can be used to identify or detect a region of interest in the target nucleic acid. In some aspects, the provided embodiments can be used to identify or detect one or more polymorphisms, e.g., single nucleotides of interest in the target nucleic acids.

In some embodiments, the region of interest may comprise a polymorphism. For example, the polymorphism may comprise one or more base changes, an insertion, a repeat, a deletion, a frame shift, an alternatively spliced sequence (s), or any combinations thereof. In some cases, a polymorphic locus may be as small as one base pair e.g., a single nucleotide of interest. In some embodiments, the single nucleotide of interest is a single-nucleotide polymorphism (SNP). In some embodiments, the single nucleotide of interest is a single-nucleotide variant. In some embodiments, the single nucleotide of interest is a single-nucleotide substitution. In some embodiments, the single nucleotide of interest is a point mutation. In some embodiments, the single nucleotide of interest is a single-nucleotide insertion.

In some aspects, the embodiments can be applied in investigative and/or diagnostic applications, for example, for characterization or assessment of particular cell or a tissue from a subject. Applications of the provided method can comprise biomedical research and clinical diagnostics. For example, in biomedical research, applications comprise, but are not limited to, spatially resolved gene expression analysis for biological investigation or drug screening. In clinical diagnostics, applications comprise, but are not limited to, detecting gene markers such as disease, immune responses, bacterial or viral DNA/RNA for patient samples.

In some aspects, the embodiments can be applied to visualize the distribution of genetically encoded markers in whole tissue at subcellular resolution, for example, chromosomal abnormalities (inversions, duplications, translocations, etc.), loss of genetic heterozygosity, the presence of gene alleles indicative of a predisposition towards disease or good health, likelihood of responsiveness to therapy, or in personalized medicine or ancestry.

IX. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The terms "polynucleotide," "polynucleotide," and "nucleic acid molecule", used interchangeably herein, refer to polymeric forms of nucleotides of any length, either ribonucleotides or deoxyribonucleotides. Thus, this term comprises, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups.

The terms "complementary" and "substantially complementary" may include the hybridization or base pairing or the formation of a duplex between nucleotides or nucleic acids, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%. In one aspect, two complementary sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

"Hybridization" as used herein may refer to the process in which two single-stranded polynucleotides bind non-covalently to form a stable double-stranded polynucleotide. In one aspect, the resulting double-stranded polynucleotide can be a "hybrid" or "duplex." "Hybridization conditions" typically include salt concentrations of approximately less than 1 M, often less than about 500 mM and may be less than about 200 mM. A "hybridization buffer" includes a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, i.e., conditions under which a sequence will hybridize to its target sequence but will not hybridize to other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. The melting temperature $T_m$ can be the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation, $T_m=81.5+0.41$ (% G+C), when a nucleic acid is in aqueous solution at 1 M NaCl (see e.g., Anderson and Young, Quantitative Filter Hybridization, in *Nucleic Acid Hybridization* (1985)). Other references (e.g., Allawi and SantaLucia, Jr., Biochemistry, 36:10581-94 (1997)) include alternative methods of computation which take structural and environmental, as well as sequence characteristics into account for the calculation of $T_m$.

In general, the stability of a hybrid is a function of the ion concentration and temperature. Typically, a hybridization reaction is performed under conditions of lower stringency, followed by washes of varying, but higher, stringency.

Exemplary stringent conditions include a salt concentration of at least 0.01 M to no more than 1 M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized. In one aspect, "stringency of hybridization" in determining percentage mismatch can be as follows: 1) high stringency: 0.1×SSPE, 0.1% SDS, 65° C.; 2) medium stringency: 0.2×SSPE, 0.1% SDS, 50° C. (also referred to as moderate stringency); and 3) low stringency: 1.0×SSPE, 0.1% SDS, 50° C. It is understood that equivalent stringencies may be achieved using alternative buffers, salts and temperatures. For example, moderately stringent hybridization can refer to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions can be conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization can refer to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa, Nucleic Acids Res. 12:203 (1984).

A "primer" used herein can be an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

"Ligation" may refer to the formation of a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide.

"Sequencing," "sequence determination" and the like means determination of information relating to the nucleotide base sequence of a nucleic acid. Such information may include the identification or determination of partial as well as full sequence information of the nucleic acid. Sequence information may be determined with varying degrees of statistical reliability or confidence. In one aspect, the term includes the determination of the identity and ordering of a plurality of contiguous nucleotides in a nucleic acid. "High throughput digital sequencing" or "next generation sequencing" means sequence determination using methods that determine many (typically thousands to billions) of nucleic acid sequences in an intrinsically parallel manner, i.e. where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, Conn.); sequencing by ligation (for example, as commercialized in the SOLiD™ technology, Life Technologies, Inc., Carlsbad, Calif.); sequencing by synthesis using modified nucleotides (such as commercialized in TruSeq™ and HiSeq™ technology by Illumina, Inc., San Diego, Calif; HeliScope™ by Helicos Biosciences Corporation, Cambridge, Ma.; and PacBio RS by Pacific Biosciences of California, Inc., Menlo Park, Calif), sequencing by ion detection technologies (such as Ion Torrent™ technology, Life Technologies, Carlsbad, Calif); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

"SNP" or "single nucleotide polymorphism" may include a genetic variation between individuals; e.g., a single nitrogenous base position in the DNA of organisms that is variable. SNPs are found across the genome; much of the genetic variation between individuals is due to variation at SNP loci, and often this genetic variation results in phenotypic variation between individuals. SNPs for use in the present invention and their respective alleles may be derived from any number of sources, such as public databases (U.C. Santa Cruz Human Genome Browser Gateway (genome.ucsc.edu/cgi-bin/hgGateway) or the NCBI dbSNP website (www.ncbi.nlm.nih gov/SNP/), or may be experimentally determined as described in U.S. Pat. No. 6,969,589; and US Pub. No. 2006/0188875 entitled "Human Genomic Polymorphisms." Although the use of SNPs is described in some of the embodiments presented herein, it will be understood that other biallelic or multi-allelic genetic markers may also be used. A biallelic genetic marker is one that has two polymorphic forms, or alleles. As mentioned above, for a biallelic genetic marker that is associated with a trait, the allele that is more abundant in the genetic composition of a case group as compared to a control group is termed the "associated allele," and the other allele may be referred to as the "unassociated allele." Thus, for each biallelic polymorphism that is associated with a given trait (e.g., a disease or drug response), there is a corresponding associated allele. Other biallelic polymorphisms that may be used with the methods presented herein include, but are not limited to multinucleotide changes, insertions, deletions, and translocations. It will be further appreciated that references to DNA herein may include genomic DNA, mitochondrial DNA, episomal DNA, and/or derivatives of DNA such as amplicons, RNA transcripts, cDNA, DNA analogs, etc. The polymorphic loci that are screened in an association study may be in a diploid or a haploid state and, ideally, would be from sites across the genome.

"Multiplexing" or "multiplex assay" herein may refer to an assay or other analytical method in which the presence and/or amount of multiple targets, e.g., multiple nucleic acid target sequences, can be assayed simultaneously by using more than one capture probe conjugate, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

The term "about" as used herein refers to the usual error range for the respective value readily known to the skilled person in this technical field. Reference to "about" a value or parameter herein comprises (and describes) embodiments that are directed to that value or parameter per se.

As used herein, the singular forms "a," "an," and "the" comprise plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be comprised in the smaller ranges, and are also encompassed within the claimed subject matter, subject to any specifically excluded limit in the stated range. Where the stated range comprises one or both of the limits, ranges excluding either or both of those comprised limits are also comprised in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

EXAMPLES

Example 1: Design of Probes

This Example describes the design of a three-polynucleotide probe set for amplification and identification of single nucleotides of interest in target nucleic acids, such as SNPs in messenger RNA. The probe set permits highly sensitive and specific detection of SNPs in highly complex samples, for example in intact biological tissue containing numerous different mRNA sequences. As a result, image-based quantification of SNPs at subcellular resolution is enabled.

The probe set is designed such that when each probe hybridizes to its complementary sequence, the probes are in close enough proximity to one another to permit ligation of the probes. The probe set is also designed such that this ligation occurs if one or both of the probes to be ligated contains a nucleotide that hybridizes to a single nucleotide of interest in the target nucleic acid.

Figure 2:
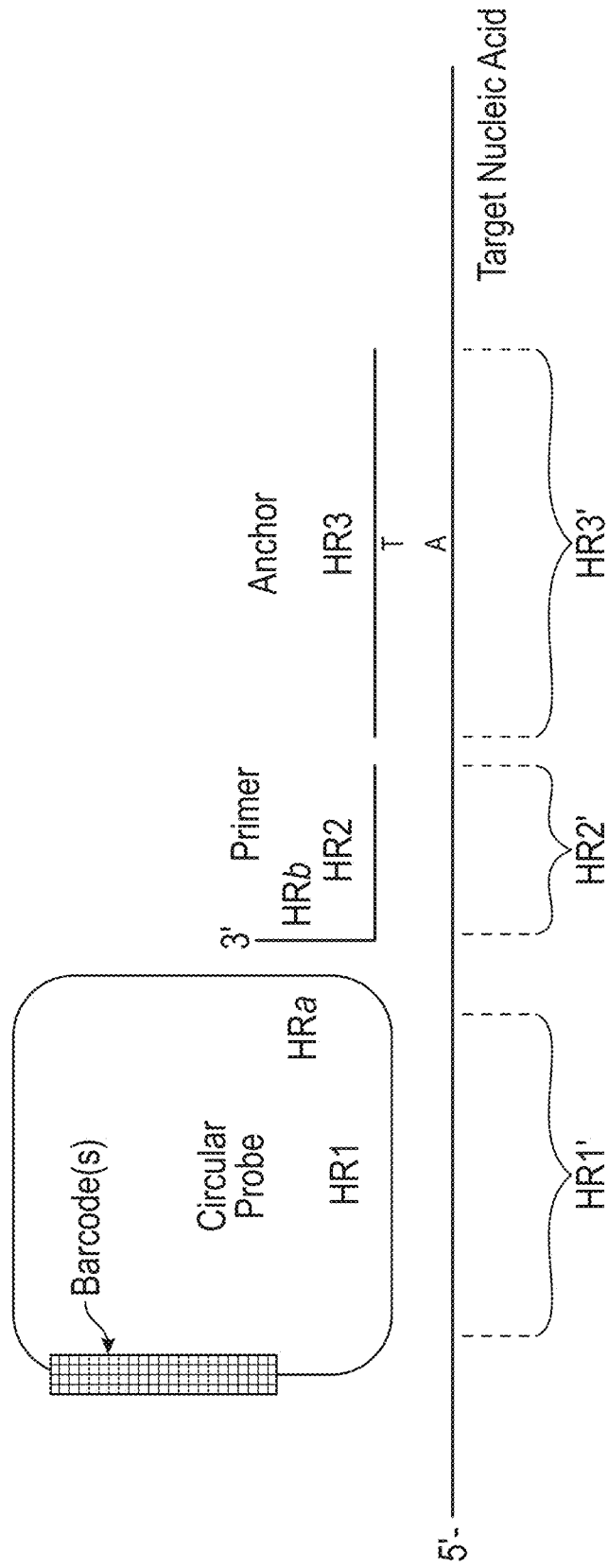
FIG. 2 depicts exemplary probe polynucleotides, comprising a circular probe, a primer, and an anchor, for use in analyzing a region of interest (e.g., a sequence of 5 nucleotides or shorter such as a single nucleotide of interest) in a target nucleic acid in a biological sample.
Figure 3:
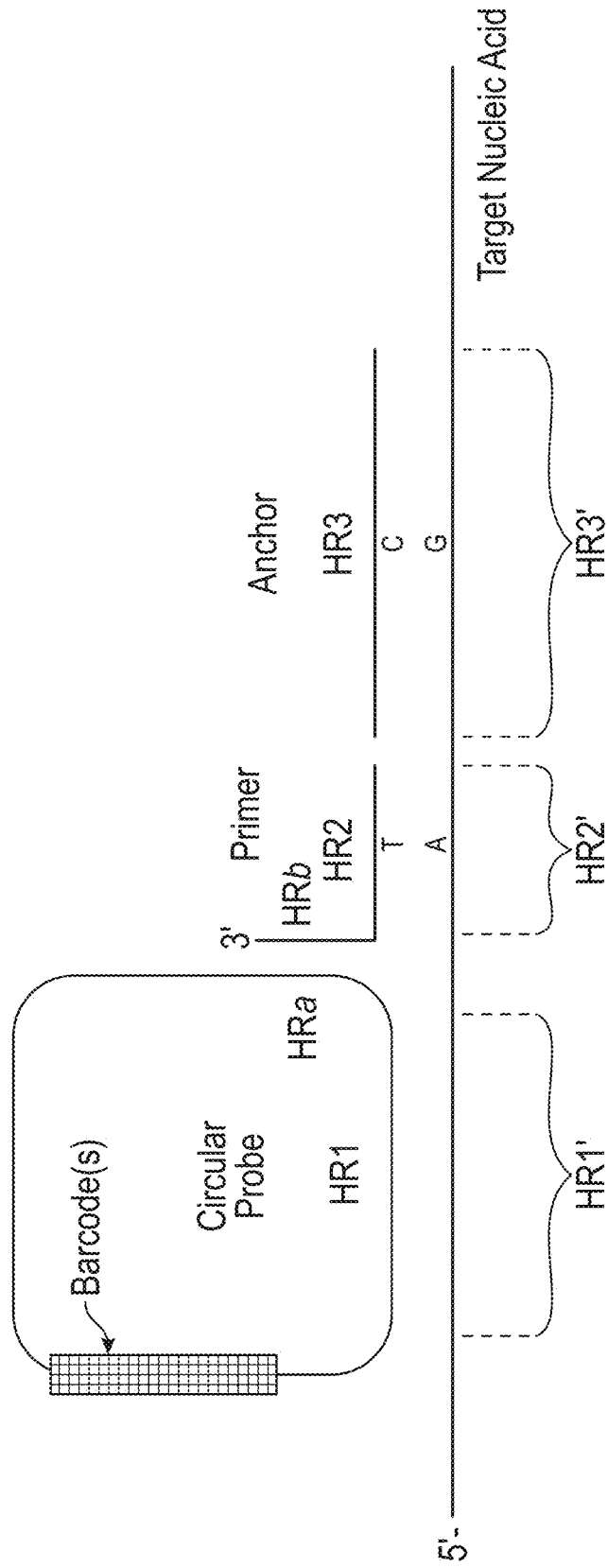
FIG. 3 depicts exemplary probe polynucleotides, comprising a circular probe, a primer, and an anchor, for use in analyzing one or more regions of interest (e.g., a sequence of 5 nucleotides or shorter such as a single nucleotide of interest) in a target nucleic acid in a biological sample.
Figure 4:
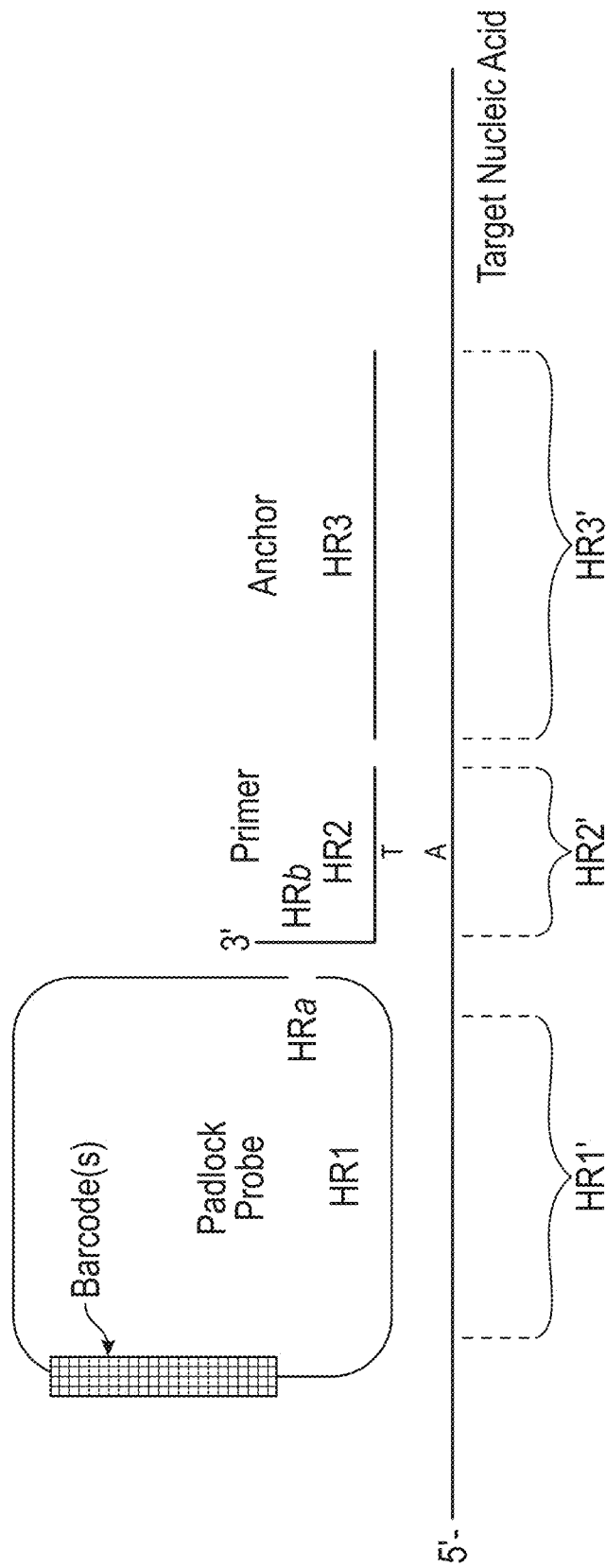
FIG. 4 depicts exemplary probe polynucleotides, comprising a padlock probe, a primer, and an anchor, for use in analyzing a region of interest (e.g., a sequence of 5 nucleotides or shorter such as a single nucleotide of interest) in a target nucleic acid in a biological sample.
Figure 5:
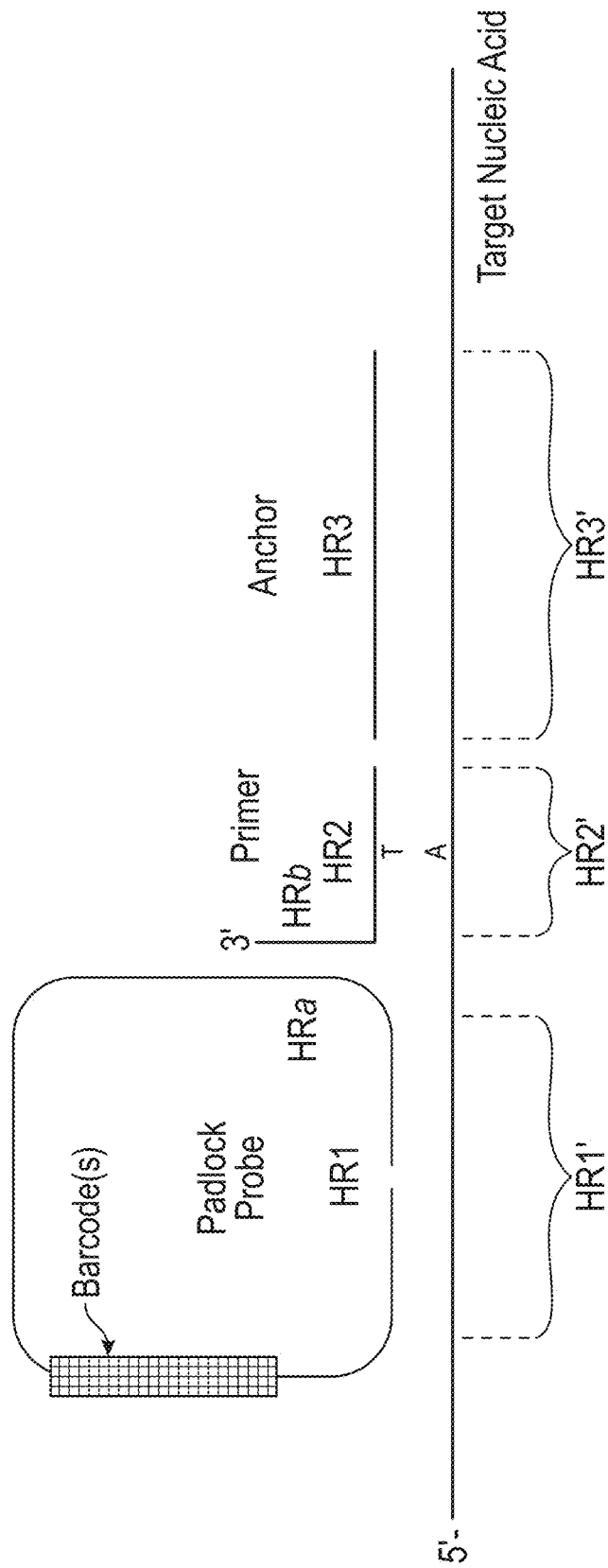
FIG. 5 depicts exemplary probe polynucleotides, comprising a padlock probe, a primer, and an anchor, for use in analyzing a region of interest (e.g., a sequence of 5 nucleotides or shorter such as a single nucleotide of interest) in a target nucleic acid in a biological sample.

FIG. 1-5 depict exemplary probe sets hybridized to target nucleic acid (e.g., an mRNA). FIGS. 1-3 depict probe sets with a circular probe, a primer, and an anchor. FIGS. 4 and 5 depict probe sets with a padlock probe, a primer, and anchor. Each polynucleotide comprises two or more hybridization regions (HRs) that are complementary to other HRs contained in the target mRNA or another polynucleotide. The anchor contains a hybridization region HR3 that is complementary to HR3' of the target mRNA. The primer contains two HRs: HRb and HR2, with HRb being 3' to HR2. The circular probe of FIGS. 1-3 contains hybridization regions HRa and HR1, as does the padlock probe of FIGS. 4 and 5. Outside of these HRs, the circular probe of FIGS. 1-3 and the padlock probe of FIGS. 4 and 5 can contain barcodes that identify a single nucleotide of interest. In the case of the padlock probe, either HRa (FIG. 4) or HR1 (FIG. 5) can be a split hybridization region containing the 5' and 3' ends of the padlock probe. HRb of the primer is complementary to HRa. HR2 of the primer is complementary to HR2' of the target nucleic acid, and HR1 is complementary to HR1' of the target nucleic acid. HR1', HR2', and HR3' are adjacent to one another, with HR1' being 5' of HR2' and HR2' being 5' to HR3'. A single nucleotide of interest can be contained in HR2' (FIG. 1), HR3' (FIG. 2), or both (FIG. 3). The melting temperature of the hybridization between HR2/HR2' and/or HR3/HR3' is higher when HR2 and/or HR3 contain nucleotides complementary to the single nucleotides of interest than when HR2 and/or HR3 do not contain nucleotides complementary to the single nucleotides of interest.

Upon hybridization of the probes, the 5' end nucleotide of the primer is in proximity to be ligated with or without gap-filling to the 3' end of the anchor using the target mRNA as a template. For the padlock probe of FIG. 4 and FIG. 5, the padlock probe is circularized upon hybridization either to HRb (FIG. 4) or to HR1' (FIG. 5) such that the ends of the padlock probe can be ligated with or without gap-filling to form a circular probe using as a template the primer (FIG. 5) or the target mRNA (FIG. 5). After ligation, the circular probe can be amplified using rolling circle amplification using the free 3' end of the primer for amplification priming.

Example 2: Hybridization, Amplification, and Detection

Exemplary probe sets as described in Example 1 above are hybridized, amplified, detected and sequenced for in situ detection of SNPs in a biological sample, such as a tissue section.

A library of different DNA probe sets with circular probes and targeting various SNPs both within and across genes are pooled. The probe mixture is heated, cooled down to room temperature, and incubated with a thin tissue section sample and hybridization buffer for hybridization of the probe sets to target mRNAs in the sample. After hybridization, the sample is then washed and incubated with a SplintR ligase for ligation of the anchors to the primers. The hybridization, ligation, and wash steps can be performed at a temperature that is below the melting temperature ($T_m$) of the hybridizations between HR1/HR1', HR2/R2', HRa/HRb, and/or HR3/HR3' when HR2 and/or HR3 contain a nucleotide that hybridizes to a target SNPs, but higher than the melting temperature ($T_m$) of each of the hybridizations between HR2/R2' and/or HR3/HR3' when HR2 and/or HR3 do not contain a nucleotide that hybridizes to a target SNPs.

A stringent wash is then performed, and the sample is then incubated with a rolling-circle amplification (RCA) mixture containing a Phi29 DNA polymerase and dNTP for RCA of the circular probes. In some instances, modified nucleotide bases (e.g., 5-(3-aminoallyl)-dUTP) are also comprised in the RCA mixture. The stringent wash (e.g., conditions including temperature of about 5° C. less that the $T_m$ of a strand of the duplex and low monovalent salt concentration, e.g., less than 0.2 M, or less than 0.1 M) and RCA are performed at a temperature that is lower than the $T_m$ of the ligated anchor-primers for hybridization to the target SNPs and the circular probes, and higher than the $T_m$ of the unligated anchors for hybridization to the target mRNAs and the $T_m$ of the unligated primers for hybridization to the circular probes or to the target mRNAs.

Figure 6:
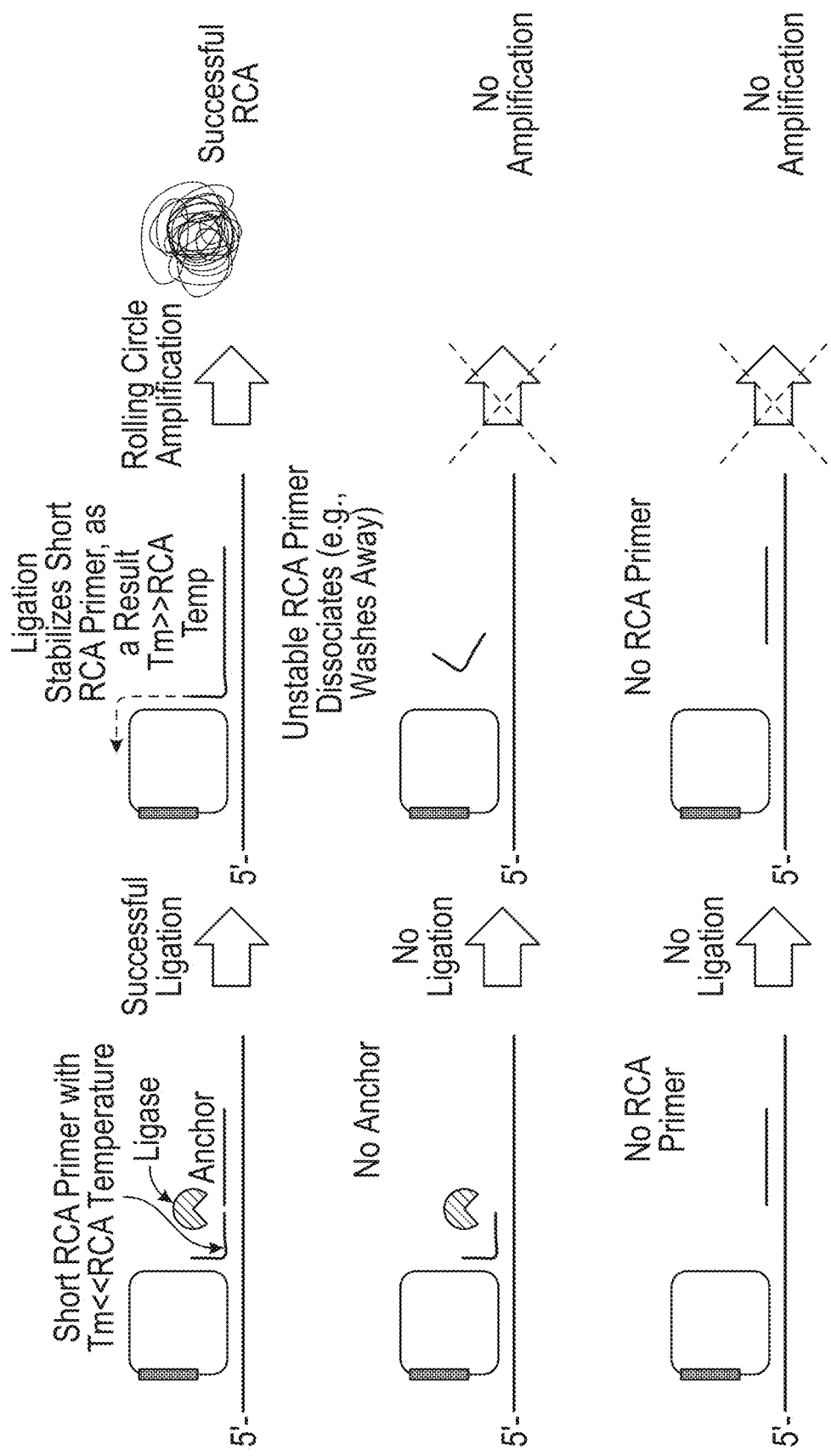
FIG. 6 shows exemplary methods comprising ligation and subsequent RCA when a primer and an anchor both hybridize to a target and come into close enough proximity for ligation to occur. In the absence of the anchor and primer-anchor ligation, the primer is not stably hybridized to the target and can be dissociated, e.g., washed away. In the absence of the primer and primer-anchor ligation, there is no priming on the circular probe and accordingly no RCA.
Figure 9:
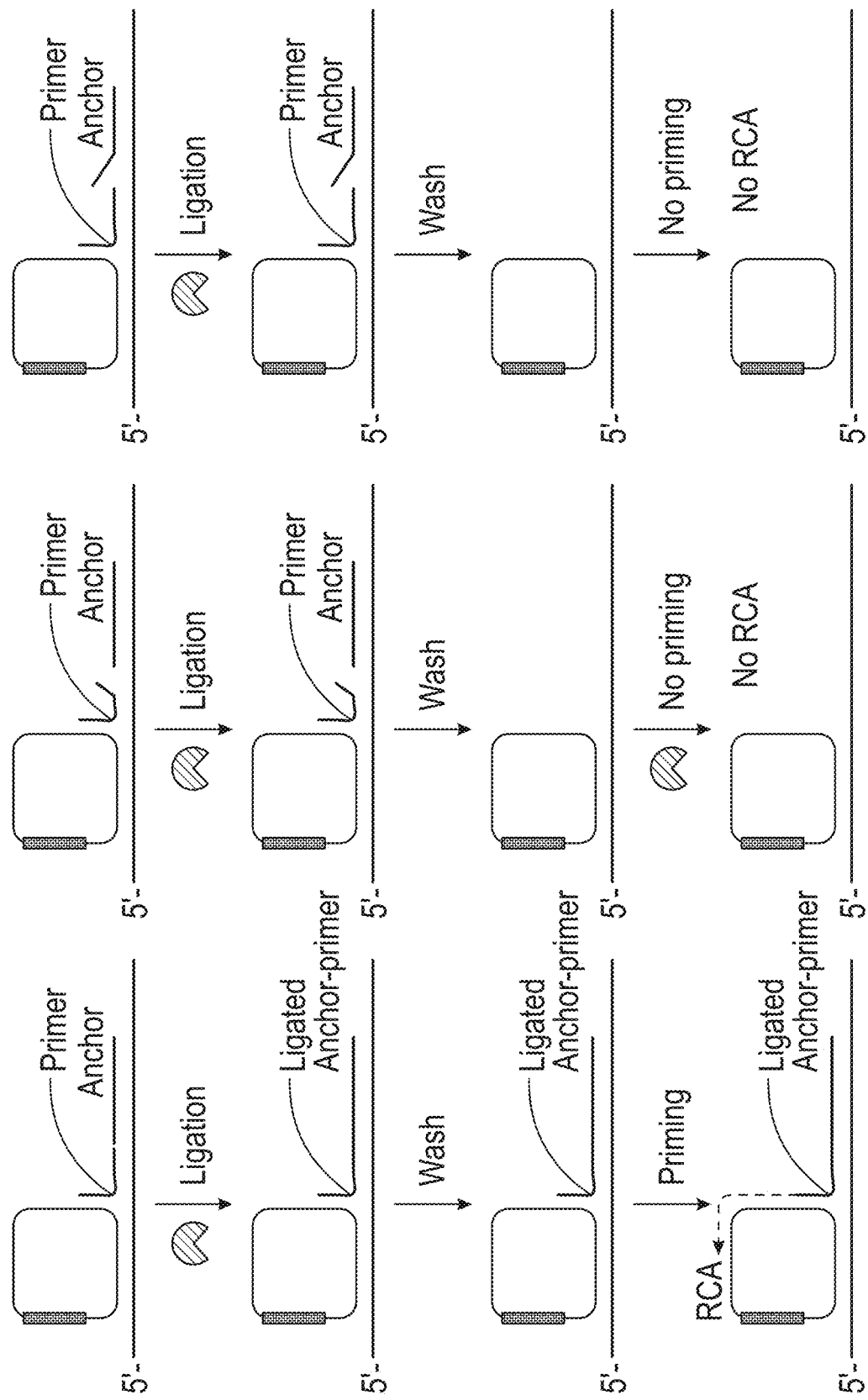
FIG. 9 shows exemplary methods where a circular/padlock probe, a primer, and an anchor are all hybridized on a target. When neither the primer nor the probe comprises a mismatch, a ligase (such as a high fidelity ligase capable of RNA-templated ligation) ligates the primer to the anchor for subsequent RCA of the circular/padlock probe. When either the primer or the anchor comprises a mismatch, the ligase does not ligate, and both the unligated primer and unligated anchor can be dissociated (e.g., washed away under stringent conditions).
Figure 10:
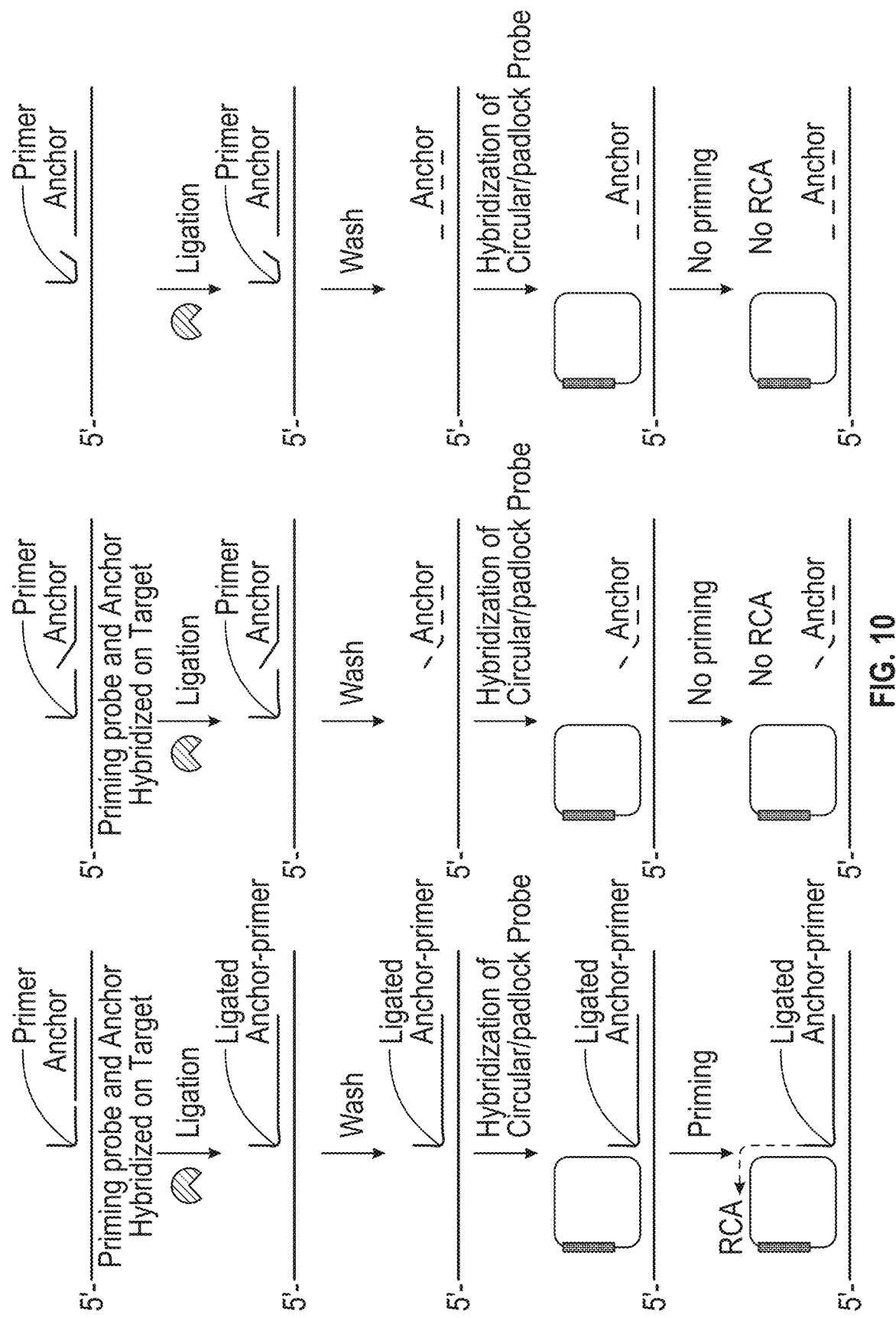
FIG. 10 shows exemplary methods where a primer and an anchor are first hybridized on a target. When neither the primer nor the anchor comprises a mismatch, a ligase (such as a high fidelity ligase capable of RNA-templated ligation) ligates the primer to the anchor, as shown in the left panel. A circular/padlock probe is then hybridized to the target for subsequent RCA. When either the primer or the anchor comprises a mismatch, as shown in the center and right panels, respectively, the ligase does not ligate, and the unligated primer is dissociated (e.g., washed away under stringent conditions). The unligated anchor optionally may remain bound (as indicated by the dashed line depicting an optionally bound anchor) or may also be washed away under stringent conditions.

FIGS. 6 and 9 depict exemplary outcomes of the ligation, stringent wash, and RCA steps. As shown in FIG. 6, ligation and subsequent RCA amplification occur when each of the probes hybridizes and come into close enough proximity for ligation to occur. As shown in the left column of FIG. 9, probe sets that bind to a target SNP have their anchors ligated to primers, and the ligated anchor-primers remain stably hybridized after the stringent wash. In this case, productive RCA is achieved. As shown in the middle column of FIG. 9, probe sets whose primers contain a mismatch with a target SNP do not have their anchors ligated to primers, and the unligated primers and/or anchors may be washed away. In this case, RCA priming is not achieved, and the circular probe is not amplified. Similarly, as shown in the right column of FIG. 9, probe sets whose anchors contain a mismatch with a target SNP do not have their anchors ligated to primers, and the unligated primers and/or anchors are washed away. In this case, RCA priming is not achieved, and the circular probe is not amplified.

For single-SNP detection, fluorescently labeled oligonucleotides complementary to a portion of the amplified circular probes are incubated with the sample, and after a wash step, images are obtained.

For sequencing, the sample is treated with stripping buffer, washed, and incubated with a sequencing mixture containing a T4 DNA ligase and fluorescently labeled sequencing oligonucleotides, and images are obtained. Multiple cycles of sequencing is performed. Images are acquired using a confocal microscope.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for analyzing a region of interest in a target nucleic acid, the method comprising:
    (i) contacting the target nucleic acid with a circular or padlock probe, a primer, and an anchor to form a hybridization complex, wherein:

the circular or padlock probe comprises adjacent hybridization regions HR1 and HRa, the primer comprises adjacent hybridization regions HRb and HR2, the anchor comprises hybridization region HR3, and the target nucleic acid comprises adjacent hybridization regions HR1', HR2', and HR3', wherein HR2' or HR3' comprises the region of interest, and HR1 hybridizes to HR1', HRa hybridizes to HRb, HR2 or HR3 comprises at least one nucleotide complementary to the region of interest, and HR2 and HR3 hybridize to HR2' and HR3', respectively, thereby hybridizing the circular or padlock probe, the primer, and the anchor to the target nucleic acid;

(ii) ligating the 3' end of the anchor and the 5' end of the primer to form a ligated anchor-primer;

(iii) forming an amplification product using the circular probe or a circular probe formed from the padlock probe as a template and the ligated anchor-primer as a primer; and (iv) detecting the amplification product.

2. The method of claim 1, wherein the target nucleic acid is an mRNA or a pre-mRNA.

3. The method of claim 1, wherein the target nucleic acid is in a tissue sample, and the region of interest is analyzed in situ in the tissue sample.

4. The method of claim 1, wherein hybridization region HR2' comprises the region of interest.

5. The method of claim 1, wherein the circular or padlock probe is a circular probe.

6. The method of claim 1, wherein the circular or padlock probe is a padlock probe, and the method comprises ligating the padlock probe to form a circular probe.

7. The method of claim 1, wherein the circular or padlock probe comprises a barcode sequence.

8. The method of claim 7, wherein the barcode sequence identifies the region of interest.

9. The method of claim 1, wherein hybridization region HRb is between about 3 and about 10 nucleotides in length.

10. The method of claim 1, wherein hybridization region HR2 is between about 5 and about 15 nucleotides in length.

11. The method of claim 1, wherein the at least one nucleotide complementary to the region of interest is at the 5' end of the primer.

12. The method of claim 1, further comprising a step of removing molecules that are not specifically hybridized to the target nucleic acid and/or the circular probe after the ligation.

13. The method of claim 1, wherein the amplification product is formed using rolling circle amplification (RCA).

14. The method of claim 1, wherein the detecting of the amplification product comprises sequencing all or a portion of the amplification product and/or in situ hybridization to the amplification product.

15. The method of claim 1, wherein the region of interest is a polymorphism selected from the group consisting of a single-nucleotide polymorphism (SNP), a single-nucleotide variant (SNV), a single-nucleotide substitution, a point mutation, a single-nucleotide insertion, and a single-nucleotide deletion.

16. The method of claim 15, wherein the polymorphism is in HR2', and the at least one nucleotide complementary to the region of interest is between about 15 nucleotides and about 1 nucleotide from the 5' end of the primer.

17. A method for analyzing a single nucleotide of interest in a target mRNA, the method comprising:

(i) contacting the target mRNA with a single-stranded circular probe, a primer, and an anchor to form a hybridization complex, wherein the circular probe, the primer, and the anchor are DNA molecules, and wherein:

the circular probe comprises adjacent hybridization regions HR1 and HRa, the primer comprises adjacent hybridization regions HRb and HR2, the anchor comprises hybridization region HR3, and the target mRNA comprises adjacent hybridization regions HR1', R2', and HR3', wherein HR2' comprises the single nucleotide of interest, HR1 hybridizes to HR1', HRa hybridizes to HRb, HR2 comprises a nucleotide complementary to the single nucleotide of interest and is between 5 and 15 nucleotides in length, and HR2 and HR3 hybridize to R2' and HR3', respectively, thereby hybridizing the circular probe, the primer, and the anchor to the target mRNA and directly juxtaposing the 3' end of the anchor and the 5' end of the primer;

(ii) ligating the 3' end of the anchor and the 5' end of the primer to form a ligated anchor-primer, using a ligase having an RNA-splinted DNA ligase activity and the target mRNA as a template;

(iii) forming a rolling circle amplification product using the circular probe as a template and the ligated anchor-primer as a primer; and (iv) determining a sequence in the rolling circle amplification product indicative of the single nucleotide of interest.

18. A method for analyzing a single nucleotide of interest in a target mRNA, the method comprising:

(i) contacting the target mRNA with a primer and an anchor, wherein the primer comprises adjacent hybridization regions HRb and HR2, the anchor comprises hybridization region HR3, and the target mRNA comprises adjacent hybridization regions HR1', HR2', and HR3', wherein R2' comprises the single nucleotide of interest and HR2 comprises a nucleotide complementary to the single nucleotide of interest and is between 5 and 15 nucleotides in length, and HR2 and HR3 hybridize to R2' and HR3', respectively, thereby hybridizing the primer and the anchor to the target mRNA and directly juxtaposing the 3' end of the anchor and the 5' end of the primer;

(ii) ligating the 3' end of the anchor and the 5' end of the primer to form a ligated anchor-primer hybridized to the target mRNA, using a ligase having an RNA-splinted DNA ligase activity and the target mRNA as a template, at a temperature below the melting temperature ($T_m$) of the primer for hybridization to the target mRNA, wherein the temperature is above the $T_m$ of the primer for hybridization to the target mRNA when the primer does not comprise the nucleotide complementary to the single nucleotide of interest;

(iii) removing molecules that are not specifically hybridized to the target mRNA;

(iv) contacting the ligated anchor-primer hybridized to the target mRNA with a padlock probe comprising adjacent hybridization regions HR1 and HRa, wherein HR1 hybridizes to HR1' in the target mRNA and HRa hybridizes to HRb in the primer, wherein the padlock probe is circularized to form a circular probe;

(v) forming a rolling circle amplification product using the circular probe as a template and the ligated anchor-primer as a primer; and (vi) determining a sequence in the rolling circle amplification product indicative of the single nucleotide of interest.

\* \* \* \* \*